United States Patent
Tanikawa et al.

[11] Patent Number: 5,929,074
[45] Date of Patent: Jul. 27, 1999

[54] PYRIDAZINONE DERIVATIVES WITH PHARMACEUTICAL ACTIVITY

[75] Inventors: Keizo Tanikawa, Funabashi; Akira Saito, Onoda; Mitsuaki Hirotsuka, Funabashi; Ken-ichi Shikada, Shiraoka-machi, all of Japan

[73] Assignee: Nissan Chemical Industries, Ltd., Tokyo, Japan

[21] Appl. No.: 08/986,420

[22] Filed: Dec. 8, 1997

Related U.S. Application Data

[63] Continuation of application No. 08/564,277, filed as application No. PCT/JP94/01015, Jun. 24, 1994, Pat. No. 5,728,702.

[30] Foreign Application Priority Data

Jun. 29, 1993 [JP] Japan ................................ 5-159194
May 26, 1994 [JP] Japan ................................ 6-112721

[51] Int. Cl.⁶ .................. A61K 31/50; C07D 401/12; C07D 237/22
[52] U.S. Cl. .................. 514/247; 514/252; 544/238; 544/241
[58] Field of Search ................... 544/238, 240, 544/241; 514/247, 252, 253

[56] References Cited

U.S. PATENT DOCUMENTS

| | | | |
|---|---|---|---|
| 4,978,665 | 12/1990 | Tanikawa et al. | 514/247 |
| 5,202,323 | 4/1993 | Tanikawa et al. | 514/236.5 |
| 5,750,523 | 5/1998 | Tanikawa et al. | 514/247 |

FOREIGN PATENT DOCUMENTS

| | | |
|---|---|---|
| 0 186 817 | 7/1986 | European Pat. Off. |
| 0 275 997 | 7/1988 | European Pat. Off. |
| 0 482 208 | 4/1992 | European Pat. Off. |

*Primary Examiner*—Emily Bernhardt
*Attorney, Agent, or Firm*—Oblon, Spivak, McClelland, Maier & Neustadt, P.C.

[57] ABSTRACT

A 3(2H)-pyridazinone derivative of the formula (I) its salt, a process for its production and a pharmaceutical composition containing it.

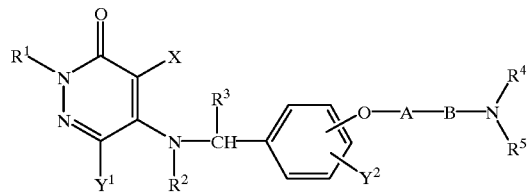

wherein each of $R^1$, $R^2$ and $R^3$ which are independent of one another, is a hydrogen atom or a $C_{1-4}$ alkyl group, X is a chlorine atom or a bromine atom, $Y^1$ is a hydrogen atom, a halogen atom, a nitro group, an amino group or a $C_{1-4}$ alkoxy group, $Y^2$ is a hydrogen atom, a halogen atom, a hydroxyl group, a $C_{1-4}$ alkyl group or a $C_{1-4}$ alkoxy group, A is a $C_{1-5}$ alkylene chain which may be substituted by a hydroxyl group, B is a carbonyl group or a methylene chain which may be substituted by a $C_{1-4}$ alkyl group, and each of $R^4$ and $R^5$ which are independent of each other, is a $C_{1-4}$ alkyl group, or $R^4$ is a hydrogen atom and $R^5$ is —Z—Ar (wherein Z is a $C_{1-5}$ alkylene chain, and Ar is an aromatic 6-membered ring which may contain a nitrogen atom), or $R^4$ and $R^5$ together form a $C_{2-6}$ cyclic alkylene group, or $R^4$ and $R^5$ form together with the adjacent nitrogen atom a 4-substituted piperazine ring of the formula:

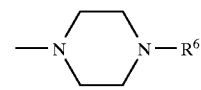

wherein $R^6$ is a $C_{1-4}$ alkyl group.

7 Claims, No Drawings

PYRIDAZINONE DERIVATIVES WITH PHARMACEUTICAL ACTIVITY

This application is a Continuation of prior application Ser. No: 08/564,277 filed Mar. 22, 1996, now U.S. Pat. No. 5,728,702, which was filed as International Application No. PCT/JP94/01015 filed Jun. 24, 1994.

TECHNICAL FIELD

The present invention relates to novel 3(2H)-pyridazinone derivatives and their pharmaceutically acceptable salts having bronchodilator activities, antiallergy activities and/or antiplatelet activities.

BACKGROUND ART

1) Field of Bronchodilator

In the treatment of chronic reversible obstructive respiratory diseases such as bronchial asthma, bronchitis and adult respiratory distress syndrome, air way remission at the time of seizure is important. For such a purpose, bronchodilators are used. Major bronchodilators presently used for clinical purposes may be generally classified into β-stimulants including Salbutamol and xanthine drugs represented by theophylline. The former drugs have a drawback that the effects decrease against intractable diseases, and a deterioration of the symptom due to frequent long-term administration has been pointed out in the treatment of bronchial asthma (The New England Journal of Medicine, vol 321, p. 1517–1527, 1989).

On the other hand, theophylline drugs have a limited use since their safety range is narrow.

2) Field of Antiallergic Drug

Various in vivo chemical mediators are believed to take part in immediate allergy diseases such as bronchial asthma, allergic rhinitis, hives and hey fever. Among them, histamine is one of important mediators, and antihistaminic agents have been used as antiallergic drugs since long ago. However, many of antiallergic drugs of antihistaminic type have central side effects such as drowsiness. For the treatment of asthma, a drug which has not only an antiallergic activity but also a bronchodilator activity will be significant from the viewpoint of the treatment and economy, but a drug having such functions has not yet been clinically developed.

3) Field of Antiplatelet Agent

It is known that platelets play an important role for thrombus formation in connection with a disease state through activation by stimulation, adhesion to vascular walls and aggregation. Various thrombotic diseases caused by thrombus formation include, for example, cerebral thrombosis, pulmonal thrombosis, myocardial infarction, angina pectoris and occlusion of peripheral artery, as main diseases, and all of these diseases require development of useful drugs. As a prophylactic or therapeutic drug, an attention has been drawn to an antiplatelet agent having an inhibitory activity of platelet aggregation. Heretofore, the effect of aspirin has been widely studied, and more recently ticlopidine and cilostazol have been clinically developed. However, a more strongly effective drug is desired in respect of its effects.

In addition to the above-mentioned various thrombotic diseases, there are enumerated various diseases in relation to platelets. Examples of these diseases include nephritis, cancer cell metastasis and the like, and recently various studies have been conducted with regard to prophylactic or therapeutic effects for these diseases achieved mainly by an anti-thrombotic agent having an activity for controlling platelet function ("Journal of Royal College of Physicians", Vol. 7, No. 1, p. 5–18, 1972; "Japan Clinics (Nihon Rinsho)", Vol. 4, No. 6, p. 130–136, 1988; Anticancer Research, Vol 6, p. 543–548, 1986).

Now, the relationship of 5-ω-aminoalkyleneoxy or ω-aminocarbonylalkyleneoxy substituted benzylamino)-3 (2H)-pyridazinone derivatives of the formula (I) and their pharmaceutically acceptable salts according to the present invention with the compounds disclosed in published references will be described.

Compounds of the type wherein a substituted benzylamino group is bonded to the 5-position of a 3(2H)-pyridazinone ring, which are relatively similar to the compounds of the present invention, are disclosed in the following references.

(a) Japanese Patent Publication No. 41455/1994, EP186817B or U.S. Pat. No. 5,098,900 (hereinafter referred to as reference (a)) discloses compounds including 3(2H)-pyridazinone derivatives wherein the 2-position is a lower alkyl group, the 4-position is a chlorine atom or a bromine atom, the 5-position is a benzylamino group having the benzene ring substituted by a substituent including a ω-aminoalkyl group, a ω-carbamoylalkyleneoxy group, a ω-N-mono lower alkylaminocarbonylalkyleneoxy group and an aminocarbonyl group, and their pharmaceutical use as anti SRS-A agents and their pharmacological activities.

(b) Japanese Unexamined Patent Publication No. 030769/1987, EP201765B or U.S. Pat. No. 4,892,947 (hereinafter referred to as reference (b)) discloses compounds including 3(2H)-pyridazinone derivatives wherein the 2-position is a hydrogen atom, the 4-position is a chlorine atom or a bromine atom, the 5-position is a benzylamino group having the benzene ring substituted by a substituent including an alkyloxy group, a ω-phenylalkyleneoxy group and a dialkylamino group, and the 6-position is a hydrogen atom, and their pharmaceutical use as anti SRS-A agents and their pharmacological activities.

(c) Japanese Unexamined Patent Publication No. 301870/1988, EP275997B or U.S. Pat. No. 4,978,665 (hereinafter referred to as reference (c)) discloses compounds including 3(2H)-pyridazinone derivatives wherein the 2-position is a hydrogen atom or a lower alkyl group, the 4-position is a chlorine atom or a bromine atom, the 5-position is a benzylamino group having the benzene ring substituted by a substituent including an alkyloxy group, a ω-phenylalkyleneoxy group and a dialkylamino group, and the 6-position is a halogen atom, a nitro group, an amino group or an alkoxy group, and their pharmaceutical use as anti SRS-A agents and their pharmacological activities.

(d) WO91/16314, EP482208A or U.S. Pat. No. 5,202,323 (hereinafter referred to as reference (d)) discloses compounds including 3(2H)-pyridazinone derivatives wherein the 2-position is a hydrogen atom or a lower alkyl group, the 4-position is a chlorine atom or a bromine atom, the 5-position is a benzylamino group having the benzene ring substituted by a substituent including an alkyloxy group, a ω-phenylalkyleneoxy group wherein the benzene ring may be substituted by an alkyl group or a halogen atom, a ω-alkoxycarbonylalkyleneoxy group and a ω-aminocarbonylalkyleneoxy group, and the 6-position is an alkyleneoxy group having a various functional group at the ω-position, and their pharmaceutical uses as antithrombotic agents, cardiotonic agents, vasodilators and anti SRS-A agents and their pharmacological activities.

DISCLOSURE OF THE INVENTION

As a result of an extensive study, the present inventors have discovered that the 3(2H)-pyridazinone derivatives and their pharmaceutically acceptable salts of the present invention, which are different from any of the compounds disclosed in the above references (a) to (d), are superior compounds for vasodilators, antiallergic drugs or/and antiplatelet agents, they show particularly excellent activities by oral administration, and they are useful as active ingredients of prophylactic or therapeutic drugs for e.g. the above-mentioned respiratory diseases, immediate allergic diseases or/and thrombotic diseases. The present invention has been accomplished on the basis of this discovery.

That is, the present invention provides a 3(2H)-pyridazinone derivative of the formula (I) and its pharmaceutically acceptable salt, a process for producing the same and a pharmaceutical composition containing the same as an active ingredient:

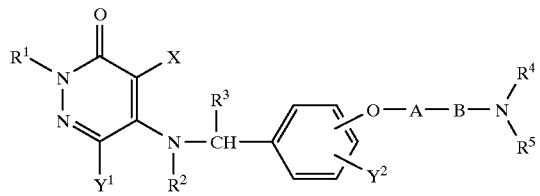

(I)

wherein each of $R^1$, $R^2$ and $R^3$ which are independent of one another, is a hydrogen atom or a $C_{1-4}$ alkyl group, X is a chlorine atom or a bromine atom, $Y^1$ is a hydrogen atom, a halogen atom, a nitro group, an amino group or a $C_{1-4}$ alkoxy group, $Y^2$ is a hydrogen atom, a halogen atom, a hydroxyl group, a $C_{1-4}$ alkyl group or a $C_{1-4}$ alkoxy group, A is a $C_{1-5}$ alkylene chain which may be substituted by a hydroxyl group, B is a carbonyl group or a methylene chain which may be substituted by a $C_{1-4}$ alkyl group, and each of $R^4$ and $R^5$ which are independent of each other, is a $C_{1-4}$ alkyl group, or $R^4$ is a hydrogen atom and $R^5$ is -Z-Ar (wherein Z is a $C_{1-5}$ alkylene chain, and Ar is an aromatic 6-membered ring which may contain one or two nitrogen atoms), or $R^4$ and $R^5$ together form a $C_{2-6}$ cyclic alkylene group, or $R^4$ and $R^5$ form together with the adjacent nitrogen atom a 4-substituted piperazine ring of the formula:

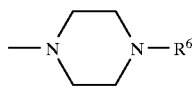

(wherein $R^6$ is a $C_{1-4}$ alkyl group (this alkyl group may be substituted by one or more substituents selected from a group of substituents consisting of a $C_{1-4}$ alkyl group, a phenyl group which may be substituted by $Y^3$ (wherein $Y^3$ is a hydrogen atom, a halogen atom, a $C_{1-4}$ alkyl group, a $C_{1-4}$ alkoxy group, an amino group, an N-formyl group or a $C_{1-4}$ alkylcarbonylamino group),

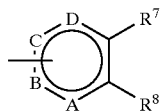

(wherein each of $R^7$ and $R^8$ is a hydrogen atom, or $R^7$ and $R^8$ form together with the carbon atoms to which they are bonded, a benzene ring, and each of A, B, C and D which are independent of one another, is a nitrogen atom or a carbon atom) and

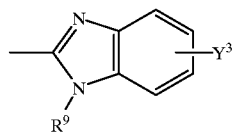

(wherein $Y^3$ is as defined above, and $R^9$ is a $C_{1-4}$ alkyl group or a benzyl group which may be substituted by a $C_{1-4}$ alkyl group, a $C_{1-4}$ alkoxy group or a halogen atom)) or —$COR^{10}$ (wherein $R^{10}$ is a hydrogen atom or a $C_{1-4}$ alkyl group)} or a 4-substituted piperidine ring of the formula:

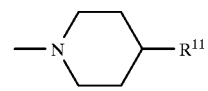

{wherein $R^{11}$ is a $C_{1-4}$ alkyl group (this alkyl group may be substituted by one or more substituents selected from a group of substituents consisting of a phenyl group which may be substituted by $Y^3$ (wherein $Y^3$ is as defined above) and a hydroxyl group)}.

Now, $R^1$, $R^2$, $R^3$, $R^4$, $R^5$, A, B, X, $Y^1$ and $Y^2$ in the compound of the formula (I) of the present invention will be described.

Specific examples of each of $R^1$, $R^2$ and $R^3$ include a hydrogen atom, a methyl group, an ethyl group, a n-propyl group, an i-propyl group, a n-butyl group, an i-butyl group, a sec-butyl group and a t-butyl group. A hydrogen atom is preferred for each of them.

A is an alkylene chain having a total carbon number of from 1 to 5 which may be substituted by a hydroxyl group or an alkyl group at any optional position and may, for example, be a bond species such as a methylene group, an ethylene group, a propylene group, a butylene group or a pentylene group. More preferred is a linear alkylene group having from 1 to 4 carbon atoms.

B may be a carbonyl group or a methylene chain bond species which may be substituted by a $C_{1-4}$ alkyl group.

X may be a chlorine atom or a bromine atom.

$Y^1$ may, for example, be a hydrogen atom, a chlorine atom, a bromine atom, an iodine atom, a nitro group, an amino group, a methoxy group, an ethoxy group, a n-propoxy group, an i-propoxy group, a n-butoxy group, an i-butoxy group, a sec-butoxy group or a t-butoxy group.

$Y^2$ may, for example, be a hydrogen atom, a chlorine atom, a bromine atom, an iodine atom, a hydroxyl group, a methyl group, an ethyl group, a n-propyl group, an i-propyl group, a n-butyl group, an i-butyl group, a secbutyl group, a t-butyl group, a methoxy group, an ethoxy group, a n-propoxy group, an i-propoxy group, a n-butoxy group, an i-butoxy group, a sec-butoxy group or a t-butoxy group.

$R^4$ and $R^5$ are as follows:

(1) Each of them is a $C_{1-4}$ alkyl group such as a methyl group, an ethyl group, a n-propyl group, an i-propyl group, a n-butyl group, an i-butyl group, a sec-butyl group or a t-butyl group.

(2) $R^4$ is a hydrogen atom, and $R^5$ is -Z-Ar (wherein Z is a $C_{1-5}$ alkylene chain, and Ar is an aromatic 6-membered ring which may contain one or two nitrogen atoms). The aromatic 6-membered ring includes a phenyl group, a 2-pyridyl group, a 3-pyridyl group, a 4-pyridyl group, a 3-pyridazinyl group, a 4-pyridazinyl group, a 2-pyrimidinyl group, a 4-pyrimidinyl group, a 5-pyrimidinyl group and a 2-pyrazinyl group.

(3) $R^4$ and $R^5$ together form a $C_{2-6}$ cyclic alkylene group, and they form together with the nitrogen atom to which they are bonded, an aziridine ring, an azetidine ring, a pyrrolidine ring, a piperidine ring or a homopiperidine ring.

(4) $R^4$ and $R^5$ form together with the adjacent nitrogen atom to which they are bonded, a 4-substituted piperazine ring of the formula:

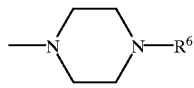

or a 4-substituted piperidine ring of the formula:

$R^6$ is a $C_{1-4}$ alkyl group or —$COR^{10}$ (wherein $R^{10}$ is a hydrogen atom or a $C_{1-4}$ alkyl group).

The $C_{1-4}$ alkyl group for $R^6$ is preferably a methyl group and may have a substituent. Such a substituent may, for example, be a $C_{1-4}$ alkyl group, a phenyl group which may be substituted by $Y^3$ (wherein $Y^3$ is a hydrogen atom, a halogen atom, a $C_{1-4}$ alkyl group, a $C_{1-4}$ alkoxy group, an amino group, an N-formyl group or a $C_{1-4}$ alkylcarbonylamino group),

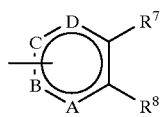

(wherein each of $R^7$ and $R^8$ is a hydrogen atom, or $R^7$ and $R^8$ form together with the carbon atoms to which they are respectively bonded, a benzene ring, and each of A, B, C and D which are independent of one another, is a nitrogen atom or a carbon atom) and

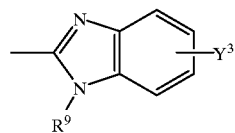

(wherein $Y^3$ is as defined above, and $R^9$ is a $C_{1-4}$ alkyl group or a benzyl group which may be substituted by a $C_{1-4}$ alkyl group, a $C_{1-4}$ alkoxy group or a halogen atom on the benzene ring). The number of such substituents may be one or more.

Specific examples of $R^6$ include a benzyl group which may have a halogen atom substituted at an optional position of the o-, m- or p-position on the benzene ring, an α,α-diphenylmethyl group, a pyridylmethyl group which may be substituted at an optional position of the 2-, 3- or 4-position, a pyrimidylmethyl group, a pyrazylmethyl group, a pyridazylmethyl group, a quinolylmethyl group, an isoquinolylmethyl group, a quinoxalylmethyl group, a quinazolylmethyl group, a benzimidazolylmethyl group having a benzyl group which may be substituted by a halogen atom on the benzene ring or by a $C_{1-4}$ alkyl group at the N-position, and a combination of such aromatic rings, such as an α,α-phenyl-pyridylmethyl group, an α,α-phenyl-pyrimidylmethyl group, an α,α-phenyl-pyrazylmethyl group, an α,α-phenyl-pyridazylmethyl group, an α,α-phenyl-quinolylmethyl group, an α,α-phenylisoquinolylmethyl group, an α,α-phenyl-quinoxalylmethyl group or an α,α-phenyl-quinazolylmethyl group.

$R^{11}$ is a $C_{1-4}$ alkyl group, and this alkyl group may have substituents. The substituents include two types i.e. a phenyl group which may be substituted by $Y^3$ (wherein $Y^3$ is as defined above) and a hydroxyl group. One of them or a plurality of each of them may be substituted.

Specific examples of $R^{11}$ include a benzyl group which may have a halogen atom substituted at an optional position of the o-, m- or p-position on the benzene ring, an α,α-diphenylmethyl group and an α,α,α-hydroxydiphenylmethyl group. Preferred examples for each of $R^4$ and $R^5$ include the 4-substituted piperazin-1-yl and 4-substituted piperidin-1-yl as described above.

In the foregoing description, n means normal, i iso, sec secondary, t tertiary, o ortho, m meta and p para.

The following compounds may be mentioned as preferred compounds among the compounds of the formula (I) of the present invention.

(1) A compound of the formula (I) wherein each of $R^2$ and $R^3$ is a hydrogen atom, and $Y^1$ is a hydrogen atom, a halogen atom, a nitro group or a $C_{1-4}$ alkoxy group.

(2) A compound of the formula (I) as defined in the above (1) wherein $R^4$ and $R^5$ form together with the adjacent nitrogen atom to which they are bonded, a 4-substituted piperazine ring of the formula:

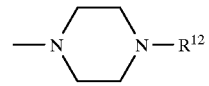

wherein $R^{12}$ is a $C_{1-4}$ alkyl group {this alkyl group may be substituted by one or more substituents selected from a group of substituents consisting of a $C_{1-4}$ alkyl group, a phenyl group which may be substituted by $Y^3$ (wherein $Y^3$ is a hydrogen atom, a halogen atom, a $C_{1-4}$ alkyl group, a $C_{1-4}$ alkoxy group, an amino group, an N-formyl group or a $C_{1-4}$ alkylcarbonylamino group),

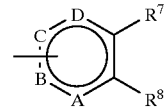

(wherein each of $R^7$ and $R^8$ is a hydrogen atom, or $R^7$ and $R^8$ form together with the carbon atoms to which they are bonded, a benzene ring, and each of A, B, C and D which are independent of one another, is a nitrogen atom or a carbon atom) and

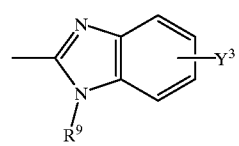

(wherein $Y^3$ is as defined above, and $R^9$ is a $C_{1-4}$ alkyl group or a benzyl group which may be substituted by a $C_{1-4}$ alkyl group, a $C_{1-4}$ alkoxy group or a halogen atom on the benzene ring)} or —COR$^{10}$ (wherein R$^{10}$ is a hydrogen atom or a C$_{1-4}$ alkyl group), or a 4-substituted piperidine ring of the formula:

wherein R$^{11}$ is a C$_{1-4}$ alkyl group {this alkyl group may be substituted by one or more substituents selected from a group of substituents consisting of a phenyl group which may be substituted by Y$^3$ (wherein Y$^3$ is as defined above) and a hydroxyl group}.

(3) A compound as defined in the above (2) wherein R$^4$ and R$^5$ form together with the adjacent nitrogen atom to which they are bonded, a 4-substituted piperazine ring of the formula:

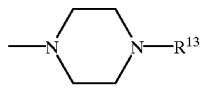

wherein R$^{13}$ is a methyl group {this methyl group may be substituted by one or more substituents selected from a group of substituents consisting of a phenyl group which may be substituted by Y$^3$ (wherein Y$^3$ is a hydrogen atom, a halogen atom, a C$_{1-4}$ alkyl group, a C$_{1-4}$ alkoxy group, an amino group, an N-formyl group or a C$_{1-4}$ alkylcarbonylamino group),

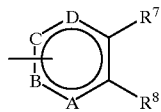

(wherein each of R$^7$ and R$^8$ is a hydrogen atom, or R$^7$ and R$^8$ form together with the carbon atoms to which they are bonded, a benzene ring, and each of A, B, C and D which are independent of one another, is a nitrogen atom or a carbon atom) and

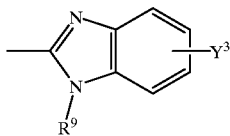

(wherein Y$^3$ is as defined above, and R$^9$ is a C$_{1-4}$ alkyl group or a benzyl group which may be substituted by a C$_{1-4}$ alkyl group, a C$_{1-4}$ alkoxy group or a halogen atom)} or —COR$^{10}$ (wherein R$^{10}$ is a hydrogen atom or a C$_{1-4}$ alkyl group).

(4) A compound as defined in the above (3), wherein Y$^2$ is a halogen atom or a C$_{1-4}$ alkoxy group.

(5) A compound as defined in the above (4), wherein R$^4$ and R$^5$ form together with the adjacent nitrogen atom to which they are bonded, a 4-substituted piperazine ring of the formula:

wherein R$^{14}$ is

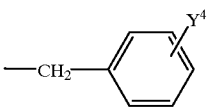

(wherein Y$^4$ is a hydrogen atom, a halogen atom, an amino group, an N-formyl group or a C$_{1-4}$ alkylcarbonylamino group),

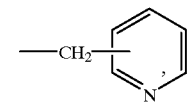

or

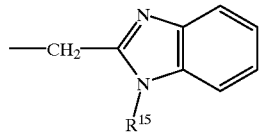

(wherein R$^{15}$ is a benzyl group which may be substituted by a halogen atom).

The compounds of the formula (I) include optical isomers and stereo isomers based on from 1 to 5 asymmetric carbon atoms.

The compounds of the formula (I) of the present invention can be converted to pharmaceutically acceptable non-toxic salts by means of appropriate acids, as the case requires. The compounds of the formula (I) can be used for the purpose of the present invention either in the free form or in the form of the pharmaceutically acceptable salts. The salts of such bases may, for example, be a mineral acid salt (such as a hydrochloride, a hydrobromide, a sulfate, a hydrogensulfate, a nitrate, a phosphate, a hydrogenphosphate or a dihydrogenphosphate), an organic acid salt (such as a formate, an acetate, a propionate, a succinate, a malonate, an oxalate, a maleate, a fumarate, a malate, a citrate, a tartarate, a lactate, a glutamate, an aspartate, a picrate or a carbonate) and a sulfonic acid salt (such as a methane sulfonate, benzene sulfonate or a toluene sulfonate). These salts may be prepared by conventional methods, respectively.

Now, typical examples of the 3-(2H)-pyridazinone derivative of the formula (I) and its pharmaceutically acceptable salt of the present invention will be given in Table I. However, it should be understood that the present invention is by no means restricted by such specific examples. In Table I, n means normal, i iso, t tertiary, Me a methyl group, Et an ethyl group, Pr a propyl group, Bu a butyl group, and Ph a phenyl group.

Q1 to Q42 in Table I are groups represented by the following formulas.

-continued
Q1 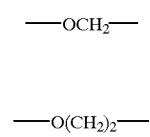
Q2 
Q3 
Q4 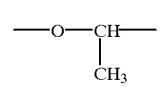
Q5 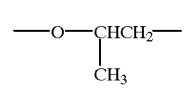
Q6 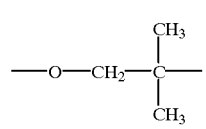
Q7 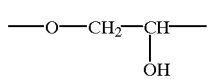
Q8 
Q9 
Q10 
Q11 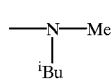
Q12 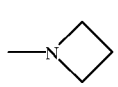
Q13 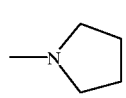
Q14 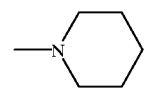
Q15 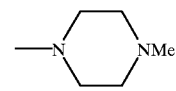
Q16 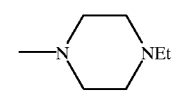
Q17 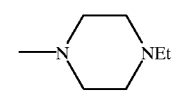
Q18 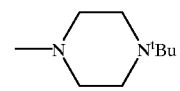
Q19 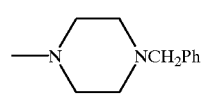
Q20 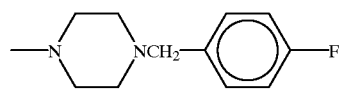
Q21 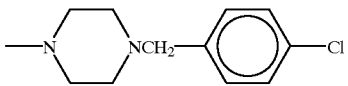
Q22 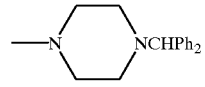
Q23 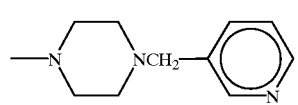
Q24 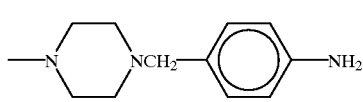
Q25 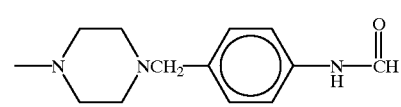

-continued

| | |
|---|---|
| Q26 | Q33 |
| Q27 | Q34 |
| Q28 | Q35 |
| Q29 | Q36 |
| Q30 | Q37 |
| Q31 | Q38 |
| | Q39 |
| | Q40 |
| | Q41 |
| Q32 | Q42 |

TABLE I

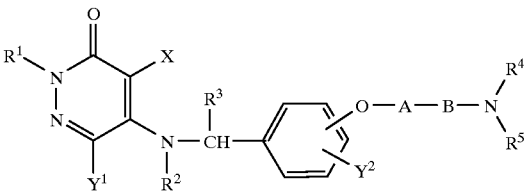

| No. | R¹ | R² | R³ | X | Y¹ | Y² | —O—A— | B | NR⁴R⁵ |
|---|---|---|---|---|---|---|---|---|---|
| 1 | H | H | H | Br | H | 4-OMe | 3-Q1 | CH₂ | Q10.HCl |
| 2 | H | H | H | Cl | Cl | 4-OMe | 3-Q1 | CH₂ | Q10.HCl |
| 3 | H | H | H | Cl | NO₂ | 4-OMe | 3-Q1 | CH₂ | Q10.HCl |
| 4 | H | H | H | Cl | H | 4-OMe | 3-Q1 | CH₂ | Q19.2HCl |
| 5 | H | H | H | Br | H | 4-OMe | 3-Q1 | CH₂ | Q19.2HCl |
| 6 | H | H | H | Br | H | 4-OMe | 3-Q1 | CH₂ | Q19.Q35 |
| 7 | H | H | H | Br | H | 4-OMe | 3-Q1 | CH₂ | Q21.2HCl |
| 8 | H | H | H | Br | H | 4-OMe | 3-Q1 | CH₂ | Q21.Q35 |
| 9 | H | H | H | Br | H | 4-OMe | 3-Q1 | CH₂ | Q21.H₂SO₄ |
| 10 | H | H | H | Cl | H | 4-OMe | 3-Q1 | CH₂ | Q21.2HCl |
| 11 | H | H | H | Cl | H | 4-OMe | 3-Q1 | CH₂ | Q21.H₂SO₄ |
| 12 | H | H | H | Cl | H | 4-OMe | 3-Q1 | CH₂ | Q21.Q35 |
| 13 | H | H | H | Br | H | 4-OMe | 3-Q1 | CH₂ | Q20.2HCl |
| 14 | H | H | H | Br | H | 4-OMe | 3-Q1 | CH₂ | Q20.Q35 |
| 15 | H | H | H | Cl | H | 4-OMe | 3-Q1 | CH₂ | Q20.2HCl |
| 16 | H | H | H | Cl | H | 4-OMe | 3-Q1 | CH₂ | Q20.Q35 |
| 17 | Et | H | H | Cl | H | 4-OMe | 3-Q1 | CH₂ | Q20.2HCl |
| 18 | H | H | H | Br | H | 4-OMe | 3-Q2 | CH₂ | Q10.HCl |
| 19 | H | H | H | Cl | Cl | 4-OMe | 3-Q2 | CH₂ | Q10.HCl |
| 20 | H | H | H | Cl | H | 4-OMe | 3-Q2 | CH₂ | Q16.2HCl |
| 21 | H | H | H | Cl | H | 4-OMe | 3-Q2 | CH₂ | Q17.2HCl |
| 22 | H | H | H | Br | H | 4-OMe | 3-Q2 | CH₂ | Q19.2HCl |
| 23 | H | H | H | Cl | H | 4-OMe | 3-Q2 | CH₂ | Q19.2HCl |
| 24 | H | H | H | Cl | NO₂ | 4-OMe | 3-Q2 | CH₂ | Q19.2HCl |
| 25 | H | H | H | Cl | Cl | 4-OMe | 3-Q2 | CH₂ | Q19.2HCl |
| 26 | H | H | H | Cl | H | 4-OMe | 3-Q2 | CH₂ | Q20.2HCl |
| 27 | Et | H | H | Cl | H | 4-OMe | 3-Q2 | CH₂ | Q20.2Q35 |
| 28 | ⁱPr | H | H | Cl | H | 4-OMe | 3-Q2 | CH₂ | Q20.2Q35 |
| 29 | H | H | H | Cl | NO₂ | 4-OMe | 3-Q2 | CH₂ | Q21.2HCl |
| 30 | H | H | H | Cl | Cl | 4-OMe | 3-Q2 | CH₂ | Q21.2HCl |
| 31 | H | H | H | Cl | H | 4-OMe | 3-Q1 | CO | Q37.HCl |
| 32 | H | H | H | Cl | H | 4-OMe | 3-Q1 | CO | Q16.HCl |
| 33 | H | H | H | Br | H | 4-OMe | 3-Q1 | CO | Q16.HCl |
| 34 | H | H | H | Br | H | 4-OMe | 3-Q1 | CO | Q23.2HCl |
| 35 | H | H | H | Cl | H | 4-OMe | 3-Q1 | CO | Q23.2HCl |
| 36 | H | H | H | Cl | H | 4-OMe | 3-Q1 | CO | Q19.Q35 |
| 37 | H | H | H | Cl | H | 4-OMe | 3-Q1 | CO | Q19.HCl |
| 38 | H | H | H | Br | H | 4-OMe | 3-Q1 | CO | Q19.Q35 |
| 39 | H | H | H | Cl | H | 4-OMe | 3-Q1 | CO | Q20.Q35 |
| 40 | H | H | H | Cl | H | 4-OMe | 3-Q1 | CO | Q20.HCl |
| 41 | Et | H | H | Cl | H | 4-OMe | 3-Q1 | CO | Q20.Q36 |
| 42 | ⁱPr | H | H | Cl | H | 4-OMe | 3-Q1 | CO | Q20.Q35 |
| 43 | H | H | H | Br | H | 4-OMe | 3-Q1 | CO | Q20.Q35 |
| 44 | H | H | H | Br | H | 4-OMe | 3-Q1 | CO | Q20.HCl |
| 45 | H | H | H | Cl | H | 4-OMe | 3-Q3 | CO | Q23.2HCl |
| 46 | H | H | H | Cl | H | 4-OMe | 3-Q3 | CO | Q16.HCl |
| 47 | H | H | H | Cl | H | 4-OMe | 3-Q3 | CO | Q19.HCl |
| 48 | H | H | H | Br | H | 4-OMe | 3-Q3 | CO | Q19.HCl |
| 49 | H | H | H | Cl | H | 4-OMe | 3-Q4 | CO | Q19.HCl |
| 50 | CONH₂ | H | H | Cl | H | 4-OMe | 3-Q1 | CO | Q20.Q35 |
| 51 | H | H | H | Cl | H | 4-OMe | 3-Q1 | CO | Q21.Q35 |
| 52 | H | H | H | Cl | H | 4-OMe | 3-Q5 | CO | Q20.Q35 |
| 53 | H | H | H | Cl | H | 4-OMe | 3-Q8 | CH₂ | Q20.2Q35 |
| 54 | H | H | H | Cl | H | 4-OMe | 3-Q2 | CH₂ | Q19.2Q35 |
| 55 | H | H | H | Cl | H | 4-OMe | 3-Q5 | CH₂ | Q20.2Q35 |
| 56 | H | H | H | Cl | H | 4-OMe | 3-Q7 | CO | Q20.Q35 |
| 57 | H | H | H | Cl | H | 4-OMe | 3-Q7 | CH₂ | Q20.2Q35 |
| 58 | H | H | H | Cl | H | 4-OMe | 3-Q8 | CH₂ | Q29.2Q35 |
| 59 | H | H | H | Cl | H | 4-OMe | 3-Q2 | CH₂ | Q29.2Q35 |
| 60 | H | H | H | Cl | H | 4-OMe | 3-Q2 | CH₂ | Q34.2Q35 |
| 61 | H | H | H | Cl | H | 4-OMe | 3-Q1 | CO | Q29.Q35 |
| 62 | H | H | H | Cl | H | 4-OMe | 3-Q1 | CO | Q27 |
| 63 | H | H | H | Cl | H | 4-OMe | 3-Q1 | CH₂ | Q27.Q35 |
| 64 | H | H | H | Cl | OEt | 4-OMe | 3-Q1 | CO | Q20.Q35 |
| 65 | H | H | H | Cl | OEt | 4-OMe | 3-Q1 | CH₂ | Q20.2Q35 |

TABLE I-continued (I)

$$R^1-N(-N=)-C(Y^1)=C(NR^2-CHR^3-\text{Ar}(Y^2)-O-A-B-NR^4R^5)-C(X)=C(=O)$$

| No. | R¹ | R² | R³ | X | Y¹ | Y² | —O—A— | B | NR⁴R⁵ |
|---|---|---|---|---|---|---|---|---|---|
| 66 | H | H | H | Cl | OEt | 4-OMe | 3-Q1 | CO | Q19.Q35 |
| 67 | H | H | H | Cl | OEt | 4-OMe | 3-Q1 | CO | Q29.Q36 |
| 68 | H | H | H | Cl | OEt | 4-OMe | 3-Q5 | CO | Q20.Q35 |
| 69 | H | H | H | Cl | OEt | 4-OMe | 3-Q7 | CO | Q20.Q35 |
| 70 | H | H | H | Cl | OEt | 4-OMe | 3-Q5 | CH₂ | Q29.2Q35 |
| 71 | H | H | H | Cl | OEt | 4-OMe | 3-Q2 | CH₂ | Q29.2Q35 |
| 72 | H | H | H | Cl | OEt | 4-OMe | 3-Q2 | CH₂ | Q34.2Q35 |
| 73 | H | H | H | Cl | OEt | 4-OMe | 3-Q1 | CO | Q34.Q35 |
| 74 | H | H | H | Cl | OEt | 4-OMe | 3-Q1 | CO | Q27 |
| 75 | H | H | H | Cl | OEt | 4-OMe | 3-Q1 | CH₂ | Q27.Q35 |
| 76 | H | H | H | Cl | OⁱPr | 4-OMe | 3-Q1 | CO | Q20.Q35 |
| 77 | H | H | H | Cl | OⁱPr | 4-OMe | 3-Q8 | CH₂ | Q25.2Q35 |
| 78 | H | H | H | Cl | OⁱPr | 4-OMe | 3-Q1 | CO | Q24 |
| 79 | H | H | H | Cl | OⁱPr | 4-OMe | 3-Q1 | CO | Q25.Q35 |
| 80 | H | H | H | Cl | OⁱPr | 4-OMe | 3-Q1 | CO | Q26.Q35 |
| 81 | H | H | H | Cl | H | 4-OMe | 3-Q3 | CH₂ | Q42 |
| 82 | H | H | H | Cl | H | 4-OMe | 3-Q1 | CH₂ | Q12.HCl |
| 83 | H | H | H | Cl | H | 4-OMe | 3-Q1 | CH₂ | Q14.HCl |
| 84 | H | H | H | Cl | H | 4-OMe | 3-Q1 | CH₂ | Q16.2HCl |
| 85 | H | H | H | Cl | H | 4-OMe | 3-Q1 | CH₂ | Q18.2HCl |
| 86 | H | H | H | Cl | H | 4-OMe | 3-Q1 | CH₂ | Q22.2HCl |
| 87 | H | H | H | Cl | H | 4-OMe | 3-Q1 | CH₂ | Q23.3HCl |
| 88 | H | H | H | Cl | H | 4-OMe | 3-Q1 | CH₂ | Q28.HCl |
| 89 | H | H | H | Cl | H | 4-OMe | 3-Q1 | CH₂ | Q37.2HCl |
| 90 | H | H | H | Cl | H | 4-OMe | 3-Q1 | CH₂ | Q39.HCl |
| 91 | H | H | H | Cl | H | 4-OMe | 3-Q1 | CH₂ | Q40.3HCl |
| 92 | H | H | H | Cl | H | 4-OMe | 3-Q1 | CH₂ | Q29.2HCl |
| 93 | H | H | H | Cl | H | 4-OMe | 3-Q1 | CH₂ | Q30.3HCl |
| 94 | H | H | H | Cl | H | 4-OMe | 3-Q1 | CH₂ | Q31.3HCl |
| 95 | H | H | H | Cl | H | 4-OMe | 3-Q1 | CH₂ | Q32.3HCl |
| 96 | H | H | H | Cl | H | 4-OMe | 3-Q1 | CH₂ | Q33.2HCl |
| 97 | H | H | H | Cl | H | 4-OMe | 3-Q1 | CH₂ | Q24.3HCl |
| 98 | H | H | H | Cl | H | 4-OMe | 3-Q1 | CH₂ | Q25.2HCl |
| 99 | H | H | H | Cl | H | 4-OMe | 3-Q1 | CH₂ | Q26.2HCl |
| 100 | H | H | H | Cl | H | 4-OMe | 3-Q1 | CH₂ | Q34.2HCl |
| 101 | H | H | H | Cl | H | 4-OMe | 3-Q2 | CH₂ | Q19.2HCl |
| 102 | H | H | H | Cl | H | 4-OMe | 3-Q2 | CH₂ | Q21.2HCl |
| 103 | H | H | H | Cl | H | 4-OMe | 3-Q2 | CH₂ | Q23.3HCl |
| 104 | H | H | H | Cl | H | 4-OMe | 3-Q2 | CH₂ | Q24.3HCl |
| 105 | H | H | H | Cl | H | 4-OMe | 3-Q2 | CH₂ | Q25.2HCl |
| 106 | H | H | H | Cl | H | 4-OMe | 3-Q2 | CH₂ | Q26.2HCl |
| 107 | H | H | H | Cl | H | 4-OMe | 3-Q2 | CH₂ | Q28.HCl |
| 108 | H | H | H | Cl | H | 4-OMe | 3-Q2 | CH₂ | Q29.3HCl |
| 109 | H | H | H | Cl | H | 4-OMe | 3-Q2 | CH₂ | Q33.2HCl |
| 110 | H | H | H | Cl | H | 4-OMe | 3-Q2 | CH₂ | Q34.2HCl |
| 111 | H | H | H | Cl | H | 4-OMe | 3-Q5 | CH₂ | Q10.HCl |
| 112 | H | H | H | Cl | H | 4-OMe | 3-Q5 | CH₂ | Q17.2HCl |
| 113 | H | H | H | Cl | H | 4-OMe | 3-Q5 | CH₂ | Q19.2HCl |
| 114 | H | H | H | Br | H | 4-OMe | 3-Q1 | CH₂ | Q11.HCl |
| 115 | Me | H | H | Br | H | 4-OMe | 3-Q1 | CH₂ | Q11.HCl |
| 116 | H | Me | H | Br | H | 4-OMe | 3-Q1 | CH₂ | Q11.HCl |
| 117 | H | H | H | Br | H | 4-OMe | 3-Q1 | CH₂ | Q17.2HCl |
| 118 | H | H | H | Br | NH₂ | 4-OMe | 3-Q1 | CH₂ | Q17.2HCl |
| 119 | H | H | H | Br | Br | 4-OMe | 3-Q1 | CH₂ | Q17.2HCl |
| 120 | H | H | H | Br | H | 4-Cl | 3-Q1 | CH₂ | Q19.2HCl |
| 121 | H | H | H | Br | H | H | 3-Q1 | CH₂ | Q20.2HCl |
| 122 | H | H | H | Br | H | 4-OEt | 3-Q1 | CH₂ | Q20.2HCl |
| 123 | H | H | H | Br | H | 4-OMe | 3-Q1 | CH₂ | Q22.2HCl |
| 124 | H | H | H | Br | H | 4-OMe | 3-Q1 | CH₂ | Q23.3HCl |
| 125 | H | H | H | Br | H | 4-OMe | 3-Q1 | CH₂ | Q38.2HCl |
| 126 | H | H | H | Br | H | 4-OMe | 3-Q1 | CH₂ | Q40.3HCl |
| 127 | H | H | H | Cl | H | 4-OMe | 3-Q2 | CH₂ | Q9.HCl |
| 128 | H | H | Me | Cl | H | 4-OMe | 3-Q2 | CH₂ | Q9.HCl |
| 129 | H | H | H | Cl | Cl | 4-OMe | 3-Q2 | CH₂ | Q9.HCl |
| 130 | tBu | H | H | Cl | H | 4-OMe | 3-Q2 | CH₂ | Q9.HCl |

TABLE I-continued $$(I)$$

(structure shown)

| No. | R¹ | R² | R³ | X | Y¹ | Y² | —O—A— | B | NR⁴R⁵ |
|---|---|---|---|---|---|---|---|---|---|
| 131 | H | H | H | Cl | H | 4-OH | 3-Q2 | CH₂ | Q9.HCl |
| 132 | H | H | H | Cl | H | 4-OMe | 3-Q2 | CH₂ | Q13.HCl |
| 133 | H | H | H | Cl | H | 4-OMe | 3-Q2 | CH₂ | Q14.HCl |
| 134 | H | H | H | Cl | H | 4-OMe | 3-Q2 | CH₂ | Q15.HCl |
| 135 | H | H | H | Cl | H | 4-OMe | 3-Q2 | CH₂ | Q28.HCl |
| 136 | H | H | H | Cl | H | 4-OMe | 3-Q2 | CH₂ | Q41.HCl |
| 137 | H | H | H | Br | H | 4-OMe | 3-Q2 | CH₂ | Q12.HCl |
| 138 | ⁱPr | H | H | Br | H | 4-OMe | 3-Q2 | CH₂ | Q14.HCl |
| 139 | H | H | H | Br | H | 4-Cl | 3-Q2 | CH₂ | Q14.HCl |
| 140 | H | H | H | Br | H | 4-OMe | 3-Q2 | CH₂ | Q18.2HCl |
| 141 | H | H | H | Br | H | 4-OMe | 3-Q2 | CH₂ | Q20.2HCl |
| 142 | H | H | H | Br | Br | 4-OMe | 3-Q2 | CH₂ | Q20.2HCl |
| 143 | H | Me | H | Br | H | 4-OMe | 3-Q2 | CH₂ | Q20.2HCl |
| 144 | H | H | H | Br | H | 4-OH | 3-Q2 | CH₂ | Q20.2HCl |
| 145 | H | H | H | Br | H | H | 3-Q2 | CH₂ | Q20.2HCl |
| 146 | H | H | H | Br | H | 4-OMe | 3-Q2 | CH₂ | Q21.2HCl |
| 147 | H | H | H | Br | H | 4-OMe | 2-Q2 | CH₂ | Q21.2HCl |
| 148 | H | H | H | Br | H | 4-OMe | 3-Q2 | CH₂ | Q23.3HCl |
| 149 | H | H | H | Cl | H | 4-OMe | 3-Q3 | CH₂ | Q10.HCl |
| 150 | H | H | H | Cl | Cl | 4-OMe | 3-Q3 | CH₂ | Q10.HCl |
| 151 | Et | H | H | Cl | H | 4-OMe | 3-Q3 | CH₂ | Q10.HCl |
| 152 | H | H | H | Cl | H | 4-OMe | 3-Q3 | CH₂ | Q13.HCl |
| 153 | H | H | H | Cl | H | 4-OMe | 3-Q3 | CH₂ | Q15.2HCl |
| 154 | H | H | H | Cl | H | 4-OEt | 3-Q3 | CH₂ | Q19.2HCl |
| 155 | H | H | H | Cl | H | 4-OMe | 3-Q3 | CH₂ | Q21.2HCl |
| 156 | H | H | H | Cl | H | 4-OMe | 3-Q3 | CH₂ | Q22.2HCl |
| 157 | H | H | H | Cl | H | 4-OMe | 3-Q3 | CH₂ | Q23.3HCl |
| 158 | H | H | H | Cl | H | 4-OMe | 3-Q3 | CH₂ | Q37.2HCl |
| 159 | H | H | H | Cl | H | 4-OMe | 3-Q3 | CH₂ | Q40.3HCl |
| 160 | H | H | H | Cl | H | 4-OMe | 3-Q3 | CH₂ | Q41.HCl |
| 161 | H | H | H | Br | H | 4-OMe | 3-Q4 | CH₂ | Q9.HCl |
| 162 | H | H | H | Br | H | 4-OMe | 3-Q4 | CH₂ | Q12.HCl |
| 163 | H | H | H | Br | H | 4-OMe | 3-Q4 | CH₂ | Q14.HCl |
| 164 | H | H | H | Br | H | 4-OMe | 3-Q4 | CH₂ | Q16.2HCl |
| 165 | H | H | H | Br | H | 4-OMe | 3-Q4 | CH₂ | Q20.2HCl |
| 166 | H | H | H | Br | H | 2-OMe | 3-Q4 | CH₂ | Q20.2HCl |
| 167 | H | H | H | Br | H | 4-OMe | 3-Q4 | CH₂ | Q28.HCl |
| 168 | H | H | H | Br | H | 4-OMe | 3-Q4 | CH₂ | Q39.HCl |
| 169 | H | H | H | Cl | H | 4-OMe | 3-Q5 | CH₂ | Q11.HCl |
| 170 | H | H | H | Cl | H | 4-OMe | 3-Q5 | CH₂ | Q13.HCl |
| 171 | H | H | H | Cl | H | 4-OMe | 3-Q5 | CH₂ | Q16.2HCl |
| 172 | H | H | H | Cl | H | 4-OMe | 3-Q5 | CH₂ | Q18.2HCl |
| 173 | H | H | H | Cl | H | 4-OMe | 3-Q5 | CH₂ | Q19.2HCl |
| 174 | H | H | H | Cl | H | 4-OMe | 3-Q5 | CH₂ | Q20.2HCl |
| 175 | H | H | H | Cl | H | 4-OEt | 3-Q5 | CH₂ | Q20.2HCl |
| 176 | H | H | H | Cl | H | 4-OⁱBu | 3-Q5 | CH₂ | Q20.2HCl |
| 177 | H | H | H | Cl | H | 4-OMe | 3-Q5 | CH₂ | Q23.3HCl |
| 178 | H | H | H | Br | H | 4-OMe | 3-Q6 | CH₂ | Q10.HCl |
| 179 | ⁱPr | H | H | Br | H | 4-OMe | 3-Q6 | CH₂ | Q14.HCl |
| 180 | H | H | H | Br | H | 4-OMe | 3-Q6 | CH₂ | Q17.2HCl |
| 181 | H | H | H | Br | H | 4-OMe | 3-Q6 | CH₂ | Q21.2HCl |
| 182 | H | H | H | Br | H | 4-OMe | 3-Q6 | CH₂ | Q39.HCl |
| 183 | H | H | H | Cl | H | 4-OMe | 3-Q1 | CO | Q10 |
| 184 | H | H | H | Cl | H | 4-OMe | 3-Q1 | CO | Q12 |
| 185 | H | H | H | Cl | H | 4-OMe | 3-Q1 | CO | Q14 |
| 186 | H | H | H | Cl | H | 4-OMe | 3-Q1 | CO | Q17.HCl |
| 187 | H | H | H | Cl | H | 4-OH | 3-Q1 | CO | Q20.HCl |
| 188 | H | H | H | Cl | H | 4-Cl | 3-Q1 | CO | Q20.HCl |
| 189 | H | H | H | Cl | NO₂ | 4-OMe | 3-Q1 | CO | Q20.HCl |
| 190 | H | H | H | Cl | H | 4-OMe | 3-Q1 | CO | Q21.HCl |
| 191 | H | H | H | Cl | H | 4-OMe | 3-Q1 | CO | Q23.2HCl |
| 192 | H | H | H | Cl | H | 4-OMe | 3-Q1 | CO | Q39 |
| 193 | H | H | H | Cl | H | 4-OMe | 3-Q1 | CO | Q41 |
| 194 | H | H | H | Br | H | 4-OMe | 3-Q1 | CO | Q11 |
| 195 | H | H | H | Br | H | 4-OMe | 3-Q1 | CO | Q13 |

TABLE I-continued (I)

| No. | R$^1$ | R$^2$ | R$^3$ | X | Y$^1$ | Y$^2$ | —O—A— | B | NR$^4$R$^5$ |
|-----|----|----|----|----|-----|-------|------|----|---------|
| 196 | Me | H | H | Br | H | 4-OMe | 3-Q1 | CO | Q16.HCl |
| 197 | H | H | H | Br | H | 4-Cl | 3-Q1 | CO | Q19.HCl |
| 198 | H | H | H | Br | H | 2-OMe | 3-Q1 | CO | Q19.HCl |
| 199 | H | H | H | Br | NO$_2$ | 4-OMe | 3-Q1 | CO | Q19.HCl |
| 200 | H | H | H | Br | NH$_2$ | 4-OMe | 3-Q1 | CO | Q19.HCl |
| 201 | H | H | H | Br | H | 4-OMe | 3-Q1 | CO | Q21.HCl |
| 202 | H | Me | H | Br | H | 4-OMe | 3-Q1 | CO | Q21.HCl |
| 203 | H | H | H | Br | H | 4-OEt | 3-Q1 | CO | Q21.HCl |
| 204 | H | H | H | Cl | H | 4-OMe | 3-Q2 | CO | Q10 |
| 205 | H | H | H | Cl | H | 4-OMe | 3-Q2 | CO | Q14 |
| 206 | H | H | H | Cl | H | 4-OMe | 3-Q2 | CO | Q17.HCl |
| 207 | H | H | H | Cl | H | 4-OMe | 3-Q2 | CO | Q19.HCl |
| 208 | H | H | H | Cl | H | 4-OMe | 3-Q2 | CO | Q20.HCl |
| 209 | H | H | H | Cl | H | 4-Cl | 3-Q2 | CO | Q20.HCl |
| 210 | H | H | H | Cl | H | H | 3-Q2 | CO | Q20.HCl |
| 211 | H | H | H | Cl | H | 4-F | 3-Q2 | CO | Q20.HCl |
| 212 | Et | H | H | Cl | H | 4-OMe | 3-Q2 | CO | Q20.HCl |
| 213 | H | H | H | Cl | H | 4-OMe | 3-Q2 | CO | Q21.HCl |
| 214 | H | H | H | Cl | NO$_2$ | 4-OMe | 3-Q2 | CO | Q21.HCl |
| 215 | H | H | H | Cl | Cl | 4-OMe | 3-Q2 | CO | Q21.HCl |
| 216 | Me | H | H | Cl | H | 4-OMe | 3-Q2 | CO | Q21.HCl |
| 217 | H | H | H | Cl | H | 4-OMe | 2-Q2 | CO | Q21.HCl |
| 218 | H | H | H | Cl | H | 4-OMe | 3-Q2 | CO | Q22.HCl |
| 219 | H | H | H | Br | H | 4-OMe | 3-Q2 | CO | Q9 |
| 220 | H | H | H | Br | H | 4-OMe | 3-Q2 | CO | Q15 |
| 221 | H | H | H | Br | H | 4-OMe | 3-Q2 | CO | Q18.HCl |
| 222 | H | H | H | Br | H | 4-OMe | 3-Q2 | CO | Q20.HCl |
| 223 | H | H | H | Br | H | 4-OMe | 3-Q2 | CO | Q23.2HCl |
| 224 | H | H | H | Br | H | 4-OMe | 3-Q2 | CO | Q28 |
| 225 | H | H | H | Br | H | 4-OMe | 3-Q2 | CO | Q37.HCl |
| 226 | H | H | H | Br | H | 4-OMe | 3-Q2 | CO | Q39 |
| 227 | H | H | H | Cl | H | 4-OMe | 3-Q3 | CO | Q11 |
| 228 | H | H | H | Cl | H | 4-OMe | 3-Q3 | CO | Q17.HCl |
| 229 | H | H | H | Cl | H | 4-OMe | 3-Q3 | CO | Q20.HCl |
| 230 | H | H | H | Cl | Cl | 4-OMe | 3-Q3 | CO | Q20.HCl |
| 231 | H | H | H | Cl | NH$_2$ | 4-OMe | 3-Q3 | CO | Q20.HCl |
| 232 | H | H | Me | Cl | H | 4-OMe | 3-Q3 | CO | Q20.HCl |
| 233 | H | H | H | Cl | Cl | 4-Cl | 3-Q3 | CO | Q20.HCl |
| 234 | H | H | H | Br | H | 4-OMe | 3-Q4 | CO | Q10 |
| 235 | H | H | H | Br | H | 4-OMe | 3-Q4 | CO | Q12 |
| 236 | H | H | H | Br | H | 4-OMe | 3-Q4 | CO | Q13 |
| 237 | H | H | H | Br | H | 4-OMe | 3-Q4 | CO | Q18.HCl |
| 238 | H | H | H | Br | H | 4-OMe | 3-Q4 | CO | Q19.HCl |
| 239 | H | H | H | Br | H | 4-OMe | 3-Q4 | CO | Q21.HCl |
| 240 | H | H | H | Br | H | 4-OMe | 3-Q4 | CO | Q23.2HCl |
| 241 | H | H | H | Br | H | 4-OMe | 3-Q4 | CO | Q38.HCl |
| 242 | H | H | H | Br | H | 4-OMe | 3-Q4 | CO | Q40.2HCl |
| 243 | H | H | H | Cl | H | 4-OMe | 3-Q5 | CO | Q9 |
| 244 | H | H | H | Cl | H | 4-OMe | 3-Q5 | CO | Q16.HCl |
| 245 | H | H | H | Cl | H | 4-OMe | 3-Q5 | CO | Q19.HCl |
| 246 | H | H | H | Cl | Cl | 4-OMe | 3-Q5 | CO | Q19.HCl |
| 247 | H | H | H | Cl | H | 4-O$^n$Bu | 3-Q5 | CO | Q19.HCl |
| 248 | H | H | H | Cl | H | 2-OMe | 3-Q5 | CO | Q19.HCl |
| 249 | H | H | H | Cl | H | 4-OMe | 3-Q5 | CO | Q20.HCl |
| 250 | H | H | H | Cl | H | 4-OMe | 3-Q5 | CO | Q21.HCl |
| 251 | H | H | H | Cl | NO$_2$ | 4-OMe | 3-Q5 | CO | Q21.HCl |
| 252 | H | H | H | Cl | H | 4-Cl | 3-Q5 | CO | Q21.HCl |
| 253 | Et | H | H | Cl | H | 4-OMe | 3-Q5 | CO | Q21.HCl |
| 254 | H | H | H | Cl | H | 4-OMe | 3-Q5 | CO | Q23.2HCl |
| 255 | H | H | H | Br | H | 4-OMe | 3-Q6 | CO | Q10 |
| 256 | H | H | H | Br | H | 4-OMe | 3-Q6 | CO | Q15 |
| 257 | H | H | H | Br | H | 4-OMe | 3-Q6 | CO | Q18.HCl |
| 258 | H | H | H | Br | H | 4-OMe | 3-Q6 | CO | Q19.HCl |
| 259 | H | H | H | Br | H | 4-OMe | 3-Q6 | CO | Q20.HCl |
| 260 | H | H | H | Br | Br | 4-OMe | 3-Q6 | CO | Q20.HCl |

TABLE I-continued (I)

$$\text{Structure with } R^1, R^2, R^3, R^4, R^5, X, Y^1, Y^2, A, B$$

| No. | R¹ | R² | R³ | X | Y¹ | Y² | —O—A— | B | NR⁴R⁵ |
|---|---|---|---|---|---|---|---|---|---|
| 261 | H | H | H | Br | NH₂ | 4-OMe | 3-Q6 | CO | Q20.HCl |
| 262 | H | H | H | Br | H | 4-OMe | 3-Q6 | CO | Q21.HCl |
| 263 | H | H | H | Br | H | 4-Cl | 3-Q6 | CO | Q21.HCl |
| 264 | ⁱBu | H | H | Cl | H | 4-OMe | 3-Q6 | CO | Q19.HCl |
| 265 | H | H | H | Cl | H | 4-OMe | 3-Q6 | CO | Q20.HCl |
| 266 | H | H | H | Cl | Cl | 4-OMe | 3-Q6 | CO | Q20.HCl |
| 267 | H | H | H | Cl | H | 4-OMe | 3-Q6 | CO | Q21.HCl |
| 268 | H | H | H | Cl | H | 4-OMe | 3-Q6 | CO | Q23.2HCl |
| 269 | H | H | H | Cl | H | 4-OMe | 3-Q6 | CO | Q37.HCl |
| 270 | H | H | H | Cl | H | 4-OMe | 3-Q6 | CO | Q41 |
| 271 | H | H | H | Cl | H | 4-OMe | 3-Q5 | CH₂ | Q21.2HCl |
| 272 | H | H | H | Cl | H | 4-OMe | 3-Q5 | CH₂ | Q23.3HCl |
| 273 | H | H | H | Cl | H | 4-OMe | 3-Q5 | CH₂ | Q24.3HCl |
| 274 | H | H | H | Cl | H | 4-OMe | 3-Q5 | CH₂ | Q25.2HCl |
| 275 | H | H | H | Cl | H | 4-OMe | 3-Q5 | CH₂ | Q26.2HCl |
| 276 | H | H | H | Cl | H | 4-OMe | 3-Q5 | CH₂ | Q27.2HCl |
| 277 | H | H | H | Cl | H | 4-OMe | 3-Q5 | CH₂ | Q28.HCl |
| 278 | H | H | H | Cl | H | 4-OMe | 3-Q5 | CH₂ | Q29.3HCl |
| 279 | H | H | H | Cl | H | 4-OMe | 3-Q5 | CH₂ | Q33.2HCl |
| 280 | H | H | H | Cl | H | 4-OMe | 3-Q5 | CH₂ | Q34.2HCl |
| 281 | H | H | H | Cl | H | 4-OMe | 3-Q7 | CH₂ | Q10.HCl |
| 282 | H | H | H | Cl | H | 4-OMe | 3-Q7 | CH₂ | Q17.2HCl |
| 283 | H | H | H | Cl | H | 4-OMe | 3-Q7 | CH₂ | Q19.2HCl |
| 284 | H | H | H | Cl | H | 4-OMe | 3-Q7 | CH₂ | Q21.2HCl |
| 285 | H | H | H | Cl | H | 4-OMe | 3-Q7 | CH₂ | Q23.3HCl |
| 286 | H | H | H | Cl | H | 4-OMe | 3-Q7 | CH₂ | Q24.3HCl |
| 287 | H | H | H | Cl | H | 4-OMe | 3-Q7 | CH₂ | Q25.2HCl |
| 288 | H | H | H | Cl | H | 4-OMe | 3-Q7 | CH₂ | Q26.2HCl |
| 289 | H | H | H | Cl | H | 4-OMe | 3-Q7 | CH₂ | Q27.HCl |
| 290 | H | H | H | Cl | H | 4-OMe | 3-Q7 | CH₂ | Q28.HCl |
| 291 | H | H | H | Cl | H | 4-OMe | 3-Q7 | CH₂ | Q29.3HCl |
| 292 | H | H | H | Cl | H | 4-OMe | 3-Q7 | CH₂ | Q33.2HCl |
| 293 | H | H | H | Cl | H | 4-OMe | 3-Q7 | CH₂ | Q34.2HCl |
| 294 | H | H | H | Cl | H | 4-OMe | 3-Q8 | CH₂ | Q10.HCl |
| 295 | H | H | H | Cl | H | 4-OMe | 3-Q8 | CH₂ | Q17.2HCl |
| 296 | H | H | H | Cl | H | 4-OMe | 3-Q8 | CH₂ | Q19.2HCl |
| 297 | H | H | H | Cl | H | 4-OMe | 3-Q8 | CH₂ | Q21.2HCl |
| 298 | H | H | H | Cl | H | 4-OMe | 3-Q8 | CH₂ | Q23.3HCl |
| 299 | H | H | H | Cl | H | 4-OMe | 3-Q8 | CH₂ | Q24.3HCl |
| 300 | H | H | H | Cl | H | 4-OMe | 3-Q8 | CH₂ | Q25.2HCl |
| 301 | H | H | H | Cl | H | 4-OMe | 3-Q8 | CH₂ | Q26.2HCl |
| 302 | H | H | H | Cl | H | 4-OMe | 3-Q8 | CH₂ | Q27.HCl |
| 303 | H | H | H | Cl | H | 4-OMe | 3-Q8 | CH₂ | Q28.HCl |
| 304 | H | H | H | Cl | H | 4-OMe | 3-Q8 | CH₂ | Q33.2HCl |
| 305 | H | H | H | Cl | H | 4-OMe | 3-Q8 | CH₂ | Q34.2HCl |
| 306 | H | H | H | Cl | H | 4-OMe | 3-Q1 | CO | Q24.HCl |
| 307 | H | H | H | Cl | H | 4-OMe | 3-Q1 | CO | Q25.2HCl |
| 308 | H | H | H | Cl | H | 4-OMe | 3-Q1 | CO | Q26.HCl |
| 309 | H | H | H | Cl | H | 4-OMe | 3-Q1 | CO | Q33.HCl |
| 310 | H | H | H | Cl | H | 4-OMe | 3-Q1 | CO | Q34.HCl |
| 311 | H | H | H | Cl | H | 4-OMe | 3-Q3 | CO | Q20.HCl |
| 312 | H | H | H | Cl | H | 4-OMe | 3-Q3 | CO | Q21.HCl |
| 313 | H | H | H | Cl | H | 4-OMe | 3-Q3 | CO | Q24.2HCl |
| 314 | H | H | H | Cl | H | 4-OMe | 3-Q3 | CO | Q25.HCl |
| 315 | H | H | H | Cl | H | 4-OMe | 3-Q3 | CO | Q26.HCl |
| 316 | H | H | H | Cl | H | 4-OMe | 3-Q3 | CO | Q27 |
| 317 | H | H | H | Cl | H | 4-OMe | 3-Q3 | CO | Q28 |
| 318 | H | H | H | Cl | H | 4-OMe | 3-Q3 | CO | Q29.2HCl |
| 319 | H | H | H | Cl | H | 4-OMe | 3-Q3 | CO | Q33.HCl |
| 320 | H | H | H | Cl | H | 4-OMe | 3-Q3 | CO | Q34.HCl |
| 321 | H | H | H | Cl | H | 4-OMe | 3-Q5 | CO | Q24.2HCl |
| 322 | H | H | H | Cl | H | 4-OMe | 3-Q5 | CO | Q25.HCl |
| 323 | H | H | H | Cl | H | 4-OMe | 3-Q5 | CO | Q26.HCl |
| 324 | H | H | H | Cl | H | 4-OMe | 3-Q5 | CO | Q27 |
| 325 | H | H | H | Cl | H | 4-OMe | 3-Q5 | CO | Q28 |

TABLE I-continued (I)

| No. | R¹ | R² | R³ | X | Y¹ | Y² | —O—A— | B | NR⁴R⁵ |
|---|---|---|---|---|---|---|---|---|---|
| 326 | H | H | H | Cl | H | 4-OMe | 3-Q5 | CO | Q29.2HCl |
| 327 | H | H | H | Cl | H | 4-OMe | 3-Q5 | CO | Q53.HCl |
| 328 | H | H | H | Cl | H | 4-OMe | 3-Q5 | CO | Q54.HCl |
| 329 | H | H | H | Cl | H | 4-OMe | 3-Q7 | CO | Q10 |
| 330 | H | H | H | Cl | H | 4-OMe | 3-Q7 | CO | Q16.HCl |
| 331 | H | H | H | Cl | H | 4-OMe | 3-Q7 | CO | Q19.HCl |
| 332 | H | H | H | Cl | H | 4-OMe | 3-Q7 | CO | Q21.HCl |
| 333 | H | H | H | Cl | H | 4-OMe | 3-Q7 | CO | Q23.2HCl |
| 334 | H | H | H | Cl | H | 4-OMe | 3-Q7 | CO | Q24.2HCl |
| 335 | H | H | H | Cl | H | 4-OMe | 3-Q7 | CO | Q25.2HCl |
| 336 | H | H | H | Cl | H | 4-OMe | 3-Q7 | CO | Q26.2HCl |
| 337 | H | H | H | Cl | H | 4-OMe | 3-Q7 | CO | Q27 |
| 338 | H | H | H | Cl | H | 4-OMe | 3-Q7 | CO | Q28 |
| 339 | H | H | H | Cl | H | 4-OMe | 3-Q7 | CO | Q29.2HCl |
| 340 | H | H | H | Cl | H | 4-OMe | 3-Q7 | CO | Q33.HCl |
| 341 | H | H | H | Cl | H | 4-OMe | 3-Q7 | CO | Q34.HCl |
| 342 | H | H | H | Cl | OEt | 4-OMe | 3-Q1 | CH₂ | Q10 |
| 343 | H | H | H | Cl | OEt | 4-OMe | 3-Q1 | CH₂ | Q16.HCl |
| 344 | H | H | H | Cl | OEt | 4-OMe | 3-Q1 | CH₂ | Q19.HCl |
| 345 | H | H | H | Cl | OEt | 4-OMe | 3-Q1 | CH₂ | Q21.HCl |
| 346 | H | H | H | Cl | OEt | 4-OMe | 3-Q1 | CH₂ | Q23.3HCl |
| 347 | H | H | H | Cl | OEt | 4-OMe | 3-Q1 | CH₂ | Q24.3HCl |
| 348 | H | H | H | Cl | OEt | 4-OMe | 3-Q1 | CH₂ | Q25.2HCl |
| 349 | H | H | H | Cl | OEt | 4-OMe | 3-Q1 | CH₂ | Q26.2HCl |
| 350 | H | H | H | Cl | OEt | 4-OMe | 3-Q1 | CH₂ | Q29.2HCl |
| 351 | H | H | H | Cl | OEt | 4-OMe | 3-Q1 | CH₂ | Q33.HCl |
| 352 | H | H | H | Cl | OEt | 4-OMe | 3-Q1 | CH₂ | Q34.HCl |
| 353 | H | H | H | Cl | OEt | 4-OMe | 3-Q2 | CH₂ | Q10 |
| 354 | H | H | H | Cl | OEt | 4-OMe | 3-Q2 | CH₂ | Q16.HCl |
| 355 | H | H | H | Cl | OEt | 4-OMe | 3-Q2 | CH₂ | Q19.HCl |
| 356 | H | H | H | Cl | OEt | 4-OMe | 3-Q2 | CH₂ | Q20.2HCl |
| 357 | H | H | H | Cl | OEt | 4-OMe | 3-Q2 | CH₂ | Q21.2HCl |
| 358 | H | H | H | Cl | OEt | 4-OMe | 3-Q2 | CH₂ | Q23.3HCl |
| 359 | H | H | H | Cl | OEt | 4-OMe | 3-Q2 | CH₂ | Q24.3HCl |
| 360 | H | H | H | Cl | OEt | 4-OMe | 3-Q2 | CH₂ | Q25.2HCl |
| 361 | H | H | H | Cl | OEt | 4-OMe | 3-Q2 | CH₂ | Q26.2HCl |
| 362 | H | H | H | Cl | OEt | 4-OMe | 3-Q2 | CH₂ | Q27.HCl |
| 363 | H | H | H | Cl | OEt | 4-OMe | 3-Q2 | CH₂ | Q28.HCl |
| 364 | H | H | H | Cl | OEt | 4-OMe | 3-Q2 | CH₂ | Q33.2HCl |
| 365 | H | H | H | Cl | OEt | 4-OMe | 3-Q5 | CH₂ | Q10 |
| 366 | H | H | H | Cl | OEt | 4-OMe | 3-Q5 | CH₂ | Q16.HCl |
| 367 | H | H | H | Cl | OEt | 4-OMe | 3-Q5 | CH₂ | Q19.HCl |
| 368 | H | H | H | Cl | OEt | 4-OMe | 3-Q5 | CH₂ | Q21.2HCl |
| 369 | H | H | H | Cl | OEt | 4-OMe | 3-Q5 | CH₂ | Q23.3HCl |
| 370 | H | H | H | Cl | OEt | 4-OMe | 3-Q5 | CH₂ | Q24.3HCl |
| 371 | H | H | H | Cl | OEt | 4-OMe | 3-Q5 | CH₂ | Q25.2HCl |
| 372 | H | H | H | Cl | OEt | 4-OMe | 3-Q5 | CH₂ | Q26.2HCl |
| 373 | H | H | H | Cl | OEt | 4-OMe | 3-Q5 | CH₂ | Q27.HCl |
| 374 | H | H | H | Cl | OEt | 4-OMe | 3-Q5 | CH₂ | Q28.HCl |
| 375 | H | H | H | Cl | OEt | 4-OMe | 3-Q5 | CH₂ | Q29.3HCl |
| 376 | H | H | H | Cl | OEt | 4-OMe | 3-Q5 | CH₂ | Q33.2HCl |
| 377 | H | H | H | Cl | OEt | 4-OMe | 3-Q5 | CH₂ | Q34.2HCl |
| 378 | H | H | H | Cl | OEt | 4-OMe | 3-Q7 | CH₂ | Q10 |
| 379 | H | H | H | Cl | OEt | 4-OMe | 3-Q7 | CH₂ | Q16.2HCl |
| 380 | H | H | H | Cl | OEt | 4-OMe | 3-Q7 | CH₂ | Q19.2HCl |
| 381 | H | H | H | Cl | OEt | 4-OMe | 3-Q7 | CH₂ | Q20.2HCl |
| 382 | H | H | H | Cl | OEt | 4-OMe | 3-Q7 | CH₂ | Q21.2HCl |
| 383 | H | H | H | Cl | OEt | 4-OMe | 3-Q7 | CH₂ | Q23.3HCl |
| 384 | H | H | H | Cl | OEt | 4-OMe | 3-Q7 | CH₂ | Q24.3HCl |
| 385 | H | H | H | Cl | OEt | 4-OMe | 3-Q7 | CH₂ | Q25.2HCl |
| 386 | H | H | H | Cl | OEt | 4-OMe | 3-Q7 | CH₂ | Q26.2HCl |
| 387 | H | H | H | Cl | OEt | 4-OMe | 3-Q7 | CH₂ | Q27.HCl |
| 388 | H | H | H | Cl | OEt | 4-OMe | 3-Q7 | CH₂ | Q28.HCl |
| 389 | H | H | H | Cl | OEt | 4-OMe | 3-Q7 | CH₂ | Q29.3HCl |
| 390 | H | H | H | Cl | OEt | 4-OMe | 3-Q7 | CH₂ | Q33.2HCl |

TABLE I-continued (I)

| No. | R¹ | R² | R³ | X | Y¹ | Y² | —O—A— | B | NR⁴R⁵ |
|---|---|---|---|---|---|---|---|---|---|
| 391 | H | H | H | Cl | OEt | 4-OMe | 3-Q7 | CH₂ | Q34.2HCl |
| 392 | H | H | H | Cl | OEt | 4-OMe | 3-Q8 | CH₂ | Q10 |
| 393 | H | H | H | Cl | OEt | 4-OMe | 3-Q8 | CH₂ | Q16.2HCl |
| 394 | H | H | H | Cl | OEt | 4-OMe | 3-Q8 | CH₂ | Q19.2HCl |
| 395 | H | H | H | Cl | OEt | 4-OMe | 3-Q8 | CH₂ | Q20.2HCl |
| 396 | H | H | H | Cl | OEt | 4-OMe | 3-Q8 | CH₂ | Q21.2HCl |
| 397 | H | H | H | Cl | OEt | 4-OMe | 3-Q8 | CH₂ | Q23.3HCl |
| 398 | H | H | H | Cl | OEt | 4-OMe | 3-Q8 | CH₂ | Q24.3HCl |
| 399 | H | H | H | Cl | OEt | 4-OMe | 3-Q8 | CH₂ | Q26.2HCl |
| 400 | H | H | H | Cl | OEt | 4-OMe | 3-Q8 | CH₂ | Q27.HCl |
| 401 | H | H | H | Cl | OEt | 4-OMe | 3-Q8 | CH₂ | Q28.HCl |
| 402 | H | H | H | Cl | OEt | 4-OMe | 3-Q8 | CH₂ | Q29.3HCl |
| 403 | H | H | H | Cl | OEt | 4-OMe | 3-Q8 | CH₂ | Q33.2HCl |
| 404 | H | H | H | Cl | OEt | 4-OMe | 3-Q8 | CH₂ | Q34.2HCl |
| 405 | H | H | H | Cl | OEt | 4-OMe | 3-Q1 | CO | Q10 |
| 406 | H | H | H | Cl | OEt | 4-OMe | 3-Q1 | CO | Q16.2HCl |
| 407 | H | H | H | Cl | OEt | 4-OMe | 3-Q1 | CO | Q21.2HCl |
| 408 | H | H | H | Cl | OEt | 4-OMe | 3-Q1 | CO | Q23.2HCl |
| 409 | H | H | H | Cl | OEt | 4-OMe | 3-Q1 | CO | Q24.3HCl |
| 410 | H | H | H | Cl | OEt | 4-OMe | 3-Q1 | CO | Q25.2HCl |
| 411 | H | H | H | Cl | OEt | 4-OMe | 3-Q1 | CO | Q26.2HCl |
| 412 | H | H | H | Cl | OEt | 4-OMe | 3-Q1 | CO | Q27 |
| 413 | H | H | H | Cl | OEt | 4-OMe | 3-Q1 | CO | Q28 |
| 414 | H | H | H | Cl | OEt | 4-OMe | 3-Q1 | CO | Q33.2HCl |
| 415 | H | H | H | Cl | OEt | 4-OMe | 3-Q3 | CO | Q10 |
| 416 | H | H | H | Cl | OEt | 4-OMe | 3-Q3 | CO | Q16.HCl |
| 417 | H | H | H | Cl | OEt | 4-OMe | 3-Q3 | CO | Q19.HCl |
| 418 | H | H | H | Cl | OEt | 4-OMe | 3-Q3 | CO | Q20.HCl |
| 419 | H | H | H | Cl | OEt | 4-OMe | 3-Q3 | CO | Q21.2HCl |
| 420 | H | H | H | Cl | OEt | 4-OMe | 3-Q3 | CO | Q23.2HCl |
| 421 | H | H | H | Cl | OEt | 4-OMe | 3-Q3 | CO | Q24.3HCl |
| 422 | H | H | H | Cl | OEt | 4-OMe | 3-Q3 | CO | Q25.2HCl |
| 423 | H | H | H | Cl | OEt | 4-OMe | 3-Q3 | CO | Q26.2HCl |
| 424 | H | H | H | Cl | OEt | 4-OMe | 3-Q3 | CO | Q27 |
| 425 | H | H | H | Cl | OEt | 4-OMe | 3-Q3 | CO | Q28 |
| 426 | H | H | H | Cl | OEt | 4-OMe | 3-Q3 | CO | Q29.3HCl |
| 427 | H | H | H | Cl | OEt | 4-OMe | 3-Q3 | CO | Q33.2HCl |
| 428 | H | H | H | Cl | OEt | 4-OMe | 3-Q3 | CO | Q34.2HCl |
| 429 | H | H | H | Cl | OEt | 4-OMe | 3-Q5 | CO | Q10 |
| 430 | H | H | H | Cl | OEt | 4-OMe | 3-Q5 | CO | Q16.HCl |
| 431 | H | H | H | Cl | OEt | 4-OMe | 3-Q5 | CO | Q19.HCl |
| 432 | H | H | H | Cl | OEt | 4-OMe | 3-Q5 | CO | Q21.2HCl |
| 433 | H | H | H | Cl | OEt | 4-OMe | 3-Q5 | CO | Q23.2HCl |
| 434 | H | H | H | Cl | OEt | 4-OMe | 3-Q5 | CO | Q24.3HCl |
| 435 | H | H | H | Cl | OEt | 4-OMe | 3-Q5 | CO | Q25.2HCl |
| 436 | H | H | H | Cl | OEt | 4-OMe | 3-Q5 | CO | Q26.2HCl |
| 437 | H | H | H | Cl | OEt | 4-OMe | 3-Q5 | CO | Q27 |
| 438 | H | H | H | Cl | OEt | 4-OMe | 3-Q5 | CO | Q28 |
| 439 | H | H | H | Cl | OEt | 4-OMe | 3-Q5 | CO | Q29.3HCl |
| 440 | H | H | H | Cl | OEt | 4-OMe | 3-Q5 | CO | Q33.2HCl |
| 441 | H | H | H | Cl | OEt | 4-OMe | 3-Q5 | CO | Q34.2HCl |
| 442 | H | H | H | Cl | OEt | 4-OMe | 3-Q7 | CO | Q10 |
| 443 | H | H | H | Cl | OEt | 4-OMe | 3-Q7 | CO | Q16.HCl |
| 444 | H | H | H | Cl | OEt | 4-OMe | 3-Q7 | CO | Q19.HCl |
| 445 | H | H | H | Cl | OEt | 4-OMe | 3-Q7 | CO | Q21.2HCl |
| 446 | H | H | H | Cl | OEt | 4-OMe | 3-Q7 | CO | Q23.2HCl |
| 447 | H | H | H | Cl | OEt | 4-OMe | 3-Q7 | CO | Q24.3HCl |
| 448 | H | H | H | Cl | OEt | 4-OMe | 3-Q7 | CO | Q25.2HCl |
| 449 | H | H | H | Cl | OEt | 4-OMe | 3-Q7 | CO | Q26.2HCl |
| 450 | H | H | H | Cl | OEt | 4-OMe | 3-Q7 | CO | Q27 |
| 451 | H | H | H | Cl | OEt | 4-OMe | 3-Q7 | CO | Q28 |
| 452 | H | H | H | Cl | OEt | 4-OMe | 3-Q7 | CO | Q29.3HCl |
| 453 | H | H | H | Cl | OEt | 4-OMe | 3-Q7 | CO | Q33.2HCl |
| 454 | H | H | H | Cl | OEt | 4-OMe | 3-Q7 | CO | Q34.2HCl |
| 455 | H | H | H | Cl | OⁱPr | 4-OMe | 3-Q1 | CO | Q10 |

TABLE I-continued (I)

| No. | R¹ | R² | R³ | X | Y¹ | Y² | —O—A— | B | NR⁴R⁵ |
|---|---|---|---|---|---|---|---|---|---|
| 456 | H | H | H | Cl | OⁱPr | 4-OMe | 3-Q1 | CO | Q17.2HCl |
| 457 | H | H | H | Cl | OⁱPr | 4-OMe | 3-Q1 | CO | Q19.2HCl |
| 458 | H | H | H | Cl | OⁱPr | 4-OMe | 3-Q1 | CO | Q20.2HCl |
| 459 | H | H | H | Cl | OⁱPr | 4-OMe | 3-Q1 | CO | Q21.2HCl |
| 460 | H | H | H | Cl | OⁱPr | 4-OMe | 3-Q1 | CO | Q23.2HCl |
| 461 | H | H | H | Cl | OⁱPr | 4-OMe | 3-Q1 | CO | Q24.2HCl |
| 462 | H | H | H | Cl | OⁱPr | 4-OMe | 3-Q1 | CO | Q25.2HCl |
| 463 | H | H | H | Cl | OⁱPr | 4-OMe | 3-Q1 | CO | Q26.2HCl |
| 464 | H | H | H | Cl | OⁱPr | 4-OMe | 3-Q1 | CO | Q27.HCl |
| 465 | H | H | H | Cl | OⁱPr | 4-OMe | 3-Q1 | CO | Q28.HCl |
| 466 | H | H | H | Cl | OⁱPr | 4-OMe | 3-Q1 | CO | Q29.3HCl |
| 467 | H | H | H | Cl | OⁱPr | 4-OMe | 3-Q1 | CO | Q33.2HCl |
| 468 | H | H | H | Cl | OⁱPr | 4-OMe | 3-Q1 | CO | Q34.2HCl |
| 469 | H | H | H | Cl | OⁱPr | 4-OMe | 3-Q2 | CO | Q10 |
| 470 | H | H | H | Cl | OⁱPr | 4-OMe | 3-Q2 | CO | Q17.2HCl |
| 471 | H | H | H | Cl | OⁱPr | 4-OMe | 3-Q2 | CO | Q19.2HCl |
| 472 | H | H | H | Cl | OⁱPr | 4-OMe | 3-Q2 | CO | Q20.2HCl |
| 473 | H | H | H | Cl | OⁱPr | 4-OMe | 3-Q2 | CO | Q21.2HCl |
| 474 | H | H | H | Cl | OⁱPr | 4-OMe | 3-Q2 | CO | Q23.2HCl |
| 475 | H | H | H | Cl | OⁱPr | 4-OMe | 3-Q2 | CO | Q24.2HCl |
| 476 | H | H | H | Cl | OⁱPr | 4-OMe | 3-Q2 | CO | Q25.2HCl |
| 477 | H | H | H | Cl | OⁱPr | 4-OMe | 3-Q2 | CO | Q26.2HCl |
| 478 | H | H | H | Cl | OⁱPr | 4-OMe | 3-Q2 | CO | Q27.HCl |
| 479 | H | H | H | Cl | OⁱPr | 4-OMe | 3-Q2 | CO | Q28.HCl |
| 480 | H | H | H | Cl | OⁱPr | 4-OMe | 3-Q2 | CO | Q29.3HCl |
| 481 | H | H | H | Cl | OⁱPr | 4-OMe | 3-Q2 | CO | Q33.2HCl |
| 482 | H | H | H | Cl | OⁱPr | 4-OMe | 3-Q2 | CO | Q34.2HCl |
| 483 | H | H | H | Cl | OⁱPr | 4-OMe | 3-Q5 | CO | Q10 |
| 484 | H | H | H | Cl | OⁱPr | 4-OMe | 3-Q5 | CO | Q17.2HCl |
| 485 | H | H | H | Cl | OⁱPr | 4-OMe | 3-Q5 | CO | Q19.2HCl |
| 486 | H | H | H | Cl | OⁱPr | 4-OMe | 3-Q5 | CO | Q20.2HCl |
| 487 | H | H | H | Cl | OⁱPr | 4-OMe | 3-Q5 | CO | Q21.2HCl |
| 488 | H | H | H | Cl | OⁱPr | 4-OMe | 3-Q5 | CO | Q23.2HCl |
| 489 | H | H | H | Cl | OⁱPr | 4-OMe | 3-Q5 | CO | Q24.2HCl |
| 490 | H | H | H | Cl | OⁱPr | 4-OMe | 3-Q5 | CO | Q25.2HCl |
| 491 | H | H | H | Cl | OⁱPr | 4-OMe | 3-Q5 | CO | Q26.2HCl |
| 492 | H | H | H | Cl | OⁱPr | 4-OMe | 3-Q5 | CO | Q27.HCl |
| 493 | H | H | H | Cl | OⁱPr | 4-OMe | 3-Q5 | CO | Q28.HCl |
| 494 | H | H | H | Cl | OⁱPr | 4-OMe | 3-Q5 | CO | Q29.3HCl |
| 495 | H | H | H | Cl | OⁱPr | 4-OMe | 3-Q5 | CO | Q33.2HCl |
| 496 | H | H | H | Cl | OⁱPr | 4-OMe | 3-Q5 | CO | Q34.2HCl |
| 497 | H | H | H | Cl | OⁱPr | 4-OMe | 3-Q7 | CO | Q10 |
| 498 | H | H | H | Cl | OⁱPr | 4-OMe | 3-Q7 | CO | Q17.2HCl |
| 499 | H | H | H | Cl | OⁱPr | 4-OMe | 3-Q7 | CO | Q19.2HCl |
| 500 | H | H | H | Cl | OⁱPr | 4-OMe | 3-Q7 | CO | Q20.2HCl |
| 501 | H | H | H | Cl | OⁱPr | 4-OMe | 3-Q7 | CO | Q21.2HCl |
| 502 | H | H | H | Cl | OⁱPr | 4-OMe | 3-Q7 | CO | Q23.2HCl |
| 503 | H | H | H | Cl | OⁱPr | 4-OMe | 3-Q7 | CO | Q24.2HCl |
| 504 | H | H | H | Cl | OⁱPr | 4-OMe | 3-Q7 | CO | Q25.2HCl |
| 505 | H | H | H | Cl | OⁱPr | 4-OMe | 3-Q7 | CO | Q26.2HCl |
| 506 | H | H | H | Cl | OⁱPr | 4-OMe | 3-Q7 | CO | Q27.HCl |
| 507 | H | H | H | Cl | OⁱPr | 4-OMe | 3-Q7 | CO | Q28.HCl |
| 508 | H | H | H | Cl | OⁱPr | 4-OMe | 3-Q7 | CO | Q29.3HCl |
| 509 | H | H | H | Cl | OⁱPr | 4-OMe | 3-Q7 | CO | Q33.2HCl |
| 510 | H | H | H | Cl | OⁱPr | 4-OMe | 3-Q7 | CO | Q34.2HCl |
| 511 | H | H | H | Cl | OⁱPr | 4-OMe | 3-Q8 | CO | Q10 |
| 512 | H | H | H | Cl | OⁱPr | 4-OMe | 3-Q8 | CO | Q17.2HCl |
| 513 | H | H | H | Cl | OⁱPr | 4-OMe | 3-Q8 | CO | Q19.2HCl |
| 514 | H | H | H | Cl | OⁱPr | 4-OMe | 3-Q8 | CO | Q20.2HCl |
| 515 | H | H | H | Cl | OⁱPr | 4-OMe | 3-Q8 | CO | Q21.2HCl |
| 516 | H | H | H | Cl | OⁱPr | 4-OMe | 3-Q8 | CO | Q23.2HCl |
| 517 | H | H | H | Cl | OⁱPr | 4-OMe | 3-Q8 | CO | Q24.2HCl |
| 518 | H | H | H | Cl | OⁱPr | 4-OMe | 3-Q8 | CO | Q26.2HCl |
| 519 | H | H | H | Cl | OⁱPr | 4-OMe | 3-Q8 | CO | Q27.HCl |
| 520 | H | H | H | Cl | OⁱPr | 4-OMe | 3-Q8 | CO | Q28.HCl |

TABLE I-continued (I)

$$R^1-N(-N=)-C(=O)-C(X)=C(R^3)-C(NR^2)-CH-C_6H_3(Y^2)-O-A-B-NR^4R^5$$
with $Y^1$ on the pyridazinone ring.

| No. | $R^1$ | $R^2$ | $R^3$ | X | $Y^1$ | $Y^2$ | —O—A— | B | $NR^4R^5$ |
|---|---|---|---|---|---|---|---|---|---|
| 521 | H | H | H | Cl | O$^i$Pr | 4-OMe | 3-Q8 | CO | Q29.3HCl |
| 522 | H | H | H | Cl | O$^i$Pr | 4-OMe | 3-Q8 | CO | Q33.2HCl |
| 523 | H | H | H | Cl | O$^i$Pr | 4-OMe | 3-Q8 | CO | Q34.2HCl |
| 524 | H | H | H | Cl | O$^i$Pr | 4-OMe | 3-Q1 | CO | Q10 |
| 525 | H | H | H | Cl | O$^i$Pr | 4-OMe | 3-Q1 | CO | Q17.HCl |
| 526 | H | H | H | Cl | O$^i$Pr | 4-OMe | 3-Q1 | CO | Q19.HCl |
| 527 | H | H | H | Cl | O$^i$Pr | 4-OMe | 3-Q1 | CO | Q21.HCl |
| 528 | H | H | H | Cl | O$^i$Pr | 4-OMe | 3-Q1 | CO | Q23.2HCl |
| 529 | H | H | H | Cl | O$^i$Pr | 4-OMe | 3-Q1 | CO | Q27 |
| 530 | H | H | H | Cl | O$^i$Pr | 4-OMe | 3-Q1 | CO | Q28 |
| 531 | H | H | H | Cl | O$^i$Pr | 4-OMe | 3-Q1 | CO | Q29.3HCl |
| 532 | H | H | H | Cl | O$^i$Pr | 4-OMe | 3-Q1 | CO | Q33.2HCl |
| 533 | H | H | H | Cl | O$^i$Pr | 4-OMe | 3-Q1 | CO | Q34.2HCl |
| 534 | H | H | H | Cl | O$^i$Pr | 4-OMe | 3-Q3 | CO | Q10 |
| 535 | H | H | H | Cl | O$^i$Pr | 4-OMe | 3-Q3 | CO | Q17.HCl |
| 536 | H | H | H | Cl | O$^i$Pr | 4-OMe | 3-Q3 | CO | Q19.HCl |
| 537 | H | H | H | Cl | O$^i$Pr | 4-OMe | 3-Q3 | CO | Q20.HCl |
| 538 | H | H | H | Cl | O$^i$Pr | 4-OMe | 3-Q3 | CO | Q21.HCl |
| 539 | H | H | H | Cl | O$^i$Pr | 4-OMe | 3-Q3 | CO | Q23.2HCl |
| 540 | H | H | H | Cl | O$^i$Pr | 4-OMe | 3-Q3 | CO | Q24.2HCl |
| 541 | H | H | H | Cl | O$^i$Pr | 4-OMe | 3-Q3 | CO | Q25.HCl |
| 542 | H | H | H | Cl | O$^i$Pr | 4-OMe | 3-Q3 | CO | Q26.HCl |
| 543 | H | H | H | Cl | O$^i$Pr | 4-OMe | 3-Q3 | CO | Q27 |
| 544 | H | H | H | Cl | O$^i$Pr | 4-OMe | 3-Q3 | CO | Q28 |
| 545 | H | H | H | Cl | O$^i$Pr | 4-OMe | 3-Q3 | CO | Q29.2HCl |
| 546 | H | H | H | Cl | O$^i$Pr | 4-OMe | 3-Q3 | CO | Q33.HCl |
| 547 | H | H | H | Cl | O$^i$Pr | 4-OMe | 3-Q3 | CO | Q34.HCl |
| 548 | H | H | H | Cl | O$^i$Pr | 4-OMe | 3-Q5 | CO | Q10 |
| 549 | H | H | H | Cl | O$^i$Pr | 4-OMe | 3-Q5 | CO | Q17.HCl |
| 550 | H | H | H | Cl | O$^i$Pr | 4-OMe | 3-Q5 | CO | Q19.HCl |
| 551 | H | H | H | Cl | O$^i$Pr | 4-OMe | 3-Q5 | CO | Q20.HCl |
| 552 | H | H | H | Cl | O$^i$Pr | 4-OMe | 3-Q5 | CO | Q21.HCl |
| 553 | H | H | H | Cl | O$^i$Pr | 4-OMe | 3-Q5 | CO | Q23.2HCl |
| 554 | H | H | H | Cl | O$^i$Pr | 4-OMe | 3-Q5 | CO | Q24.2HCl |
| 555 | H | H | H | Cl | O$^i$Pr | 4-OMe | 3-Q5 | CO | Q25.HCl |
| 556 | H | H | H | Cl | O$^i$Pr | 4-OMe | 3-Q5 | CO | Q26.HCl |
| 557 | H | H | H | Cl | O$^i$Pr | 4-OMe | 3-Q5 | CO | Q27 |
| 558 | H | H | H | Cl | O$^i$Pr | 4-OMe | 3-Q5 | CO | Q28 |
| 559 | H | H | H | Cl | O$^i$Pr | 4-OMe | 3-Q5 | CO | Q29.2HCl |
| 560 | H | H | H | Cl | O$^i$Pr | 4-OMe | 3-Q5 | CO | Q33.HCl |
| 561 | H | H | H | Cl | O$^i$Pr | 4-OMe | 3-Q5 | CO | Q34.HCl |
| 562 | H | H | H | Cl | O$^i$Pr | 4-OMe | 3-Q7 | CO | Q10 |
| 563 | H | H | H | Cl | O$^i$Pr | 4-OMe | 3-Q7 | CO | Q17.HCl |
| 564 | H | H | H | Cl | O$^i$Pr | 4-OMe | 3-Q3 | CO | Q19.HCl |
| 565 | H | H | H | Cl | O$^i$Pr | 4-OMe | 3-Q7 | CO | Q20.HCl |
| 566 | H | H | H | Cl | O$^i$Pr | 4-OMe | 3-Q7 | CO | Q21.HCl |
| 567 | H | H | H | Cl | O$^i$Pr | 4-OMe | 3-Q7 | CO | Q23.2HCl |
| 568 | H | H | H | Cl | O$^i$Pr | 4-OMe | 3-Q7 | CO | Q24.2HCl |
| 569 | H | H | H | Cl | O$^i$Pr | 4-OMe | 3-Q7 | CO | Q25.HCl |
| 570 | H | H | H | Cl | O$^i$Pr | 4-OMe | 3-Q7 | CO | Q26.HCl |
| 571 | H | H | H | Cl | O$^i$Pr | 4-OMe | 3-Q7 | CO | Q27 |
| 572 | H | H | H | Cl | O$^i$Pr | 4-OMe | 3-Q7 | CO | Q28 |
| 573 | H | H | H | Cl | O$^i$Pr | 4-OMe | 3-Q7 | CO | Q29.2HCl |
| 574 | H | H | H | Cl | O$^i$Pr | 4-OMe | 3-Q7 | CO | Q33.HCl |
| 575 | H | H | H | Cl | O$^i$Pr | 4-OMe | 3-Q7 | CO | Q34.HCl |

Now, methods for producing the compounds of the present invention will be described.

The 3(2H)-pyridazinone derivatives of the formula (I) and their pharmaceutically acceptable salts of the present invention can be produced, for example, by the methods represented by the following reaction formulas (1) to (7).

Reaction Formula (1)

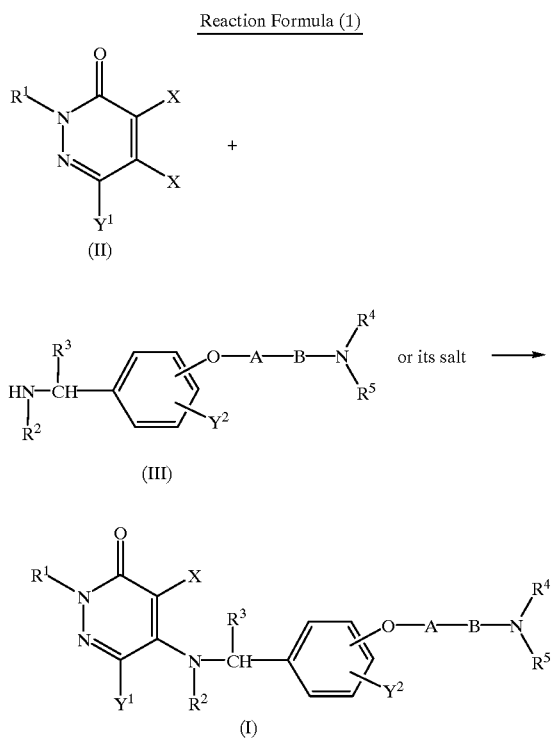

wherein $R^1, R^2, R^3, R^4, R^5, X, Y^1, Y^2$, A and B are as defined above.

The production method according to the reaction formula (1) is a method in which a 4,5-dihalo-3(2H)-pyridazinone compound of the formula (II) and a ω-aminoalkyleneoxy- or ω-aminocarbonylalkyleneoxy-substituted benzylamine derivative of the formula (III) or its salt are reacted optionally in the presence of a dehydrohalogenating agent in an inert solvent to produce the compound of the formula (I) of the present invention.

In the above reaction formula (1), a position isomer of the compound of the formula (I) i.e. a compound of the formula (IV) having an oxybenzylamino group substituted at the 4-position:

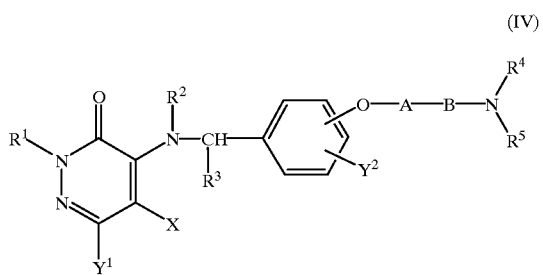

wherein $R^1, R^2, R^3, R^4, R^5, X, Y^1, Y^2$, A and B are as defined above, will form as a by-product. The production ratios of the compounds of the formulas (I) and (IV) depend primarily on the polarity of the solvent used.

Namely, when a solvent of high polarity is used, the production ratio of the compound of the formula (I) of the present invention tends to be high. Accordingly, as a solvent suitable for efficiently producing the compound of the formula (I) of the present invention while suppressing side-reaction for the production of the compound of the formula (IV), an ether type solvent (such as tetrahydrofuran or 1,4-dioxane), an amide type solvent (such as formamide, N,N-dimethylformamide, N,N-dimethylacetamide or N-methylpyrrolidone), acetonitrile, dimethylsulfoxide, an alcohol type solvent (such as methanol, ethanol or propanol), an organic amine type solvent (such as pyridine, triethylamine, N,N-dimethylaminoethanol or triethanolamine) or water, or a solvent mixture thereof, may be mentioned. For separation and purification of the compound of the formula (I) of the present invention from the above mixture of the compound of the formula (I) and the compound of the formula (IV), conventional methods per se known in organic syntheses, such as fractional recrystallization or various chromatography employing silica gel, may be employed.

During the reaction between the compound of the formula (II) and the compound of the formula (III), hydrogen chloride or hydrogen bromide is generated. It is usually possible to improve the yield by adding to the reaction system a dehydrohalogenating agent which traps such a hydrogen halide.

Any dehydrohalogenating agent may be used so long as it does not adversely affect the reaction and is capable of trapping a hydrogen halide. As such a dehydrohalogenating agent, an inorganic base such as potassium carbonate, sodium carbonate, potassium hydrogen carbonate, or sodium hydrogen carbonate, or an organic base such as N,N-dimethylaniline, N,N-diethylaniline, trimethylamine, triethylamine, N,N-dimethylaminoethanol, N-methylmorpholine, pyridine or 2,6-dimethyl-4-N,N-dimethylaminopyridine, may be mentioned.

Otherwise, the starting material benzylamine derivative of the formula (III) may be used in an excessive amount as the dehydrohalogenating agent. This gives an improved yield in many cases.

The reaction temperature may be usually within a range of from 10° C. to the boiling point of the solvent used for the reaction.

The molar ratio of the starting materials may optionally be set. However, the benzylamine derivative of the formula (III) or its salt may be used usually in an amount of from 1 to 10 mols, preferably from 1.2 to 5 mols, relative to one mol of the 4,5-dihalo-3(2H)-pyridazinone derivative of the formula (II).

The 4,5-dihalo-3(2H)-pyridazinone derivative of the formula (II) can be produced, for example, by utilizing or applying a conventional organic reaction or the following conventional production method. Namely, the one wherein the substituent $Y^1$ at the 6-position is a hydrogen atom, can be prepared by the method disclosed in reference (a) and (b), and the one wherein the substituent $Y^1$ is a halogen atom, a nitro group, an amino group or an alkoxy group, can be prepared by the method disclosed in reference (c).

The ω-aminoalkyleneoxy- or ω-aminocarbonylalkyleneoxy-substituted benzylamine derivative of the formula (III) or its salt in the reaction formula (1) can be produced, for example, by methods of the following reaction schemes (A) to (E) by utilizing or applying the methods disclosed in reference (a).

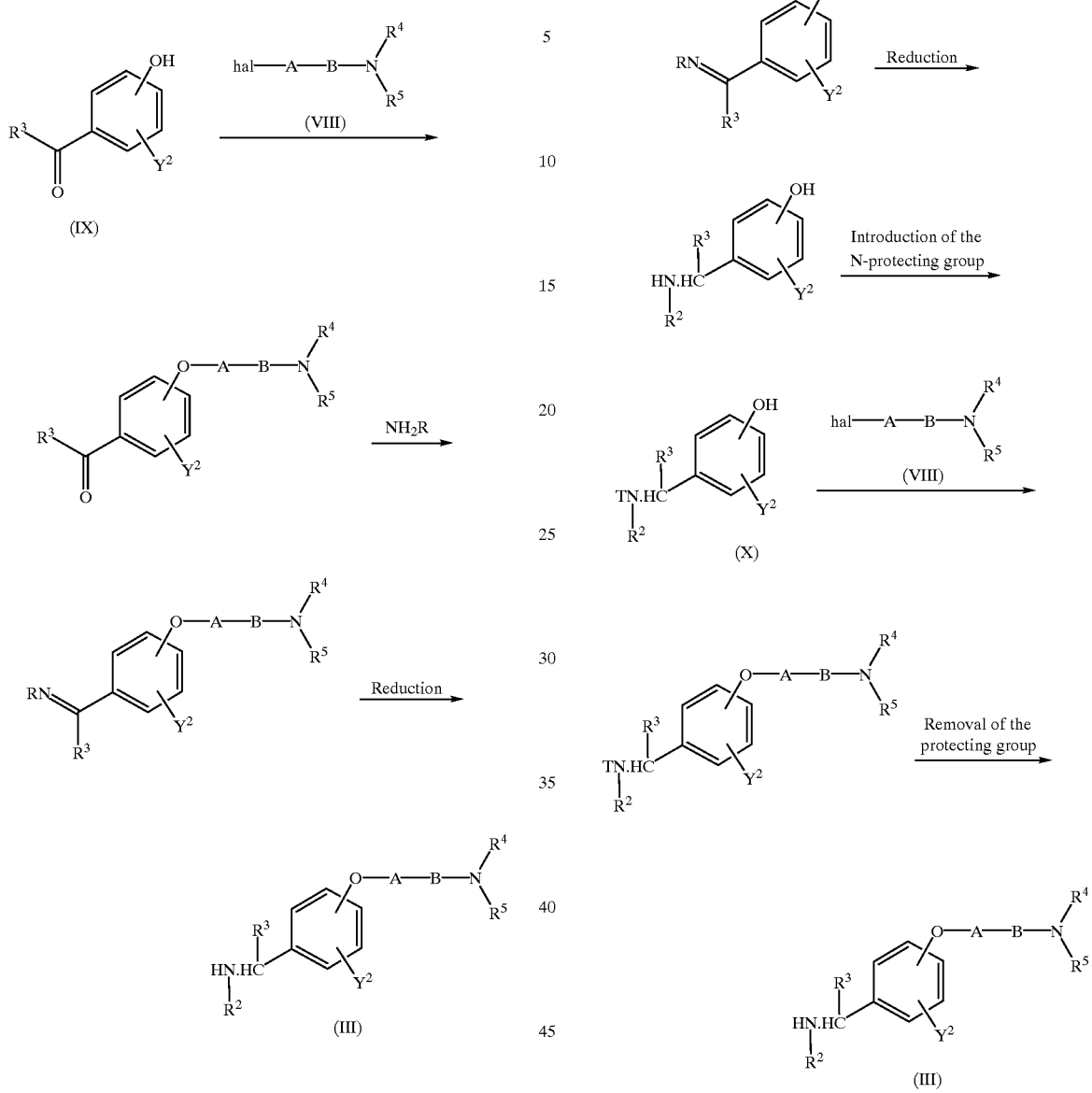

wherein hal is a leaving group such as a chlorine atom, a bromine atom, an iodine atom, a methanesulfonyloxy group or a p-toluenesulfonyloxy group, R is a hydrogen atom, a hydroxyl group, a $C_{1-4}$ alkyl group or a $C_{1-4}$ alkoxy group, and $R^2$, $R^3$, $R^4$, $R^5$, $Y^2$, A and B are as defined above.

wherein T is an amino-protecting group such as a benzyloxycarbonyl group, a t-butoxycarbonyl group, a formyl group, an acetyl group, a benzoyl group, a methoxycarbonyl group or an ethoxycarbonyl group, and $R^2$, $R^3$, $R^4$, $R^5$, $Y^2$, A, B, R and hal are as defined above.

Scheme (B)

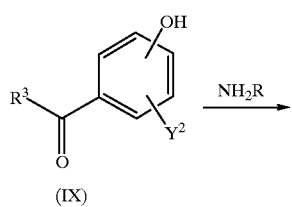

Scheme (C)

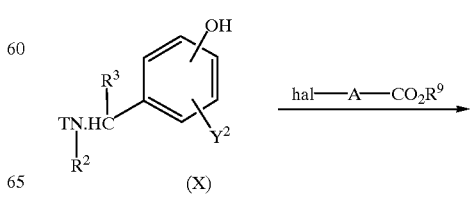

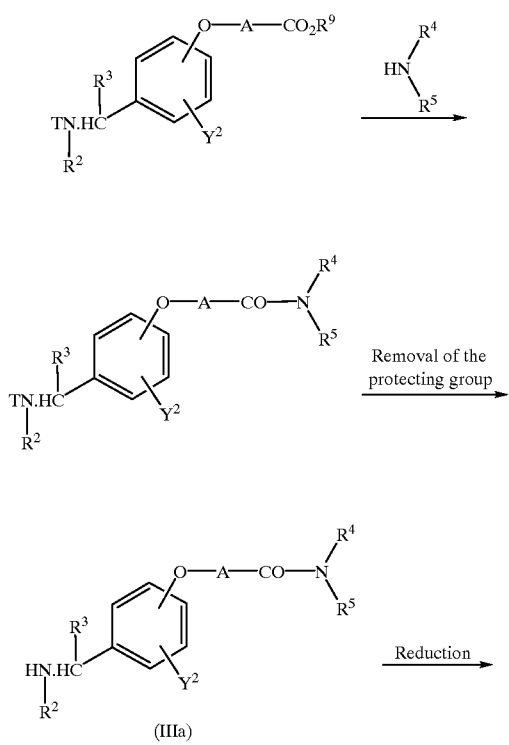

(IIIa)

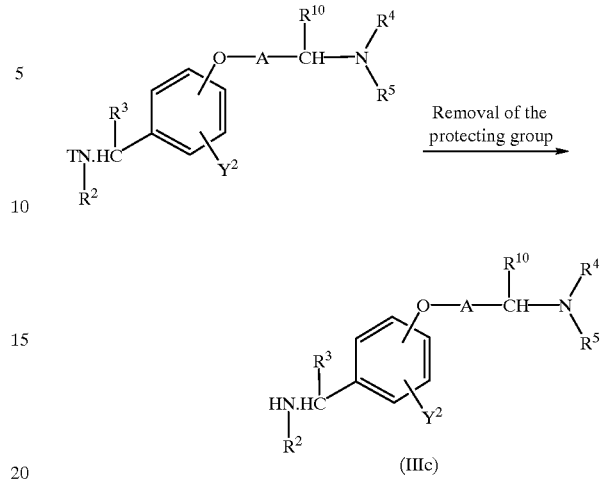

(IIIc)

wherein $R^{10}$ is a hydrogen atom or a $C_{1-4}$ alkyl group, hal is a leaving group within the same scope as hal defined in the above reaction scheme (A), but it is a substituent having the same or low leaving property as compared with hal in the particular combination, and $R^2$, $R^3$, $R^4$, $R^5$, $Y^2$, A, T and hal are as defined above.

Scheme (E)

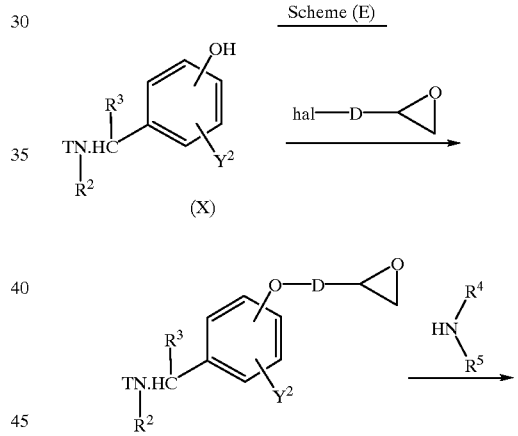

(X)

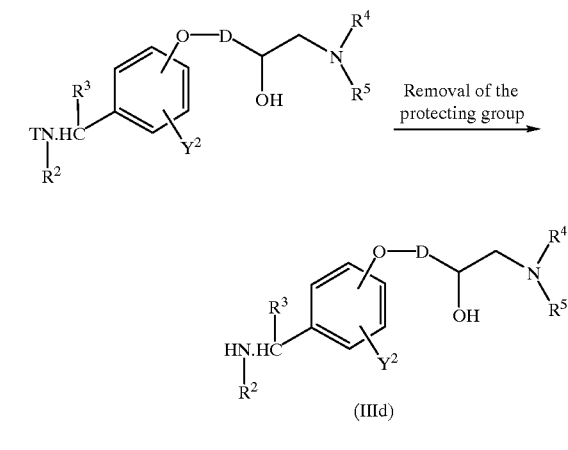

(IIId)

wherein $R^9$ is a hydrogen atom or a lower alkyl group, and $R^2$, $R^3$, $R^4$, $R^5$, $Y^2$, A, T and hal are as defined above.

Scheme (D)

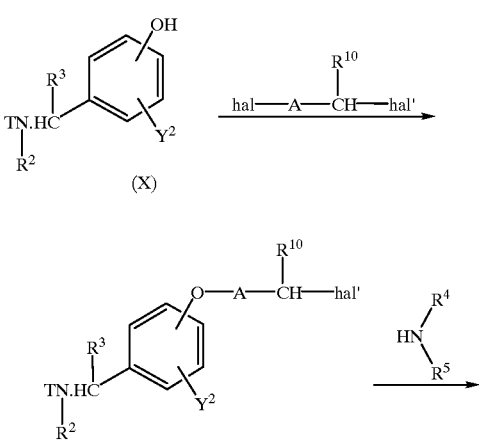

(X)

wherein D is a $C_{1-4}$ alkylene group, and $R^2$, $R^3$, $R^4$, $R^5$, $Y^2$ and hal are as defined above.

Reaction scheme (A) illustrates a method wherein a hydroxycarbonyl derivative (IX) is used as the starting material, and firstly a compound of the formula (VIII) is reacted to the phenol site to introduce the corresponding alkoxy side chain, and then the carbonyl site is converted to an amino group by reduction. Whereas, reaction scheme (B) illustrates a production method wherein this order in reaction scheme (A) is reversed. Reaction scheme (C) illustrates a method wherein the N-protected hydroxybenzylamine derivative of the formula (X) as an intermediate of the production route of scheme (B) is used as the starting material, and the side chain of the phenol site thereof is stepwise extended, and from the ω-aminocarbonylalkyleneoxybenzylamine derivative of the formula (IIIa), its reduced product of the formula (IIIb) having the amide bond site of the formula (IIIa) reduced, is produced. Reaction scheme (D) illustrates a method for producing a ω-aminoalkyleneoxybenzylamine derivative of the formula (IIIc) containing a branched methylene chain wherein B is substituted by a lower alkyl group, among benzylamine derivatives of the formula (III). Reaction scheme (E) illustrates a method for producing a compound of the formula (IIId) wherein A is a methylene chain having a hydroxyl group, among the benzylamine derivatives of the formula (III).

Using a readily available commercial starting material or a starting material produced therefrom, an appropriate method may be selected for use among the methods (A) to (E).

For the reaction of the hydroxycarbonyl derivative (IX) with (VIII) in scheme (A), conditions commonly employed for alkylating phenols may widely be used. Usually, this reaction proceeds relatively swiftly by using an inorganic base such as sodium carbonate, potassium carbonate, sodium hydroxide, potassium hydroxide, sodium hydrogencarbonate or potassium hydrogencarbonate in a ketone type solvent (such as acetone, methyl ethyl ketone or diethyl ketone), an amide type solvent (formamide, N,N-dimethylformamide, N,N-dimethylacetamide or N-methylpyrrolidone), an alcohol type solvent (such as methanol, ethanol or n-propanol) or water, or a solvent mixture thereof under heating to a temperature of from 40 to 150° C.

The subsequent reaction for conversion of the carbonyl group (the formyl group or the ketone group) to an aminomethyl group can be accomplished by subjecting a various amine of the formula $RNH_2$ to a condensation reaction to obtain an imino compound and then reducing this imino compound. In this method, this imino compound may not be isolated and may be formed in the reaction system and continuously subjected to the subsequent reduction reaction. Such a method may be rather advantageous in many cases from the viewpoint of the yield or economy.

Here, production of a primary amine wherein $R^2$ is a hydrogen atom among the benzylamine derivatives of the formula (III), can be accomplished by using an amine such as ammonia, hydroxylamine or O-alkylhydroxylamine as $RNH_2$ and reducing an imine thereby obtained.

For such a reduction, a hydrogenation reaction is widely used wherein Raney nickel, palladium-carbon or the like is used as the catalyst. Here, when an imine compound produced with the O-alkylhydroxylamine is used, the reaction can be conducted by using a metal hydride such as sodium trifluoroacetoxyborohydride [$NaBH_3(OCOCF_3)$] or sodium bis-methoxyethoxyaluminumhydride [$NaAlH_2(OCH_2CH_2OCH_3)_2$] (Chemical and Pharmaceutical Bulletin, vol. 26, p. 2897–2898, 1978).

The latter reduction method employing a metal hydride may sometimes be advantageous for producing a compound containing in $Y^2$ and $R^4$ or $R^5$ a halogen atom or a benzyl group which is relatively unstable under the hydrogenation reduction conditions, among the benzylamine derivatives of the formula (III). Whereas, for the production of a secondary amine wherein $R^2$ is a $C_{1-4}$ alkyl group among the benzylamine derivatives of the formula (III), the corresponding primary alkylamine of the formula $R_2NH_2$ may be used as $RNH_2$, and then in the reduction of an imine derivative obtainable by this condensation reaction, not only the reducing agent described with respect to the above method for producing a primary amine but also a much milder metal hydrogenation reducing agent such as sodium borohydride or sodium cyanoborohydride ($NaCNBH_3$) may be added as a reducing agent which can be suitably and most widely employed.

Reaction scheme (B) is a production route to obtain a benzylamine of the formula (III) by reversely carrying out the reaction steps in reaction scheme (A). Accordingly, the conversion of the carbonyl group to an aminomethyl group and the alkylation reaction of the phenol site can be conducted under the respective reaction conditions of the production method described with respect to scheme (A). According to this route, a step of introducing a protecting group for a benzylaminonitrogen atom is required in the process. As the protecting group of the formula T to be used here, it is possible to employ a wide range of protecting groups for amino groups which are commonly used for usual peptide syntheses, such as a benzyloxycarbonyl group, a t-butoxycarbonyl group, a formyl group, an acetyl group, a benzoyl group, a methoxycarbonyl group and an ethoxycarbonyl group. There is no strict limitation for the selection of a protecting group from such various protecting groups. However, in some cases, it will be necessary to properly select the protecting group to be employed or the conditions for removing it, depending upon the types of the substituents $Y^2$, B, $R^4$ and $R^5$. For example, to produce a compound containing in $Y^2$ or $R^4$ and $R^5$ a halogen atom or a benzyl group in the benzylamine (III), in some cases, it will be necessary to properly select the substituents and the reaction conditions so that the reaction for removing the protecting group can be efficiently and selectively proceeded even by a method other than catalytic hydrogenation. To produce a benzylamine of the formula (III) wherein B is a carbonyl chain, a benzyloxycarbonyl group or a t-butoxycarbonyl group is preferably employed in many cases, since removal of the protecting group can thereby be facilitated under a non-hydrolyzing condition. Conventional reaction conditions may be employed as the reaction conditions for the above-mentioned introduction of various protecting groups and removal of such protecting groups.

Reaction scheme (C) illustrates a method wherein using a hydroxybenzylamine of the formula (X) protected by a protecting group T as a starting material, the ether side chain is stepwise extended to obtain a compound of the formula (IIIa) wherein B is a carbonyl chain and a compound of the formula (IIIb) wherein B is a linear methylene chain obtained by reducing the carbonyl site, among benzylamines of the formula (III). In the reaction for forming an amide bond at the ether side chain site, when $R^9$ is a hydrogen atom, dehydration condensation methods which are commonly used for peptide syntheses can be widely employed. When an amine relatively rich in nucleophilic nature is employed, it is possible to use an ester wherein $R^9$ is a lower alkyl group, and in such a case, it is usually possible to employ a condition of heating in an inert solvent. As a reducing agent to be used for producing a benzylamine of the formula (IIIb), a metal hydride reducing agent such as lithium aluminum hydride, may be mentioned. The alkylation of the phenol site and the reaction for removing the protecting group in other steps can be conducted under the respective corresponding reactions in schemes (A) and (B).

Reaction scheme (D) provides a method for producing an aminoalkyleneoxybenzylamine derivative of the formula (IIIc) wherein the α-carbon of the amino group at the terminal of the phenol side chain is a linear or lower alkyl-substituted methylene chain. For the step of introducing the amino group moiety, conventional reaction conditions commonly employed in the substitution reaction of an alkylamine with an alkyl halide, may be employed.

Reaction scheme (E) is designed to introduce a hydroxyl group to the phenol side chain in the formula (IIId) and provides a method wherein an epoxy group is introduced to the phenol side chain by the reaction with various epoxyalkylhalide compounds, and a compound of the formula (IIId) is produced by the reaction with various amines.

Reaction formula (2)

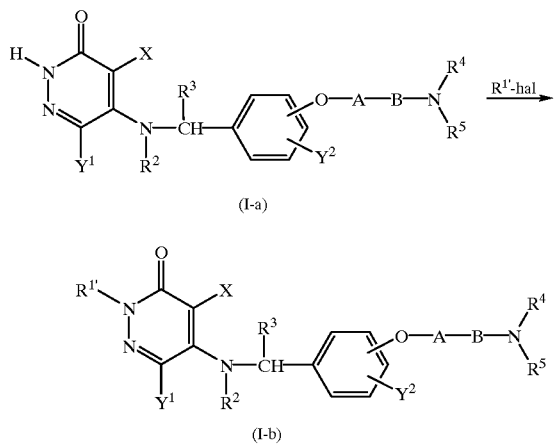

wherein $R^{1'}$ is a $C_{1-4}$ alkyl group, hal is a chlorine atom, a bromine atom or an iodine atom, and $R^2$, $R^3$, $R^4$, $R^5$, X, $Y^1$, $Y^2$, A and B are as defined above.

The reaction formula (2) illustrates a method for producing the 2-position substituted pyridazinone product of the formula (I-b) as a compound of the present invention, by reacting a compound of the formula (I-a) which is a compound of the formula (I) of the present invention wherein the 2-position of pyridazinone is a hydrogen atom, with a halogeno derivative of the formula $R^{1'}$-hal.

For this reaction, an inorganic base such as potassium carbonate, sodium carbonate, lithium carbonate, potassium hydrogencarbonate, sodium hydrogencarbonate or lithium hydroxide, an organic ba ase sun s triethylamine or tri-n-propylamine, or a metal hydride or an organic metal compound such as sodium hydride or n-butyl lithium, is used.

As the solvent for the reaction, a ketone type solvent (such as acetone, methyl ethyl ketone or diethyl ketone), an amide type solvent (such as formamide, N,N-dimethylformamide or N,N-dimethylacetamide), an alcohol type solvent (such as methanol or ethanol), water, or a solvent mixture thereof may be used, in the case where an inorganic or organic base is used. In the case where a metal hydride is used, an ether type solvent is usually preferably employed.

As the reaction temperature, a temperature within a range of from 0° C. to the boiling point of the solvent may usually be employed in the case where an inorganic base or an organic base is used. In the case where a metal hydride or an organic-metal compound is used, it is usually possible to employ a temperature within a range of from −78° C. to 60° C.

The molar ratio of the starting materials can optionally be set. However, the reactive derivative of the formula $R^{1'}$-hal may be used usually within a range of from 1 to 5 mols per mol of the compound of the formula (I-a).

For the isolation and purification of the desired product, conventional methods for organic syntheses such as recrystallization, various chromatography employing silica gel and distillation, may be employed.

Reaction formula (3)

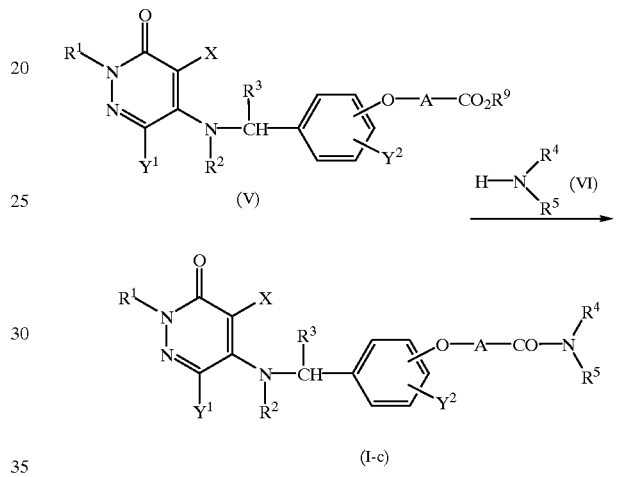

wherein $R^1$, $R^2$, $R^3$, $R^4$, $R^5$, $R^9$, X, $Y^1$, $Y^2$ and A are as defined above.

The reaction formula (3) illustrates a method wherein a 5-(ω-carboxyalkyleneoxy)benzylamino derivative or a 5-(ω-alkoxycarbonylalkyleneoxy)benzylamino derivative of the formula (V) is subjected together with an amine compound of the formula (VI) to a condensation reaction by dehydration or dealcoholization to produce the corresponding amide derivative of the formula (I-c).

For the condensation reaction in the case where $R^9$ is a hydrogen atom, condensation methods commonly known for peptide syntheses can widely be employed. For example, an acid chloride method and a mixed acid anhydride method as well as condensation methods employing condensing agents such as di-cyclohexylcarbodiimide, carbonyldiimidazole and N-hydroxysuccinimide can widely be employed, and a suitable condensation method may be selected for use depending upon the reactivity of the amine of the formula (VI). As the reaction conditions, conditions commonly employed may be adopted.

In the case of a reaction with an amine rich in nucleodhilic nature among amines of the formula (VI), the condensation reaction will proceed even with an ester wherein $R^9$ is an alkyl group. In such a case, as the solvent, any solvent may be employed without any particular restriction, so long as it is a solvent inert to the reaction. In many cases, the reaction may be conducted in the absence of a solvent. The reaction temperature may be set within a range of from room temperature to 200° C., but it is common to conduct the reaction within a range of from 50 to 150° C.

Reaction formula (4)

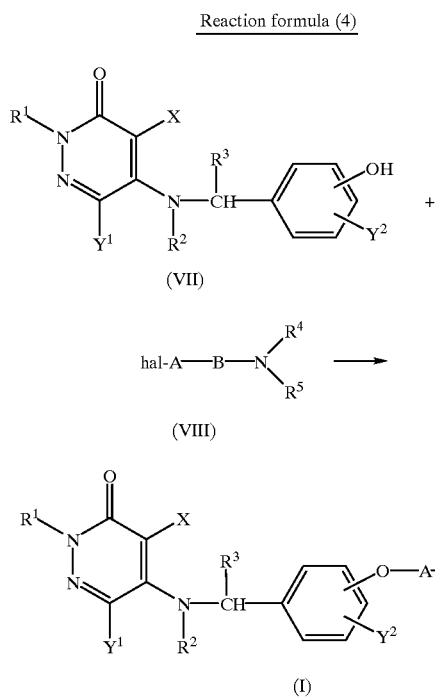

wherein $R^1$, $R^2$, $R^3$, $R^4$, $R^5$, X, $Y^1$, $Y^2$, A, B and hal are as defined above.

Reaction formula (4) illustrates a method for producing a compound of the formula (I) of the present invention by reacting a compound of the formula (VII) with a halogeno derivative of the formula (VIII).

For this reaction, an inorganic base such as potassium carbonate, sodium carbonate, lithium carbonate, sodium hydrogencarbonate, potassium hydrogencarbonate or lithium hydroxide, or an organic base such as triethylamine or tri-n-propylamine can usually be used.

As the solvent for the reaction, a ketone type solvent (such as acetone, methyl ethyl ketone or diethyl ketone), an amide type solvent (such as formamide, N,N-dimethylformamide or N,N-dimethylacetamide), an alcohol type solvent (such as methanol or ethanol), water, or a solvent mixture thereof, may suitably be employed.

As the reaction temperature, it is usually possible to employ a temperature within a range of from 0° C. to the boiling point of the solvent.

Reaction formula (5)

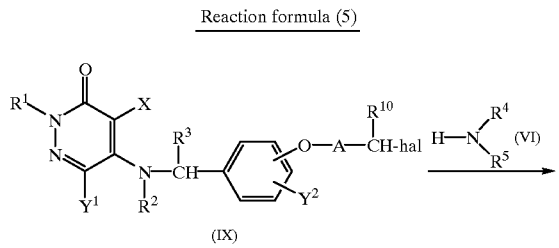

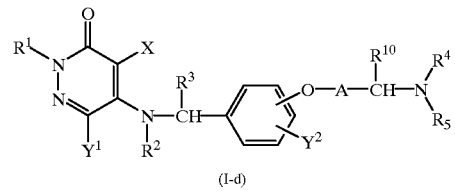

wherein $R^1$, $R^2$, $R^3$, $R^4$, $R^5$, $R^{10}$, X, $Y^1$, $Y^2$, A and hal are as defined above, and $R^7$ is a hydrogen atom or a $C_{1-4}$ alkyl group.

Reaction formula (5) illustrates a method for producing an amine derivative of the formula (I-d) as a compound of the present invention, by reacting a compound of the formula (IX) obtainable by a method corresponding to the reaction formula (4), with an amine compound of the formula (VI).

This reaction can be conducted in the same manner as the method described for reaction formula (4).

Reaction formula (6)

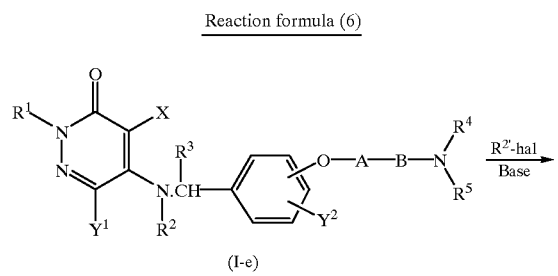

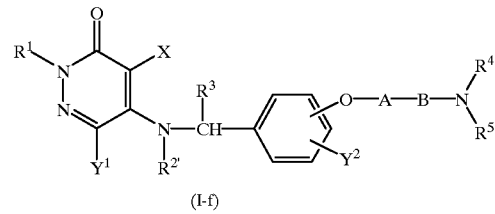

wherein $R^{2'}$ is a $C_{1-4}$ alkyl group, and $R^1$, $R^2$, $R^3$, $R^4$, $R^5$, X, $Y^1$, $Y^2$, A, B and hal are as defined above.

Reaction formula (6) illustrates a method for producing a compound wherein $R^2$ is a $C_{1-4}$ alkyl group among the compounds of the present invention, by reacting a compound of the formula (I-e) which is a compound of the formula (I) of the present invention wherein $R^2$ is a hydrogen atom, with an alkyl halide of the formula $R^{2'}$-hal in the presence of a base.

As the organic solvent to be used, an amide type solvent such as dimethylformamide, an ether type solvent such as tetrahydrofuran or diethyl ether, or an aprotic organic solvent such as n-hexane, benzene or toluene, may usually be employed, and as the base, a metal hydride such as sodium hydride, n-butyl lithium, lithium diisopropylamide or sodium amide, may be employed to obtain good results.

As the reaction temperature, a temperature within a range of from −78 to 10° C. may be employed for the reaction with the base, and a temperature within a range of from −15 to 70° C. may be employed for the reaction with the alkyl hydride.

Reaction formula (7)

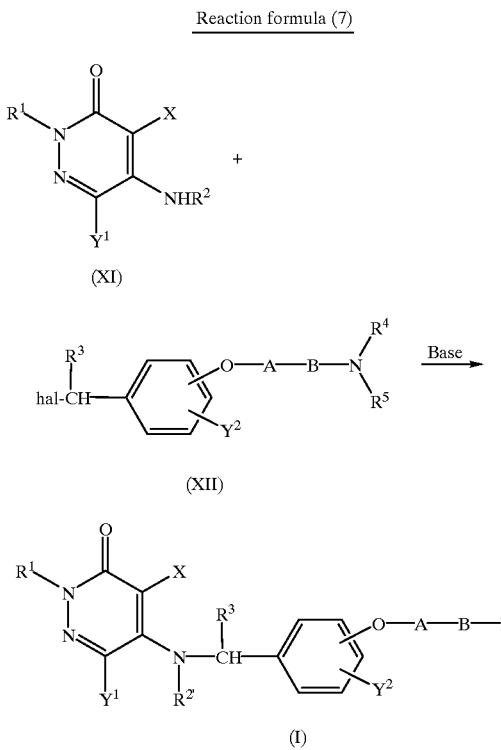

wherein $R^1$, $R^2$, $R^3$, $R^4$, $R^5$, X, $Y^1$, $Y^2$, A, B and hal are as defined above.

Reaction formula (7) illustrates a method for producing a compound of the formula (I) of the present invention by reacting a 3(2H)-pyridazinone of the formula (XI) having a —$NHR^2$ group at the 5-position, with a benzyl halide derivative of the formula (XII) in the presence of a base.

The reaction conditions may be similar to those described for reaction formula (6).

The manner of administration of the 3(2H)-pyridazinones of the formula (I) or their pharmaceutically acceptable salts of the present invention may be non-oral administration by an injection formulation (subcutaneous, intravenous, intramuscular or intraperitoneal injection formulation), an ointment, a suppository or an aerosol, or oral administration in the form of tablets, capsules, granules, pills, syrups, liquids, emulsions or suspensions.

The above pharmacological composition contains a compound of the present invention in an amount of from about 0.1 to 99.5% by weight, preferably from about 0.5 to 95% by weight, based on the total weight of the composition.

To the compound of the present invention or to the composition containing the compound of the present invention, other pharmacologically active compounds may be incorporated.

The compound of the present invention may be formulated into various formulations suitable for administration, in accordance with conventional methods commonly employed for the preparation of pharmaceutical formulations.

Namely, tablets, capsules, granules or pills for oral administration, may be prepared by using an excipient such as sugar, lactose, glucose, starch or mannitol; a binder such as syrup, gum arabic, gelatin, sorbitol, tragacanth gum, methyl cellulose or polyvinylpyrrolidone; a disintegrant such as starch, carboxymethyl cellulose or its calcium salt, crystal cellulose powder or polyethylene glycol; a gloss agent such as talc, magnesium or calcium stearate or silica; or a lubricant such as sodium laurate or glycerol.

The injections, solutions, emulsions, suspensions, syrups or aerosols, may be prepared by using a solvent for the active ingredient such as water, ethyl alcohol, isopropyl alcohol, propylene glycol, 1,3-butylene glycol, or polyethylene glycol; a surfactant such as a sorbitan fatty acid ester, a polyoxyethylene sorbitan fatty acid ester, a polyoxyethylene fatty acid ester, a polyoxyethylene ether of hydrogenated castor oil or lecithin; a suspending agent such as a sodium salt of carboxymethyl cellulose, a cellulose derivative such as methyl cellulose, or a natural rubber such as tragacanth gum or gum arabic; or a preservative such as a paraoxy benzoic acid ester, benzalkonium chloride or a salt of sorbic acid.

Likewise, the suppositories may be prepared by using e.g. polyethylene glycol, lanolin or coconut butter.

BEST MODE FOR CARRYING OUT THE INVENTION

EXAMPLES (REFERENCE EXAMPLES, PREPARATION EXAMPLES, FORMULATION EXAMPLES AND TEST EXAMPLES)

Now, the present invention will be described in further detail with reference to Examples (including Reference Examples, Preparation Examples, Formulation Examples and Test Examples). However, it should be understood that the present invention is by no means restricted by these specific Examples. In Reference Examples, Preparation Examples or Table II, the symbols "NMR" and "MS" indicate "nuclear magnetic resonance spectrum" and "mass spectrum", respectively. NMR was measured in heavy hydrogen chloroform, unless otherwise specified.

In the MS data in Table II, only the principal peaks or typical fragment peaks are given.

Reference Example 1

N-Benzyloxycarbonyl-3-hydroxy-4-methoxybenzylamine

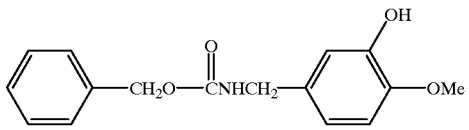

A mixture comprising 150 g of isovanillin, 93.2 g of sodium hydroxide, 99 g of hydroxylamine sulfate, 600 ml of ethanol and 1500 ml of water, was refluxed under heating with stirring for 30 minutes and then cooled to 40° C. Then, 93.2 g of sodium hydroxide was added thereto, and 180 g of Raney alloy was added thereto over a period of 30 minutes. The mixture was stirred for one hour. Insoluble matters were filtered off and washed with 100 ml of ethanol and 200 ml of water. The filtrate and the washing solutions were put together, and 53.6 g of sodium hydroxide was added thereto. Then, 186 g of benzyloxycarbonyl chloride was dropwise added under cooling with ice. The mixture was stirred for 4 hours. To this reaction solution, hydrochloric acid was added until the pH became from 1 to 2 and extracted with ethyl acetate. The organic layer was washed with water and a saturated sodium chloride aqueous solution and dried over anhydrous sodium sulfate. Then, the solvent was distilled off. The obtained residue was crystallized from diethyl ether to obtain 95.11 g of the above-identified compound as white crystals.

NMRδ: 7.34(s,5H), 6.79(s,3H), 5.78(s,1H), 5.12(br. s,2H), 4.25(d,2H), 3.84(s,3H). MS(m/e): 287(M⁺), 196, 152, 137, 91(100%).

Reference Example 2 t-Butyloxycarbonyl-3-hydroxy-4-methoxybenzylamine

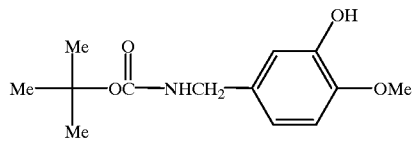

A mixture comprising 150 g of isovanillin, 91 g of sodium hydroxide, 89 g of hydroxylamine sulfate, 500 ml of ethanol and 1300 ml of water, was refluxed under heating with stirring for one hour and then cooled to 40° C. Then, 91 g of sodium hydroxide was added thereto, and 150 g of Raney alloy was gradually added thereto at an internal temperature of from 30 to 50° C. The mixture was stirred for one hour. Insoluble matters were filtered off and washed with 150 ml of ethanol and 150 ml of water. The filtrate and the washing solutions were put together and neutralized with concentrated hydrochloric acid under cooling until the pH became 8. Then, 1 l of acetonitrile was added thereto, and 215 g of di-t-butyl dicarbonate was dropwise added thereto at room temperature over a period of one hour. The mixture was stirred overnight. The organic layer was washed with a saturated sodium chloride aqueous solution and then dried over anhydrous sodium sulfate. Then, the solvent was distilled off. The obtained residue was purified by silica gel column chromatography (ethyl acetate:benzene=1:5) to obtain 126 g of the above-identified compound as oily substance.

NMRδ: 6.54–6.85(m,3H), 6.14–6.47(bs,1H), 4.92–5.34 (m,1H), 4.09(d,2H), 3.25(s,3H), 1.44(s,9H). MS(m/e): 153 (M⁺–100), 137(100%).

Reference Example 3

N-Benzyloxycarbonyl-3-ethoxycarbonylmethyloxy-4-methoxybenzylamine

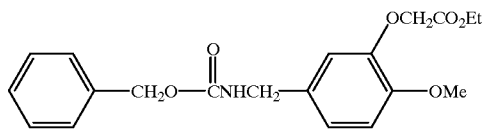

A mixture comprising 20 g of N-benzyloxycarbonyl-3-hydroxy-4-methoxybenzylamine, 17.43 g of ethyl bromoacetate, 14.43 g of potassium carbonate and 200 ml of 2-butanone, was refluxed under heating with stirring overnight. The mixture was cooled to room temperature. Then, inorganic substances were filtered off, and the filtrate was distilled under reduced pressure. The obtained residue was extracted with chloroform, and the organic layer was washed with water and a saturated sodium chloride aqueous solution and then dried over anhydrous sodium sulfate. Then, the solvent was distilled off. The obtained residue was crystallized from diethyl ether/n-hexane to obtain 17.83 g of the above-identified compound as white crystals.

NMRδ: 7.33(s,5H), 6.85(s,3H), 5.12(s,2H), 4.63(s,2H), 4.26(d,2H), 4.25(q,2H), 3.84(s,3H), 1.26(t,3H). MS(m/e): 373(M⁺), 282, 239(100%), 210, 164, 136, 91.

In the same manner, the following compounds were prepared.

N-Benzyloxycarbonyl-3-ethoxycarbonylpropoxy-4-methoxybenzylamine

NMRδ: 7.25–7.55(m,5H), 6.72–7.06(m,3H), 5.14(s,2H), 3.71–4.52(m,10H), 1.90–2.80(m,4H), 1.24(t,3H).

N-Benzyloxycarbonyl-3-ethoxycarbonylpentyloxy-4-methoxybenzylamine

Reference Example 4

N-Benzyloxycarbonyl-3-carboxymethyloxy-4-methoxybenzylamine

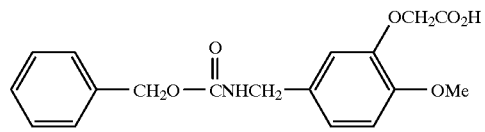

A mixture comprising 23.56 of N-benzyloxycarbonyl-3-ethoxycarbonylmethyloxy-4-methoxybenzylamine, 7.29 g of sodium hydroxide, 300 ml of methanol and 30 ml of water, was stirred at 60° C. for one hour. The reaction solution was neutralized by an addition of hydrochloric acid, and the solvent was distilled off under reduced pressure. Dilute hydrochloric acid was added to the obtained residue, and the mixture was extracted with chloroform. The extract layer was washed with water and a saturated sodium chloride aqueous solution and then dried over anhydrous sodium sulfate. The solvent was distilled off. The obtained residue was crystallized from diethyl ether/n-hexane to obtain 21.55 g of the above-identified compound as white crystals.

NMRδ: 7.34(s,5H), 6,84(s,3H), 5.13(s,3H), 4.62(s,2H), 4.25(d,2H), 3.83(s,3H). MS(m/e): 345(M⁺), 254, 210 (100%), 91.

In the same manner, the following compounds were prepared.

N-Benzyloxycarbonyl-3-carboxypropyloxy-4-methoxybenzylamine

N-Benzyloxycarbonyl-3-carboxypentyloxy-4-methoxybenzylamine

Reference Example 5

N-Benzyloxycarbonyl-3-(2,3-epoxypropyloxy)-4-methoxybenzylamine

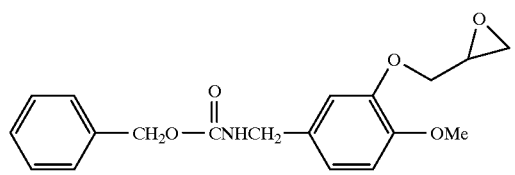

A mixture comprising 2 g of N-benzyloxycarbonyl-3-hydroxy-4-methoxybenzylamine, 20 ml of dimethylformamide, 1.4 g of potassium carbonate and 1.4 g of epibromohydrin, was stirred at 60° C. overnight. After distilling off the solvent under reduced pressure, the reaction mixture was extracted with ethyl acetate. The obtained organic layer was washed sequentially with an aqueous potassium carbonate solution and with a saturated sodium chloride aqueous solution and then dried over anhydrous sodium sulfate. Then, the solvent was distilled off to obtain 2.6 g of the above-identified compound as oily substance.

NMRδ: 7.32(s,5H), 6.81(s,3H), 5.0–5.5(m,3H), 3.9–4.6 (m,7H), 3.8(s,3H). MS(m/e): 343(M+), 252,208,19(100%).

Reference Example 6

N-Benzyloxycarbonyl-3-(4-methylpiperazin-1-yl)-carbonylmethoxy-4-methoxybenzylamine

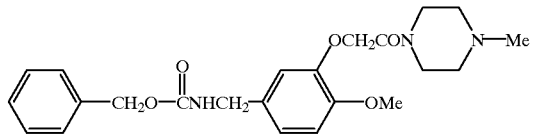

A mixture comprising 5 g of N-benzyloxycarbonyl-3-carboxymethyloxy-4-methoxybenzylamine, 1.67 g of triethylamine and 40 ml of tetrahydrofuran, was cooled with ice, and 1.79 g of ethyl chloroformate dissolved in 10 ml of tetrahydrofuran, was dropwise added thereto. The mixture was stirred for 2 hours. Then, 1.65 g of methylpiperazine dissolved in 10 ml of tetrahydrofuran, was added to the reaction solution, and the mixture was stirred at room temperature for 4.5 hours. The precipitate was filtered off, and the filtrate was distilled under reduced pressure. Water was added to the obtained residue, and the mixture was extracted with chloroform. The extract solution was washed with water and a saturated sodium chloride aqueous solution and then dried over anhydrous sodium sulfate. Then, the solvent was distilled off. The obtained residue was crystallized from ethyl acetate/diethyl ether/n-hexane to obtain 3.53 g of the above-identified compound as white crystals.

NMRδ: 7.25(s,5H), 6.78(s,3H), 5.03(s,3H), 4.62(s,2H), 4.23(d,2H), 3.78(s,3H), 3.40–3.72(m,4H), 2.11–2.60(m,7H). MS(m/e): 427(M+), 292, 235, 141, 91(100%).

In the same manner, the following compounds were prepared.

N-Benzyloxycarbonyl-3-[4-(3-pyridylmethyl)-piperazin-1-yl]carbonylmethoxy-4-methoxybenzylamine MS(m/e): 504(M+), 92(100%).

N-Benzyloxycarbonyl-3-(4-benzylpiperazin-1-yl)-carbonylmethoxy-4-methoxybenzylamine NMRδ: 7.15–7.43(m,10H), 6.7–6.92(m,3H), 4.85–5.24 (m,3H), 4.62(s,2H), 4.22(d,2H), 3.4–3.96(m,9H), 2.25–2.7 (m,4H).

N-Benzyloxycarbonyl-3-[4-(4-fluorobenzyl)-piperazin-1-yl]carbonylmethoxy-4-methoxybenzylamine NMRδ: 6.60–7.50(m,12H), 5.0–5.5(m,3H), 4.62(s,2H), 4.22(d,2H), 3.22–3.95(m,9H), 2.2–2.7(m,4H).

N-Benzyloxycarbonyl-3-[4-(3-pyridylmethyl)-piperazin-1-yl]-carbonylpropoxy-4-methoxybenzylamine MS(m/e): 532(M+), 92(100%).

N-Benzyloxycarbonyl-3-(4-benzylpiperazin-1-yl)-carbonylpropoxy-4-methoxybenzylamine NMRδ: 7.0–7.40(m,10H), 6.60–6.90(m,3H), 5.50–5.51 (m,3H), 3.22–4.37(m,13H), 2.0–2.68(m,8H).

N-Benzyloxycarbonyl-3-(4-benzylpiperazin-1-yl)-carbonylpentyloxy-4-methoxybenzylamine NMRδ: 7.0–7.35(m,10H), 6.60–6.80(m,3H), 5.0–5.50(m, 3H), 3.20–4.32(m,13H), 1.1–2.48(m,12H).

Reference Example 7

N-Benzyloxycarbonyl-3-[{4-(4-fluorobenzyl)-piperazin-1-yl}-β-hydroxypropyloxy]-4-methoxybenzylamine

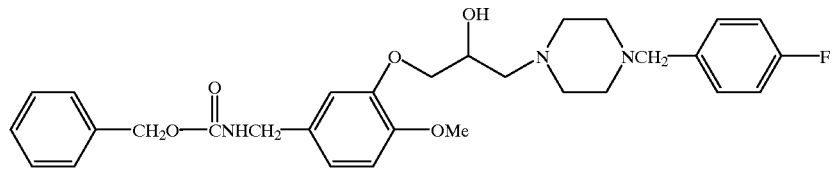

A mixture comprising 2.4 g of N-benzyloxycarbonyl-3-(2,3-epoxypropyloxy)-4-methoxybenzylamine, 30 ml of ethanol and 1.4 g of 4-fluorobenzyl-piperazine, was refluxed under heating with stirring overnight. The mixture was cooled to room temperature, and then the reaction solution was concentrated under reduced pressure and extracted with chloroform. The organic layer was washed with an aqueous potassium carbonate solution and then dried over anhydrous sodium sulfate. Then, the solvent was distilled off under reduced pressure. The obtained residue was purified by silica gel column chromatography (ethyl acetate:methanol=19:1) to obtain 2.6 g of the above-identified compound.

NMRδ: 6.75–7.42(m,12H), 5.0–5.5(m,3H), 4.26(d,2H), 3.82–4.10(m,2H), 3.77(s,3H), 3.20–3.60(m,3H), 2.20–2.85 (m,10H). MS(m/s): 537(M+), 207(100%), 109.

In the same manner, the following compounds were prepared.

N-Benzyloxycarbonyl-3-[{4-(2-quinolylmethyl)-piperazin-1-yl}-β-hydroxypropyloxy]-4-methoxybenzylamine NMRδ: 7.03–8.12(m,11H), 6.60–6.87 (m,3H), 5.30–5.70(m,1H), 5.05(s,2H), 3.22–4.37(m,11H), 2.22–2.80(m,10H).

N-Benzyloxycarbonyl-3-[{4-(4-aminobenzyl)-piperazin-1-yl}-β-hydroxypropyloxy]-4-methoxybenzylamine NMRδ: 6.45–7.41(m,12H), 5.40–6.78(m,1H), 5.04(s, 2H), 3.50–4.38(m,11H), 3.30(s,2H), 2.10–2.80(m,8H).

Reference Example 8

3-(4-Methylpiperazin-1-yl)-carbonylmethoxy-4-methoxybenzylamine

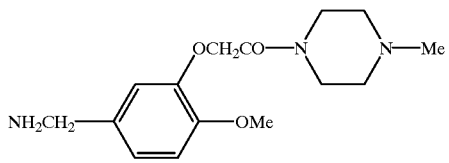

A mixture comprising 3.26 g of N-benzyloxycarbonyl-3-(4-methylpiperazin-1-yl)-carbonylmethoxy-4-methoxybenzylamine, 0.5 g of 5% palladium carbon and 70 ml of ethanol, was stirred at 60° C. for 6 hours in a hydrogen atmosphere and further at room temperature overnight. Palladium carbon was filtered off, and then the filtrate was distilled off under reduced pressure to obtain 2.45 g of the above-identified compound as slightly brown oil.

NMRδ: 6.88(s,3H), 4.74(s,2H), 3.50–4.10(m,9H), 2.29–2.58(m,7H), 1.65(s,2H). MS(m/s): 293($M^+$), 152, 299, 70(100%).

In the same manner, the following compounds were prepared.

3-[4-(3-Pyridylmethyl)-piperazin-1-yl]carbonylmethoxy-4-methoxybenzylamine

MS(m/e): 370($M^+$), 92(100%).

3-(4-benzylpiperazin-1-yl)-carbonylmethoxy-4-methoxybenzylamine

MS(m/e): 369($M^+$), 91(100%).

3-[4-(4-Fluorobenzyl)-piperazin-1-yl]carbonylmethoxy-4-methoxybenzylamine

MS(m/e): 387($M^+$), 109(100%).

3-[4-(3-pyridylmethyl)-piperazin-1-yl]carbonylpropoxy-4-methoxybenzylamine

MS(m/e): 398($M^+$), 92(100%).

3-(4-methylpiperazin-1-yl)-carbonylpropoxy-4-methoxybenzylamine

MS(m/e): 321($M^+$), 99(100%).

3-(4-benzylpiperazin-1-yl)-carbonylpropoxy-4-methoxybenzylamine

MS(m/e): 397($M^+$), 91(100%).

3-[4-(4-Fluorobenzyl)-piperazin-1-yl]-1-oxo-2-methylethyloxy]-4-methoxybenzylamine MS(m/e): 401($M^+$), 109(100%).

3-(4-Benzylpiperazin-1-yl)-carbonylpentyloxy-4-methoxybenzylamine

MS(m/e): 425($M^+$), 91(100%).

Preparation Example 1

4-Chloro-5-[3-(4-methylpiperazin-1-yl)-carbonylmethoxy-4-methoxybenzylamino]-3(2H)-pyridazinone

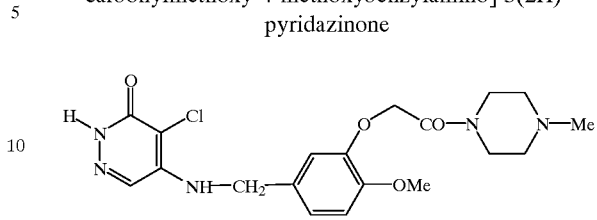

A mixture comprising 1.16 g of 3-(4-methylpiperazin-1-yl)-carbonylmethoxy-4-methoxybenzylamine, 0.5 g of 4,5-dichloro-3(2H)-pyridazinone, 0.46 g of triethylamine, 10 ml of ethanol and 10 ml of water, was refluxed under heating with stirring overnight. The solvent was distilled off under reduced pressure, and an aqueous potassium carbonate solution was added to the residue. The mixture was extracted with chloroform. The extract solution was washed with water and a saturated sodium chloride aqueous solution and then dried over anhydrous sodium sulfate. Then, the solvent was distilled off. The obtained residue was purified by silica gel column chromatography and then crystallized from chloroform/diethyl ether to obtain 0.61 g of the above-identified compound as white crystals.

NMRδ: 12.66(br. s,1H), 7.44(s,1H), 6.78(s,3H), 5.43(t, 1H), 4.68(s,2H), 4.39(d,2H), 3.77(s,3H), 3.30–3.75(m,4H), 2.0–2.60(m,7H). MS(m/e): 421($M^+$), 386, 140, 99, 70(100%).

Reference Example 9

4-Chloro-5-(3-carboxymethyloxy-4-methoxybenzylamino)-3(2H)-pyridazinone

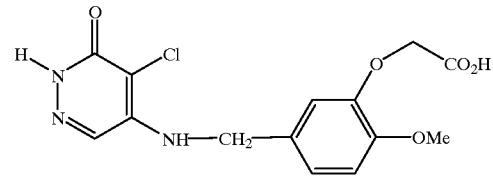

A mixture comprising 0.3 g of 4-chloro-5-[3-(4-methylpiperazin-1-yl)-carbonylmethoxy-4-methoxybenzylamino]-3(2H)-pyridazinone, 2.0 g of potassium hydroxide, 10 ml of ethanol and 2 ml of water, was refluxed under heating with stirring overnight. The reaction solution was neutralized with an aqueous hydrochloric acid solution. Then, the solvent was distilled off under reduced pressure. Then, water was added to the obtained residue, and the mixture was extracted with chloroform. The extract solution was washed with water and a saturated sodium chloride aqueous solution and then dried over anhydrous sodium sulfate. Then, the solvent was distilled off to obtain 212 mg of the above-identified compound as white solid.

MS(m/e): 281($M^+$—$CHCO_2H$), 246, 209, 159, 145 (100%), 116.

Preparation Example 2

4-Chloro-5-[3-(3-Pyridylmethylaminocarbonylmethoxy)-4-methoxybenzylamino]-3(2H)-pyridazinone

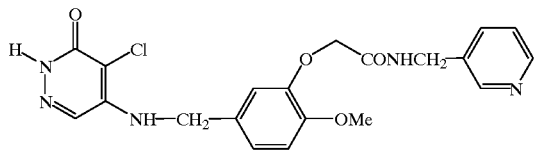

A mixture comprising 200 mg of 4-chloro-5-(3-carboxymethyloxy-4-methoxbenzylamino)-3(2H)-pyridazinone, 65 mg of triethylamine and 10 ml of N,N-dimethylformamide, was cooled with ice, and 88 mg of isobutyl chloroformate was added thereto. The mixture was stirred at that temperature for one hour, and then 140 mg of 3-picolylamine was added thereto. The mixture was stirred at room temperature overnight. The solvent was distilled off under reduced pressure, and water was added to the obtained residue. The mixture was extracted with chloroform. The extract solution was washed with water and a saturated sodium chloride aqueous solution and then dried over anhydrous sodium sulfate. Then, the solvent was distilled off. The obtained residue was purified by silica gel column chromatography (eluent: chloroform/methanol=9/1) to obtain 129 mg of the above-identified compound as white solid.

NMRδ: 8.35–8.58(m,2H), 7.81–8.33(m,1H), 7.72(s,1H), 7.45–7.60(m,2H), 6.88(s,3H), 6.40–6.80(m,1H), 4.31–4.62 (m,6H), 3.75(s,3H). MS(m/e): 429(M$^+$), 394, 298, 137, 121, 107, 92(100%).

Reference Example 10

N-Benzyloxycarbonyl-3-(3-chloropropoxy)-4-methoxybenzylamine

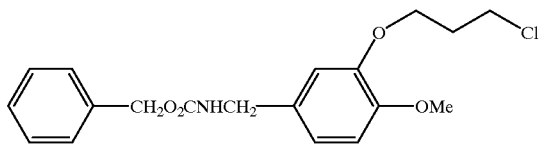

A mixture comprising 20 g of N-benzyloxycarbonyl-3-hydroxy-4-methoxybenzylamine, 14.43 g of potassium carbonate, 16.44 g of bromochloropropane and 200 ml of 2-butanone, was refluxed under heating with stirring for 16 hours. The mixture was cooled to room temperature. Then, inorganic substances were filtered off, and the filtrate was distilled under reduced pressure. The obtained residue was extracted with chloroform, and the organic layer was washed with water and a saturated sodium chloride aqueous solution and then dried over anhydrous sodium sulfate. Then, the solvent was distilled off. The obtained residue was crystallized from diethyl ether/n-hexane to obtain 23.19 g of the above-identified compound as white crystals.

NMRδ: 7.21(s,5H), 6.71(s,3H), 5.04(s,3H), 4.20(d,2H), 4.02(t,2H), 3.75(s,3H), 3.67(t,2H), 1.94–2.47(m,2H). MS(m/e): 363(M$^+$), 316, 273(100%), 228, 152, 137, 125, 91.

In the same manner, the following compounds were prepared.

N-Benzyloxycarbonyl-3-(2-chloroethoxy)-4-methoxybenzylamine

N-Benzyloxycarbonyl-3-(2-diethylaminoethoxy)-4-methoxybenzylamine

Reference Example 11

N-Benzyloxycarbonyl-3-[3-(4-formylpiperazin-1-yl)propoxyl-4-methoxybenzylamine

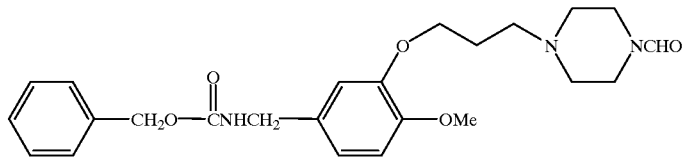

A mixture comprising 23.1 g of N-benzyloxycarbonyl-3-(3-chloropropoxy)-4-methoxybenzylamine, 8.7 g of N-formylpiperazine, 13,16 g of potassium carbonate, 0.95 g of sodium iodide and 300 ml of N,N-dimethylformamide, was stirred at 80° C. for 16 hours. The mixture was cooled to room temperature. Then, inorganic substances were filtered off, and the filtrate was distilled off under reduced pressure. The obtained residue was extracted with chloroform, and the organic layer was washed with water and a saturated sodium chloride aqueous solution and then dried over anhydrous sodium sulfate. The solvent was distilled off to obtain 30.67 g of the above-identified compound as slightly brown oil.

NMRδ: 7.97(s,1H), 7.32(s,5H), 6.81(s,3H), 5.36(brt,1H), 5.11(s,2H), 4.26(d,2H), 4.02(t,2H), 3.81(s,3H), 3.12–3.66 (m,4H), 1.78–2.78(m,8H). MS(m/e): 441(M$^+$), 383, 306, 155(100%), 128, 91.

In the same manner, the following compounds were prepared.

N-Benzyloxycarbonyl-3-(3-diethylaminopropoxy)-4-methoxybenzylamine

N-Benzyloxycarbonyl-3-[2-(4-benzylpiperazin-1-yl)-ethoxy]-4-methoxybenzylamine

N-Benzyloxycarbonyl-3-[2-{4-(4-chlorobenzyl)-piperazin-1-yl}-ethoxy]-4-methoxybenzylamine N-Benzyloxycarbonyl-3-[2-{4-(4-fluorobenzyl)-piperazin-1-yl}-ethoxy]-4-methoxybenzylamine N-Benzyloxycarbonyl-3-[3-(4-benzylpiperazin-1-yl)-propoxy]-4-methoxybenzylamine N-Benzyloxycarbonyl-3-[3-(4-methylpiperazin-1-yl)-propoxy]-4-methoxybenzylamine

Reference Example 12

3-(3-(4-Formylpiperazin-1-yl)-propoxy]-4-methoxybenzylamine

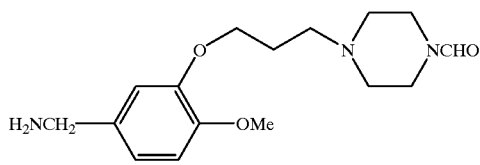

A mixture comprising 30.4 g of N-benzyloxycarbonyl-3-[3-(4-formylpiperazin-1-yl)-propoxy]-4-methoxybenzylamine, 3.1 g of 5% palladium carbon and 300 ml of ethanol, was stirred at 60° C. for 9 hours under a hydrogen atmosphere. Palladium carbon was filtered off, and then the filtrate was distilled off under reduced pressure to obtain 17.99 g of the above-identified compound as slightly brown oil.

NMRδ: 8.03(s,1H), 6.86(s,3H), 4.11(t,2H), 3.84(s,3H), 3.25–3.71(m,4H), 2.30–2.82(m,4H), 1.82–2.30(m,4H). MS(m/e): 307(M$^+$), 292, 246, 171, 155, 125, 99(100%).

In the same manner, the following compounds were prepared.

3-(2-Diethylaminoethoxy)-4-methoxybenzylamine 3-(3-Diethylaminopropoxy)-4-methoxybenzylamine 3-[2-(4-Benzylpiperazin)-1-yl]-ethoxy-4-methoxybenzylpiperazine 3-[2-{4-(4-Chlorobenzyl)-piperazin-1-yl}-ethoxy]-4-methoxybenzylamine 3-[2-{4-(4-Fluorobenzyl)-piperazin-1-yl}-ethoxy]-4-methoxybenzylamine 3-[3-(4-benzylpiperazin-1-yl)-propoxy]-4-methoxybenzylamine 3-[3-(4-methylpiperazin-1-yl)-propoxy]-4-methoxybenzylamine

Preparation Example 3

4-Chloro-5-[3-{3-(4-formylpiperazin-1-yl)-propoxy}-4-methoxybenzylamino]-3(2H)-pyridazinone (Compound No. 50)

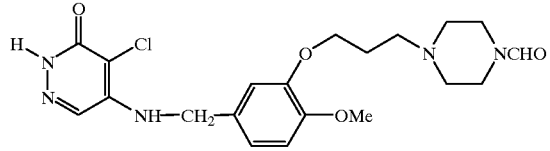

A mixture comprising 11.58 g of 3-[3-(4-formylpiperazin-1-yl)-propoxy]-4-methoxybenzylamine, 5.0 g of 4,5-dichloro-3(2H)-pyridazinone, 4.6 g of triethylamine, 50 ml of n-propanol and 50 ml of water, was refluxed under heating with stirring for 14 hours. The solvent was distilled off under reduced pressure, and an aqueous potassium carbonate solution was added to the obtained residue, and the mixture was extracted with chloroform. The organic layer was washed with water and a saturated sodium chloride aqueous solution and then dried over anhydrous sodium sulfate. Then, the solvent was distilled off, and the residue was purified by silica gel column chromatography to obtain 6.21 g of the above-identified compound as slightly yellow white solid.

NMRδ: 12.49(br. s,1H), 8.06(s,1H), 7.65(s,1H), 6.88(s, 3H), 5.37(t,1H), 4.51(d,2H), 4.08(t,2H), 3.87(s,3H), 3.19–3.74(m,4H), 2.30–2.84(m,6H), 1.76–2.30(m,2H).

Preparation Example 4

4-Chloro-5-[3-{3-(4-ethylpiperazin-1-yl)-propoxy}-4-methoxybenzylamino]-3(2H)-pyridazinone

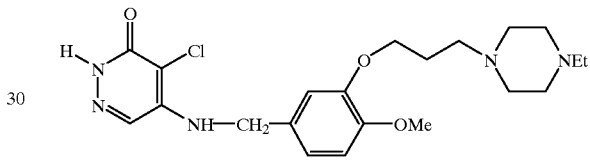

A mixture comprising 1.0 g of 4-chloro-5-[3-{3-(4-formylpiperazin-1-yl)-propoxy}-4-methoxybenzylamino]-3(2H)-pyridazinone, 0.62 g of potassium hydroxide, 7 ml of ethanol and 7 ml of water, was refluxed under heating with stirring for 3.5 hours, and then 0.32 g of potassium carbonate and 570 mg of ethyl bromide were added thereto. The mixture was stirred at 60° C. for 4 hours. The solvent was distilled off under reduced pressure, and water was added to the obtained residue. The mixture was extracted with chloroform. The extract solution was washed with water and a saturated sodium chloride aqueous solution and then dried over anhydrous sodium sulfate. Then, the solvent was distilled off. The obtained residue was purified by silica gel column chromatography to obtain 0.50 g of the above-identified compound as slightly brown solid.

NMRδ: 7.65(s,1H), 6.89(s,3H), 5.41(collapsed, 1H), 4.50 (d,2H), 4.08(t,2H), 3.87(s,3H), 1.73–3.10(m,14H), 1.08(t, 3H). MS(m/e): 435(M$^+$), 365, 343, 206, 127(100%), 99.

In the same manner, the following compound was prepared.

4-Chloro-5-[3-{3-(4-(4-fluorobenzyl)-piperazin-1-yl)-propoxy}-4-methoxybenzylamino]-3(2H)-pyridazinone MS(M/e): 515(M$^+$), 109(100%).

Preparation Example 5

2-Ethyl-4-chloro-5-[3-{2-(4-(4-fluorobenzyl)-piperazin-1-yl)-ethoxy}-4-methoxybenzylamino]-3(2H)-pyridazinone

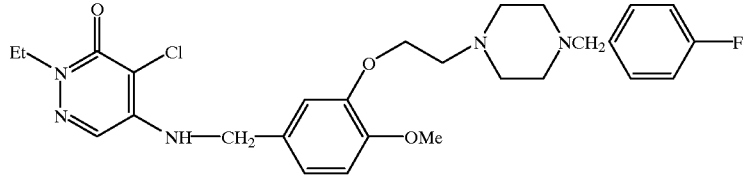

A mixture comprising 500 mg of 4-chloro-5-[3-{2-(4-(4-fluorobenzyl)-piperazin-1-yl)-ethoxy}-4-methoxybenzylamino]-3(2H)-pyridazinone, 130 mg of ethyl bromide, 190 mg of potassium carbonate and 10 ml of 2-butanone, was refluxed under heating with stirring for 5 hours. Inorganic substances were filtered off, and then the solvent was distilled off under reduced pressure. Water was added to the obtained residue, and the mixture was extracted with chloroform. The extract solution was washed with water and a saturated sodium chloride aqueous solution and then dried over anhydrous sodium sulfate. Then, the solvent was distilled off. The obtained residue was purified by silica gel column chromatography (eluent: chloroform/ethanol= 19/1) to obtain 429 mg of the above-identified compound as a colorless transparent sticky substance.

NMRδ: 7.47(s,1H), 7.00–7.31(m,4H), 6.88(s,3H), 5.20(t, 1H), 4.46(d,2H), 4.14(t,2H), 4.12(q,2H), 3.85(s,3H), 3.47(s, 2H), 2.73(t,2H), 2.21–3.05(m,10H), 1.32(t,3H). MS(m/e): 574(M$^+$), 493, 273, 221, 192(100%), 164, 111, 84.

Reference Example 13

1-Chloroacetyl-4-(2-quinolylmethyl)-piperazine

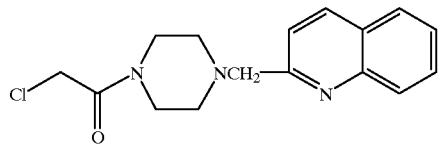

A solution comprising 600 mg of N-quinolylmethylpiperazine and 20 ml of dry tetrahydrofuran was cooled to −60° C., and a mixed solution comprising 330 mg of acetyl chloride and 5 ml of dry tetrahydrofuran, was dropwise added thereto over a period of 10 minutes. The mixture was stirred at −60° C. for one hour, and 10 ml of water was added thereto. The mixture was stirred at room temperature for 20 minutes. The reaction solution was distilled under reduced pressure and extracted with chloroform. The organic layer was washed with an aqueous potassium carbonate solution and dried over anhydrous sodium sulfate. Then, the solvent was distilled off under reduced pressure to obtain 750 mg of the above-identified compound as oily substance.

NMRδ: 7.32–8.20(m,6H), 4.01(s,2H), 3.20–3.90(m,6H), 2.30–2.74(m,4H). MS(m/e): 143(M$^+$−160)

In the same manner, the following compounds were prepared.

1-Chloroacetyl-4-(4-chorobenzyl)-piperazine

MS(m/e): 286(M$^+$), 125(100%).

1-Chloroacetyl-4-[1-(4-fluorobenzyl)-2-methylbenzoimidazole]-piperazine

NMRδ: 6.66–7.40(m,8H), 5.44(s,2H), 3.95(s,2H), 3.74(s, 2H), 3.04–3.60(m,4H), 2.24–2.66(m,4H).

1-Chloroacetyl-4-benzylpiperazine
MS(m/e): 252(M$^+$), 91(100%).

1-Chloroacetyl-4-benzylpiperidine
MS(m/e): 251(M$^+$), 91(100%).

1-Chloroacetyl-4-(t-butyloxycarbonylaminobenzyl)-piperazine
MS(m/e): 368(M$^+$), 150(100%).

Reference Example 14

N-t-Butyloxycarbonyl-3-[4-(2-quinolylmethylpiperazin)-1-yl]carbonylmethoxy-4-methoxybenzylamine

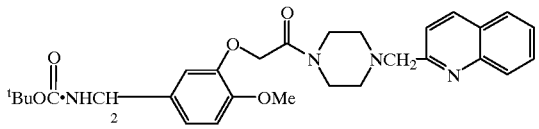

A mixture comprising 660 mg of t-butyloxycarbonyl-3-hydroxy-4-methoxybenzylamine, 10 ml of dimethylformamide, 510 mg of potassium carbonate and 750 mg of 1-chloroacetyl-4-(2-quinolylmethyl)-piperazine, was heated at 80° C. overnight with stirring. Insoluble matters were filtered off, and then the reaction solution was distilled under reduced pressure and extracted with chloroform. The extract solution was washed with an aqueous potassium carbonate solution and then purified by silica gel column chromatography (ethyl acetate:methanol=19:1) to obtain 1.2 g of the above-identified compound as oily substance.

NMRδ: 7.32–8.03(m,6H), 6.63–6.93(m,3H), 5.15–5.50 (m,1H), 4.64(s,2H), 4.16(d,2H), 3.38–3.93(m,9H), 2.30–2.73(m,4H), 1.43(s,9H).

MS(m/e): 520(M$^+$), 144(100%).

In the same manner, the following compounds were prepared.

N-t-Butyloxycarbonyl-3-[4-(4-chlorobenzyl)-piperazin-1-yl]-carbonylmethoxy-4-methoxybenzylamine
MS(m/e): 503(M$^+$), 125(100%).

N-t-Butyloxycarbonyl-3-[4-{1-(4-fluorobenzyl)-2-methylbenzoimidazole}-piperazin-1-yl]-carbonylmethoxy-4-methoxybenzylamine
NMRδ: 6.10–7.35(m,11H), 5.45(s,2H), 4.80–5.17(m,1H), 4.10(s,2H), 4.15(d,2H), 3.76(s,3H), 3.70(s,12H), 3.26–3.65 (m,4H), 2.27–2.65(m,4H).

N-t-Butyloxycarbonyl-3-(4-benzylpiperidin-1-yl)-carbonylmethoxy-4-methoxybenzylamine MS(m/e): 468(M⁺), 91(100%).

N-t-Butyloxycarbonyl-3-(4-t-butyloxycarbonylaminobenzylpiperazin-1-yl)-carbonylmethoxy-4-methoxybenzylamine MS(m/e): 585(M⁺), 150(100%).

Reference Example 15

3-[4-(2-Quinolylmethyl)-piperazin-1-yl]-carbonylmethoxy-4-methoxybenzylamine

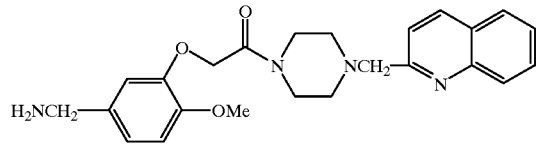

A mixture comprising 1.3 g of t-butyloxycarbonyl-3-[4-(2-quinolylmethyl)-piperazin-1-yl]-carbonylmethoxy-4-methoxybenzylamine, 14 ml of chloroform and 2.8 g of trifluoroacetic acid, was stirred at room temperature for one day. To the reaction solution, 50 ml of chloroform and 50 ml of 0.5N hydrochloric acid were added, and the mixture was reversely extracted. The aqueous layer was adjusted to pH 12 with an aqueous sodium hydroxide solution and extracted with chloroform. The organic layer was washed with an aqueous potassium carbonate solution and then dried over anhydrous sodium sulfate. Then, the solvent was distilled off under reduced pressure to obtain 850 mg of the above-identified compound as oily substance.

NMRδ: 7.39–8.20(m,6H), 6.72–7.0(m,3H), 4.7(s,2H), 3.40–4.00(m,11H), 2.32–2.70(m,4H), 2.05(br. s,2H). MS(m/e): 420(M⁺), 143(100%).

In the same manner, the following compounds were prepared.

3-[4-(4-Chlorobenzyl)-piperazin-1-yl]-carbonylmethoxy-4-methoxybenzylamine

MS(m/e): 403(M⁺), 125(100%)

3-[3-{4-(4-Fluorobenzyl)-piperazin-1-yl}-2,2-dimethylpropoxy]-4-methoxybenzylamine MS(m/e): 429(M⁺), 109(100%).

3-(4-Benzylpiperizin-1-yl)-carbonylmethoxy-4-methoxybenzylamine

MS(m/e): 368(M⁺), 91(100%).

3-[4-{1-(4-Fluorobenzyl)-2-benzimidazolylmethyl}-piperazin-1-yl]-carbonylmethoxy-4-methoxybenzylamine MS(m/e): 517(M⁺), 109(100%).

Preparation Example 6

4-Chloro-5-[3-{4-(2-quinolylmethyl)-piperazin-1-yl}-carbonylmethoxy-4-methoxybenzylamino]-6-ethoxy-3(2H)-pyridazinone

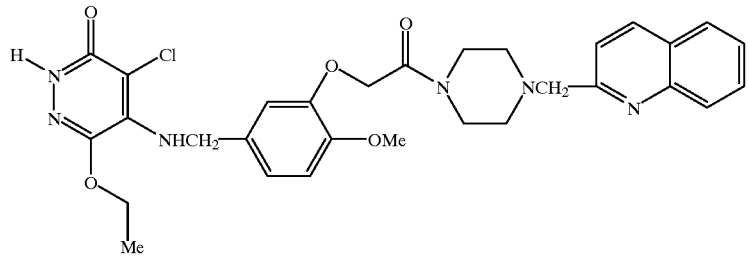

A mixture comprising 2.4 g of 3-[4-(2-quinolylmethyl)-piperazin-1-yl]-carbonylmethoxy-4-methoxybenzylamine, 1 g of 4,5-dichloro-6-ethoxy-3(2H)-pyridazinone, 580 mg of triethylamine, 10 ml of propanol and 10 ml of water, was refluxed under heating with stirring overnight. The solvent was distilled off under reduced pressure, and the residue was extracted with chloroform. The organic layer was washed with an aqueous potassium carbonate solution and then dried over anhydrous sodium sulfate. Then, the solvent was distilled off. The obtained residue was purified by silica gel column chromatography (ethyl acetate:methanol= 6:1→chloroform:methanol=12:1) and then crystallized from diethyl ether to obtain 1.5 g of the above-identified compound as white crystals.

NMRδ: 7.40–8.28(m,6H), 6.72–7.05(m,3H), 4.62–5.40 (m,5H), 3.48–4.50(m,11H), 2.32–2.70(m,4H), 1.31(t,3H). MS(m/e): 592(M⁺), 143(100%).

Reference Example 16

1-Formyl-4-(4-aminobenzyl)-piperazine

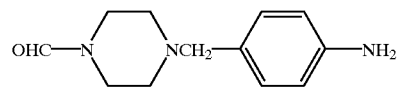

A mixture comprising 9 g of 1-formyl-4-(4-nitrobenzyl)-piperazine, 180 ml of methanol and 14.6 of nickel chloride hexahydrate, was cooled in ice bath, and 4.6 g of sodium borohydride was slowly added thereto. The mixture was stirred at 0° C. for 30 minutes and further at room temperature for 30 minutes. The reaction solution was distilled off under reduced pressure, and the residue was dissolved by an addition of 200 ml of 10% hydrochloric acid, and adjusted to pH 10 with 28% aqueous ammonia. Then, the mixture was extracted with ethyl acetate. The extract solution was washed with a saturated sodium chloride aqueous solution and then dried over anhydrous sodium sulfate. Then, the solvent was distilled off under reduced pressure. The residue was crystallized from diethyl ether to obtain 8.0 g of the above-identified compound as white crystals.

NMRδ: 7.82(s,1H), 6.97(d,2H), 6.47(d,2H), 3.01–3.91(m,8H), 2.11–2.48(m,4H). MS(m/e): 263(M⁺), 218(100%).

Reference Example 17

1-Formyl-4-(4-t-butyloxycarbonylaminobenzyl)-piperazine

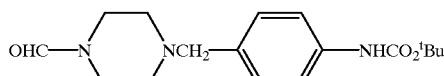

A mixture comprising 4 g of 1-formyl-4-aminobenzylpiperazine, 50 ml of toluene and 4.8 g of di-t-butyl dicarbonate, was refluxed under heating for 5 hours. The reaction solution was concentrated under reduced pressure, and the residue was purified by silica gel column chromatography (ethyl acetate:methanol=9:1) and then crystallized from diethyl ether to obtain 5.1 g of the above-identified compound as white crystals.

NMRδ: 7.87(s,1H), 6.97–7.42(m,5H), 3.15–3.65(m,6H), 2.15–2.57(m,4H), 1.45(s,9H). MS(m/e): 319(M⁺), 106 (100%).

Reference Example 18

1-(4-t-Butyloxycarbonylaminobenzyl)-piperazine

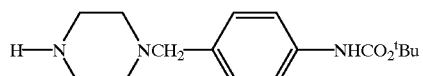

4 g of 1-formyl-4-(t-butyloxycarbonylaminobenzyl)-piperazine was dissolved in 50 ml of methanol, and an aqueous solution having 1.5 g of sodium hydroxide dissolved in 10 ml of water, was added thereto. The mixture was heated at 60° C. for 5 hours. The reaction solution was concentrated under reduced pressure and then extracted with chloroform. The organic layer was washed with an aqueous potassium carbonate solution and then dried over anhydrous sodium sulfate. Then, the solvent was distilled off under reduced pressure. The residue was purified by silica gel column chromatography (chloroform:methanol=5:1) and then crystallized from diethyl ether to obtain 3.2 g of the above-identified compound as white crystals.

NMRδ: 7.0–7.7(m,5H), 3.38(s,2H), 2.60–3.12(m,4H), 1.90–2.60(m,5H), 1.50(s,9H). MS(m/e): 291(M⁺), 206, 106 (100%).

Preparation Example 7

4-Chloro-5-[3-(4-(4-aminobenzyl)-piperazin-1-yl)-carbonylmethoxy-4-methoxybenzylamino]-6-isopropoxy-3(2H)-pyridazinone

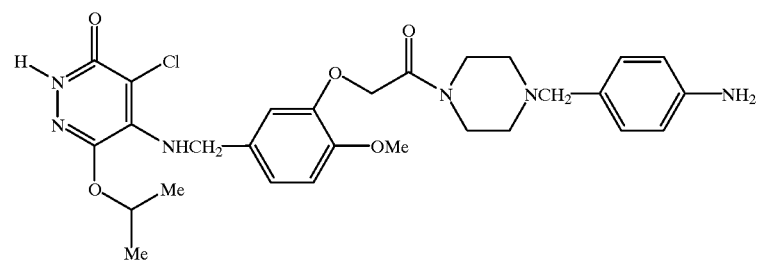

A mixture comprising 1.6 g of 3-[4-(4-aminobenzyl)piperazin-1-yl]-carbonylmethoxy-4-methoxybenzylamine, 770 mg of 4,5-dichloro-6-isopropoxy-3(2H)-pyridazinone, 460 mg of trimethylamine and 20 ml of methanol, was refluxed under heating with stirring for 2 days. The solvent was distilled off under reduced pressure, and the residue was extracted with chloroform. The organic layer was washed with an aqueous potassium carbonate solution and then dried over anhydrous sodium sulfate. Then, the solvent was distilled off. The obtained residue was purified by silica gel column chromatography (ethyl acetate:methanol=9:1→chloroform:methanol=15:1) and then crystallized from diethyl ether to obtain 1.6 g of the above-identified compound as white crystals.

NMRδ: 6.55–7.15(m,7H), 4.45–5.33(m,6H), 3.13–3.88 (m,11H), 2.13–2.58(m,4H), 1.28(d,6H). MS(m/e): 465(M⁺–106), 430, 106(100%).

Preparation Example 8

4-Chloro-5-[3-{4-(4-N-formylbenzyl)-piperazin-1-yl}-carbonylmethoxy-4-methoxybenzylamino]-6-isopropoxy-3(2H)-pyridazinone

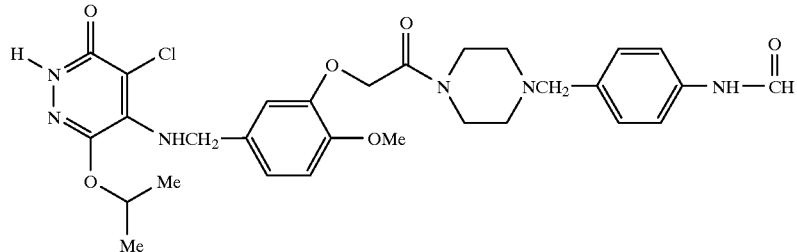

400 mg of 4-chloro-5-[3-(4-aminobenzyl)piperazin-1-yl]-carbonylmethoxy-4-methoxybenzylamino-6-isopropoxy-3(2H)pyridazinone was dissolved in 3 me of phenyl formate. The solution was stirred at room temperature overnight. The reaction solution was distilled under reduced pressure. Then, the obtained residue was purified by silica gel column chromatography (chloroform:methanol=9:1) and then crystallized from diethyl ether to obtain 380 mg of the above-identified compound as white crystals.

NMRδ: 11.75(br. s,1H), 8.2–8.85(m,2H), 6.75–7.62(m, 7H), 4.58–5.30(m,6H), 3.77(s,3H), 3.20–3.75(m,6H), 2.05–2.60(m,4H), 1.27(d,6H). MS(m/e): 464(M⁺–134), 137 (100%).

Preparation Example 9

4-Chloro-5-[3-{4-(4-N-acetylaminobenzyl)-piperazin-1-yl}-carbonylmethoxy-4-methoxybenzylamino]-6-isopropoxy-3(2H)-pyridazinone

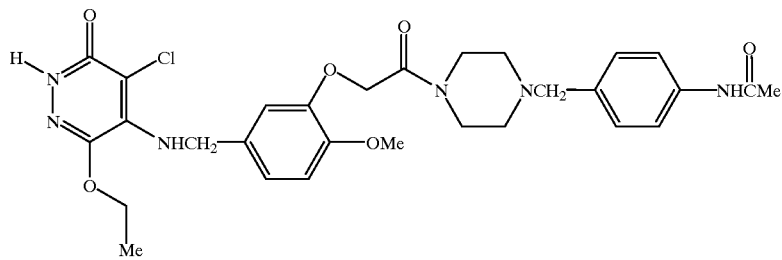

400 mg of 4-chloro-5-[3-(4-aminobenzyl)-piperazin-1-yl]-carbonylmethoxy-4-methoxybenzylamino-6-isopropoxy-3(2H)-pyridazinone was dissolved in 400 me of pyridine, and 220 mg of acetic anhydride was added thereto. The mixture was stirred at room temperature for 2 hours. The solvent was distilled off under reduced pressure, and the residue was extracted with chloroform. The organic layer was washed with an aqueous potassium carbonate solution and dried over anhydrous sodium sulfate. Then, the solvent was distilled off under reduced pressure. The obtained residue was purified by silica gel column chromatography (chloroform:methanol=9:1) and then crystallized from diethyl ether to obtain 340 mg of the above-identified compound as white crystals.

NMRδ: 11.84(br. s,1H), 8.24(br. s,1H), 6.63–7.52(m,8H), 4.52–5.30(m, 6H), 3.30–3.92(m,9H), 2.0–2.62(m,7H), 1.25 (d,6H). MS(m/e): 613(M⁺+H), 466.

Preparation Example 10

4-Bromo-5-[3-{2-(4-(4-chlorobenzyl)-piperazin-1-yl)-ethoxy}-4-methoxybenzylamino]-3(2H)-pyridazinone hydrochloride (Compound No. 7)

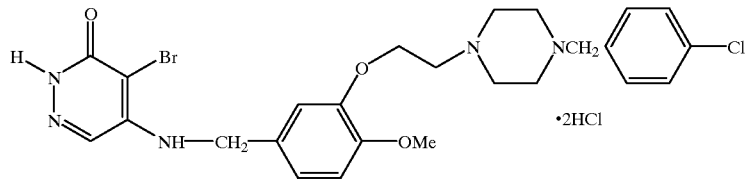

To a mixed solution comprising 440 mg of 4-bromo-5-[3-{2-(4-(4-chlorobenzyl)piperazin-1-yl)ethoxy}-4-methoxbenzylamino]-3(2H)-pyridazinone and 5 ml of chloroform, 10% hydrochloric acid methanol was added until the pH became from 2 to 3, and the mixture was stirred at room temperature for 2 hours. Diethyl ether was added to the reaction solution for crystallization to obtain 465 mg of the above-identified compound as white crystals having a melting point of from 176–183° C.

MS(m/e): 562($M^+$–2HCl), 482, 238, 223(100%), 203, 125, 91.

Preparation Example 11

4-Bromo-5-[3-{2-(4-(4-chlorobenzyl)-piperazin-1-yl)-ethoxy}-4-methoxybenzylamino]-3(2H)-pyridazinone fumarate (Compound No. 8)

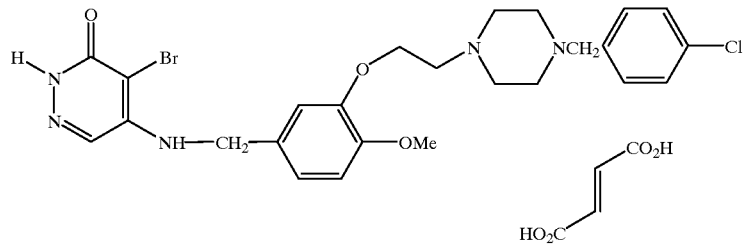

A mixture comprising 163 mg of 4-bromo-5-[3-{2-(4-(4-chlorobenzyl)-piperazin-1-yl)-ethoxy}-4-methoxybenzyl-amino]-3(2H)-pyridazinone, 33 mg of fumaric acid and 4 ml of chloroform, was stirred at room temperature for 3 hours. Diethyl ether was added to the reaction solution for crystallization to obtain 120 mg of the above-identified compound as white crystals having a melting point of from 178–185° C.

MS(m/e): 562($M^+$—(CHCO$_2$H)$_2$), 482, 237, 223, 125 (100%), 91.

Preparation Example 12

4-Bromo-5-[3-{2-(4-(4-chlorobenzyl)-piperazin-1-yl)-ethoxy }-4-methoxybenzylamino]-3(2H)-pyridazinone sulfate (Compound No. 9)

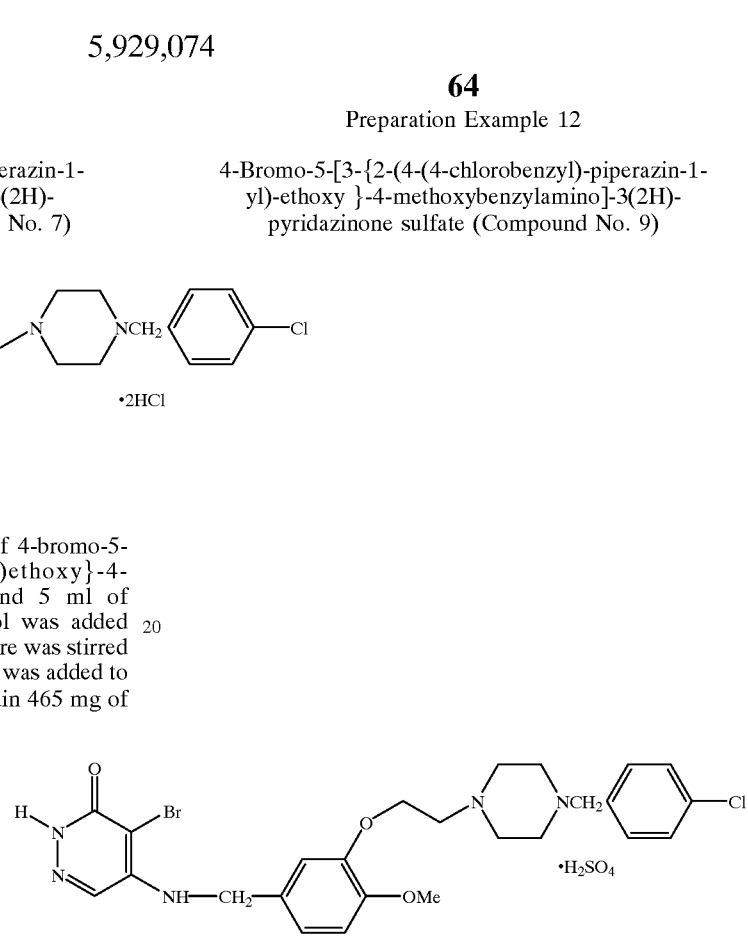

A mixture comprising 700 mg of 4-bromo-5-[3-{2-(4-(4-chlorobenzyl)-piperazin-1-yl)-ethoxy}-4-methoxybenzyl-amino]-3(2H)-pyridazinone, 5 ml of methanol, 5 ml of chloroform and 140 mg of sulfuric acid, was stirred at room temperature for 3 hours. The reaction solution was distilled off under reduced pressure, and the obtained residue was crystallized from isopropyl ether/diethyl ether to obtain 800 mg of the above-identified compound as white crystals having a melting point of 158–162° C. MS(m/e): 482($M^+$—Br—$H_2SO_4$), 238, 223 (100%), 125

Compounds prepared in accordance with the above Preparation Examples are shown in Table II. For the structures of these compounds, reference should be made to Compound Nos. shown in Table I. In the column at the right hand end in Table II, the number of applied Preparation Example is indicated.

| Compound No. | Melting point (°C.) | MS(m/e) | Example No. |
|---|---|---|---|
| 1 | Solid | 424($M^+$-HCl), 100(100%) | 10 |
| 2 | Solid | 414($M^+$-HCl), 100(100%) | 10 |
| 3 | 193–196 | 425($M^+$-HCl), 86(100%) | 10 |
| 4 | 170–180 | 483($M^+$-2HCl), 91(100%) | 10 |
| 5 | 179–186 | 527($M^+$-2HCl), 190(100%) | 10 |
| 6 | 128–135 | 527($M^+$-Q35), 203(100%) | 11 |
| 7 | 176–183 | See Example 10 | 10 |
| 8 | 178–185 | See Example 11 | 11 |
| 9 | 158–162 | See Example 12 | 12 |
| 10 | 159–163 | 517($M^+$-2HCl), 125(100%) | 10 |
| 11 | 179–184 | 517($M^+$-$H_2SO_4$), 125(100%) | 12 |
| 12 | 170–173 | 517($M^+$-Q35), 125(100%) | 11 |
| 13 | 180–187 | 545($M^+$-2HCl), 207(100%) | 10 |
| 14 | 184–188 | 545($M^+$-Q35), 109(100%) | 11 |
| 15 | 178–185 | 501($M^+$-2HCl), 221(100%) | 10 |
| 16 | 217–221 | 501($M^+$-Q35), 109(100%) | 11 |
| 17 | 157–162 | 573($M^+$-2HCl), 221(100%) | 10 |
| 18 | 62–70 | 438($M^+$-HCl), 86(100%) | 10 |
| 19 | 78–89 | 428($M^+$-HCl), 86(100%) | 10 |
| 20 | 159–168 | 421($M^+$-2HCl), 113(100%) | 10 |
| 21 | Solid | 435($M^+$-2HCl), 127(100%) | 10 |
| 22 | 173–177 | 541($M^+$-2HCl), 91(100%) | 10 |
| 23 | 175–180 | 569($M^+$-2HCl), 91(100%) | 10 |
| 24 | 201–205 | 542($M^+$-2HCl), 91(100%) | 10 |
| 25 | 164–167 | 531($M^+$-2HCl), 91(100%) | 10 |
| 26 | Solid | 515($M^+$-2HCl), 109(100%) | 10 |
| 27 | 169–172 | 543($M^+$-2Q35), 109(100%) | 11 |
| 28 | 163–171 | 557($M^+$-2Q35), 109(100%) | 11 |
| 29 | Solid | 576($M^+$-2HCl), 125(100%) | 10 |
| 30 | 98–120 | 565($M^+$-2HCl), 206(100%) | 10 |
| 31 | 143–148 | 429($M^+$-HCl), 92(100%) | 10 |
| 32 | 170–180 | 421($M^+$-HCl), 140(100%) | 10 |
| 33 | 161–178 | 465($M^+$-HCl), 140(100%) | 10 |
| 34 | 181–188 | 542($M^+$-2HCl), 92(100%) | 10 |
| 35 | 182–190 | 498($M^+$-2HCl), 134(100%) | 10 |
| 36 | 110–116 | 497($M^+$-Q36), 91(100%) | 11 |
| 37 | 177–180 | 497($M^+$-HCl), 91(100%) | 10 |
| 38 | 110–122 | 541($M^+$-Q36), 91(100%) | 11 |
| 39 | 112–124 | 515($M^+$-Q36), 109(100%) | 11 |
| 40 | 184–187 | 515($M^+$-HCl), 109(100%) | 10 |
| 41 | 82–86 | 543($M^+$-Q36), 234(100%) | 11 |
| 42 | 88–91 | 557($M^+$-Q35), 522(100%) | 11 |
| 43 | 105–112 | 559($M^+$-Q36), 109(100%) | 11 |
| 44 | 174–178 | 559($M^+$-HCl), 109(100%) | 10 |
| 45 | 165–173 | 526($M^+$-HCl), 92(100%) | 10 |
| 46 | 162–168 | 449($M^+$-HCl), 169(100%) | 10 |
| 47 | 136–138 | 525($M^+$-HCl), 91(100%) | 10 |
| 48 | 130–133 | 569($M^+$-HCl), 91(100%) | 10 |
| 49 | 130–135 | 553($M^+$-HCl), 91(100%) | 10 |
| 50 | 134–135 | 515($M^+$-44-Q35), 109(100%) | 10 |
| 51 | 133–137 |  | 10 |
| 52 | 128–129 | 529($M^+$-Q35), 109(100%) | 10 |
| 53 | 134–135 | 531($M^+$-2Q35), 207(100%) | 10 |
| 54 | 175–179 | 497($M^+$-2Q35), 91(100%) | 10 |
| 55 | 195–196 | 515($M^+$-2Q35), 109(100%) | 10 |
| 56 | 126–129 | 557($M^+$-Q35), 109(100%) | 10 |
| 57 | 142–144 | 543($M^+$-2Q35), 109(100%) | 10 |
| 58 | 121–125 | 564($M^+$-2Q35), 109(100%) | 10 |
| 59 | 108–110 | 548($M^+$-2Q35), 143(100%) | 10 |
| 60 | 126–128 | 646($M^+$-2Q35), 109(100%) | 10 |
| 61 | 113–117 | 548($M^+$-Q35), 143(100%) | 10 |
| 62 | 98–103 | 496($M^+$), 91(100%) | 1 |
| 63 | 112–115 | 482($M^+$-Q35), 91(100%) | 10 |
| 64 | 166–171 | 558($M^+$-1-Q35), 109(100%) | 10 |
| 65 | 162–163 | 545($M^+$-2Q35), 109(100%) | 10 |
| 66 | 174–175 | 541($M^+$-Q35), 91(100%) | 10 |
| 67 | 104–107 | 592($M^+$-Q36), 143(100%) | 10 |
| 68 | 108–110 | 573($M^+$-Q35), 109(100%) | 10 |
| 69 | 98–100 | 601($M^+$-Q35), 109(100%) | 10 |
| 70 | 184–186 | 559($M^+$-2Q35), 109(100%) | 10 |
| 71 | 118–119 | 592($M^+$-2Q35), 143(100%) | 10 |
| 72 | 130–132 | 690($M^+$+1-2Q35), 109(100%) | 10 |
| 73 | 106–109 | 691($M^+$+1-Q35), 109(100%) | 10 |
| 74 | 80–83 | 540($M^+$) | 6 |
| 75 | 105–108 | 526($M^+$-Q35), 91(100%) | 10 |
| 76 | 102–103 | 573($M^+$-Q35), 109(100%) | 10 |
| 77 | 94–96 | 615($M^+$+1-2Q35), 106(100%) | 10 |
| 78 | 87–89 | 465($M^+$-106), 106(100%) | 7 |
| 79 | 118–121 | 599($M^+$+1-Q35), 106(100%) | 10 |
| 80 | 121–123 | 613($M^+$+1-Q35), 106(100%) | 10 |

Formulation Example 1 (Tablets)

| | |
|---|---|
| Compound No. 39 | 10 g |
| Lactose | 20 g |
| Starch | 4 g |
| Starch for paste | 1 g |
| Magnesium stearate | 0.1 g |
| Carboxymethyl cellulose calcium | 7 g |
| Total | 42.1 g |

The above components were mixed in a usual manner, and formulated into sugar-coated tablets each containing 50 mg of an active ingredient.

Formulation Example 2 (Capsules)

| | |
|---|---|
| Compound No. 43 | 10 g |
| Lactose | 20 g |
| Microcrystal cellulose | 10 g |
| Magnesium stearate | 1 g |
| Total | 41 g |

The above components were mixed in a usual manner, and filled into gelatin capsules to obtain capsules each containing 50 mg of an active ingredient.

Formulation Example 3 (Soft capsules)

| | |
|---|---|
| Compound No. 7 | 10 g |
| Corn oil | 35 g |
| Total | 45 g |

The above components were mixed and formulated in a usual manner to obtain soft capsules.

Formulation Example 4 (Ointment)

| | |
|---|---|
| Compound No. 25 | 1.0 g |
| Olive Oil | 20 g |
| White vaseline | 79 g |
| Total | 100 g |

The above components were mixed in a usual manner to obtain 1% ointment.

Formulation Example 5 (Aerosol suspension)

| | | |
|---|---|---|
| (A) | Compound No. 37 | 0.25% |
| | Isopropyl myristate | 0.10% |
| | Ethanol | 26.40% |
| (B) | A 60-40% mixture of 1,2-dichlorotetrafluoroethane and 1-chloropentafluoroethane | 73.25% |

The above composition (A) was mixed. The solution mixture thereby obtained was charged in a container equipped with a valve, and the propellant (B) was injected from the valve nozzle to a gauge pressure of from about 2.46 to 2.81 $mg/cm^2$ to obtain an aerosol suspension.

Test Examples

I. Bronchodilating Effect

1. In vitro test

Drug:

A test sample drug was dissolved in 100% dimethylsulfoxide (DMSO, Wako Junyaku) and diluted for use. Leukotriene $D_4$ ($LTD_4$, Ultrafine) and isoproterenol (Isoproterenol, Sigma) were diluted with distilled water. Indomethacin (Indo, Sigma) was dissolved in 100% ethanol (EtOH, Komune Kagaku). Aminophylline (AP, Sigma), histamine dihydrochloride (His, Wako Junyaku) was dissolved in distilled water. The final concentrations of DMSO and EtOH in a bath were made not higher than 0.25% v/v and not higher than 0.1% v/v, respectively. Method 1:1:

A guinea-pig of 300–450 g was exsanguinated, and the trachea was taken out. After removing fat and connective tissues, it was cut and divided into 2 to 3 spiral strips, each having a width of about 2 mm and containing 4 smooth muscle tissues. Each specimen thus prepared was suspended in an organ bath of 8 ml containing a modified Tyrode solution aerated with 95% $O_2$+5% $CO_2$ at 37° C., and a load of 1 g was applied thereto. The relaxation of the muscle was recorded by a pen recorder (Yokogawa Hokushin Electric, type 3066) by means of an isotonic transducer (Nihon Kohden, TD-112S).

The composition of the modified Tyrode solution was as follows (mM):

NaCl 137, KCl 2.7, $CaCl_2$ 1.8, $MgCl_2$ 1.0, $NaHCO_3$ 20, $NaH_2PO_4$ 0.32, Glucose 11.

The specimen was allowed to stand for 50–60 minutes, and was contracted with histamine dihydrochloride (100 $\mu$M). After the reaction became constant, it was washed and allowed to stand for 20–30 minutes. Indomethacin (5 $\mu$M) was added thereto, and after incubation for 30 minutes, the specimen was contracted by adding $LTD_4$ (30 nM). After the reaction-became stable, a test sample drug was accumulatively administered. Finally, AP (1 mM) was added to achieve the maximum relaxation reaction. The result was expressed by relaxation percent relative to the relaxation by AP which was rated 100%, and a concentration to achieve 50% relaxation ($EC_{50}$, $\mu$M) was measured. As a control drug, AP was used. The results are shown in Table III-1.

TABLE III-1

| Test Compound No. | $EC_{50}$ ($\mu$M) | Test Compound No. | $EC_{50}$ ($\mu$M) |
|---|---|---|---|
| 4 | 1.7 | 36 | 0.32 |
| 5 | 0.42 | 39 | 0.16 |
| 7 | 0.49 | 43 | 0.40 |
| 13 | 0.45 | 47 | 0.77 |
| 15 | 0.48 | 48 | 0.95 |
| 17 | 3.3 | 49 | 1.1 |
| 22 | 0.39 | 51 | 6.1 |
| 23 | 1.3 | 53 | 3.1 |
| 24 | 2.0 | 54 | 2.4 |
| 25 | 0.47 | 55 | 7.3 |
| 26 | 0.75 | 64 | 0.32 |
| 27 | 4.0 | 66 | 0.18 |
| 30 | 2.6 | 67 | 0.17 |
| 31 | 6.9 | 76 | 0.69 |
| 34 | 3.8 | | |
| 35 | 6.6 | Aminophylline | 178 |

Method 1–2:

The same measuring method as method 1–1 was employed. The specimen was allowed to stand for from 60 to 90 minutes and then relaxed by an addition of 1 $\mu$M of isopreterenol. The specimen was washed, and this operation was repeated at an interval of from 30 to 40 minutes until a constant relaxation reaction was reached. Then, a test sample drug was accumulately applied to relax the specimen. Finally, 1 mM of AP was added to achieve the maximum relaxation reaction. The result was expressed by relaxation percent relative to the relaxation by AP which was rated 100%, and a concentration to achieve 50% relaxation ($EC_{50}$, $\mu$M) was obtained. The final concentration of DMSO in the bath was adjusted to be 0.2 v/v%. As a control drug, AP was used. The results are shown in Table III-2.

TABLE III-2

| Test Compound No. | $EC_{50}$ ($\mu$M) | Test Compound No. | $EC_{50}$ ($\mu$M) |
|---|---|---|---|
| 16 | 0.34 | 66 | 0.067 |
| 24 | 0.98 | 67 | 0.041 |
| 26 | 0.91 | 69 | 0.43 |
| 36 | 0.24 | 71 | 0.25 |
| 39 | 0.17 | 73 | 0.49 |
| 43 | 0.28 | 74 | 0.046 |
| 47 | 0.54 | 75 | 0.40 |
| 48 | 0.21 | 76 | 0.048 |
| 51 | 0.097 | 77 | 0.057 |
| 54 | 0.3 | 78 | 0.014 |
| 61 | 0.31 | 79 | 0.041 |
| 62 | 0.05 | 80 | 0.039 |
| 64 | 0.061 | | |
| 65 | 0.36 | Aminophylline | 37 |

(2) in vivo test

Effect on anaphylactic bronchoconstriction mediated by endogeneously liberated SRS-A in passively sensitized guinea-pig Male guinea-pigs (350–450 g) were passively sensitized with intravenous (i.v.) injection of 0.125 ml rabbit anti-EA (egg albumin) serum (Capple Laboratories) 1 to 2 days preceding the experiment. Antigen-induced anaphylactic bronchoconstrictions mediated by endogeneously liberated SRS-A were measured by modified method of Konzett and Rossler (Arch. Exp. Path. Pharmak., 195, 71, 1940). Sensitized quinea-pigs were anaesthetized with intraperitoneal injection of urethane (1.5 g/kg). The right jugular vein was cannulated for the administration of the all agents and trachea was cannulated to record total pulmonary resistance. Guinea-pigs were artificially ventilated by a small animal respirator (Shinano, Model SN-480-7) set at a stroke volume of 4.5 ml and a rate of 50 breaths per min. The change in pulmonary resistance was measured with a pressure transducer (Nihon Kohden, Model TP-602T) connected to a T-tube on the tracheal cannula. The percentage of the maximum bronchoconstriction obtained by clamping off the trachea. Following surgical preparation, the animals were pretreated with indomethacin (2 mg/kg, 10 min), pyrilamine (2 mg/kg, 6 min) and propranolol (0.1 mg/kg, 5 min) prior to the EA challenge (0.2 mg/kg). All test compounds were administered orally 2 hours before the EA challenge. Inhibition (%) of broncho-constriction was determined as follows: Inhibition (%)=(1.0-% maximum bronchoconstriction in test/% maximum bronchoconstriction in control)×100. The maximum bronchoconstriction was 62±6% (Mean±S.E.M; n=6) and the number of test animals was 5–6.

The inhibition ratio at a dose of 30 mg/kg of the test compound is shown in Table III-3.

TABLE III-3

| Test Compound No. | Inhibition (%) |
|---|---|
| 7 | 59 |
| 8 | 32 |
| 25 | 59 |
| 26 | 36 |
| 36 | 41 |
| 37 | 54 |
| 39 | 63 |
| 43 | 62 |
| 47 | 37 |
| 64 | 26 |
| 67 | 29 |
| 74 | 30 |
| 77 | 65 |
| 78 | 54 |
| 80 | 30 |

II. Antiallergic Effect

Binding test employing $^3$H-pyrilamine (histamine $H_1$ receptor-binding test)

The test was carried out in accordance with the method of Chang et al (J. Neurochem., 32, 1653 (1979)).

Tritiated pyrilamine was added to a suspension of bovine cerebellum and a 50 mM phosphate buffer solution (pH 7.5), and the mixture was left to stand still at 25° C. for 30 minutes. Then, the mixture was rapidly filtered under suction through a glass fiber filter paper, and the radio activities on the filter paper were measured. The inhibition ratio against $H_1$-receptor at a concentration of the test compound being 10 $\mu$M, was calculated by the following equation.
Inhibition ratio (%)=

{1-(binding amount in the presence of the drug—non-specific binding amount)/(total binding amount—non-specific binding amount)}×100 where the total binding amount is $^3$H-pyrilamine-binding radio activity in the absence of the test compound, and the non-specific binding amount is $^3$H-pyrilamine-binding radio activity in the presence of 10 $\mu$M of triprolisine. The results are shown in Table IV.

TABLE IV

| Test Compound No. | Inhibition (%) | Test Compound No. | Inhibition (%) |
|---|---|---|---|
| 7 | 56.1 | 24 | 89.2 |
| 8 | 56.5 | 25 | 94.4 |
| 17 | 55.8 | 26 | 92.6 |
| 22 | 86.6 | 29 | 93.6 |
| 23 | 92.2 | 30 | 90.5 |

III. Anti-platelet aggregation effect

Anti-platelet aggregation effect in rabbits

Blood was collected from the abdominal artery of Japanese white male rabbits (weight: 1.8 to 2.5 kg) into a syringe containing 1/10 volume 3.8% sodium citrate. The blood thus obtained was subjected to a centrifugation at 200×g for 7 minutes at room temperature to obtain platelet rich plasma (PRP). Furthermore, the residue was subjected to a centrifugation at 2000×g for 10 minutes to obtain platelet poor plasma (PPP). The measurement was effected by diluting PRP with PPP to 300,000/mm$^3$. PRP and PPP were placed in a cuvette, and the measurement range of transmittance was adjusted to 0% in the case of PRP and to 100% in the case of PPP. Thereafter, a test sample drug dissolved in 100% dimethylsulfoxide (DMSO) was added to PRP (the final concentration of DMSO: 0.25%). After incubation was effected at 37° C. at 900 rpm for 2 minutes, an aggregating agent was added to record an aggregation curve. The anti-platelet aggregation effect of the test sample drug was expressed by a concentration (IC$_{50}$: $\mu$M) at which the aggregation of control sample was 50% inhibited. The aggregating agent ADP was used at the minimum concentration (5 to 10 $\mu$M) which caused the maximum aggregation. The measurement of platelet aggregation was carried out by using NBS HEMA TRACER 601. The results are shown in Table V.

TABLE V

| Test Compound No. | IC$_{50}$ ($\mu$M) | Test Compound No. | IC$_{50}$ ($\mu$M) |
|---|---|---|---|
| 4 | 5.2 | 25 | 5.1 |
| 5 | 4.1 | 36 | 1.6 |
| 6 | 3.9 | 38 | 1.2 |
| 7 | 5.4 | 39 | 1.4 |
| 8 | 5.5 | 43 | 2.2 |
| 13 | 2.9 | 47 | 5.7 |
| 14 | 3.5 | 48 | 4.0 |
| 15 | 4.5 | 51 | 1.1 |
| 16 | 5.2 | 64 | 0.39 |
| 22 | 2.1 | 67 | 0.4 |
| 23 | 4.6 | | |

INDUSTRIAL APPLICABILITY

As is evident from the above results, the compounds of the present invention have excellent bronchodilating activities, antiallergic activities and antiplatelet aggregation activities. The compounds of the present invention exhibit strong pharmacological activities even by oral administration. Thus, they can be prophylactic and therapeutic drugs useful for immediate allergic diseases such as bronchial asthma, allergic rhinitis, hives and hey fever, various inflammatory diseases such as rhematic arthritis and spinal anthritis, ischemic diseases such as angina pectoris and cardiac infarction, and various thrombotic diseases.

We claim:

1. A 3(2H)-pyridazinone compound of the formula (I):

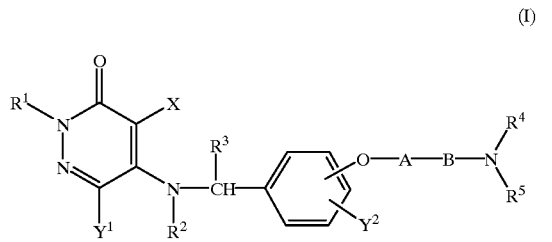

wherein each of $R^1$, $R^2$ and $R^3$ which are independent of one another, is a hydrogen atom or a $C_{1-4}$ alkyl group, X is a chlorine atom or a bromine atom, $Y^1$ is a $C_{1-4}$ alkoxy group, $Y^2$ is a hydrogen atom, a halogen atom, a hydroxyl group, a $C_{1-4}$ alkyl group or a $C_{1-4}$ alkoxy group, A is a $C_{1-5}$ alkylene chain which may be substituted by a hydroxyl group, B is a carbonyl group or a methylene chain which may be substituted by a $C_{1-4}$ alkyl group, and (a) each of $R^4$ and $R^5$ which are independent of each other is a $C_{1-4}$ alkyl group or (b) $R^4$ is a hydrogen atom and $R^5$ is —Z—Ar (wherein Z is a $C_{1-5}$ alkylene chain and Ar is an aromatic 6-membered ring which may contain a nitrogen atom) or (c) $R^4$ and R5 together form a $C_{2-6}$ cyclic alkylene group, or (d) $R^4$ and $R^5$ form together with the adjacent nitrogen atom a 4-substituted piperidine ring of the formula:

{wherein $R^{11}$ is a $C_{1-4}$ alkyl group (this alkyl group may be substituted by one or more substituents selected from a group of substituents consisting of a phenyl group which may be substituted by $Y^3$ (wherein $Y^3$ is a hydrogen atom, a halogen atom, a $C_{1-4}$ alkyl group, a $C_{1-4}$ alkoxy group, an amino group, an N-formyl group or a $C_{1-4}$ alkylcarbonylamino group) and a hydroxyl group)}, or a pharmaceutically acceptable salt thereof.

2. The 3(2H)-pyridazinone compound according to the claim 1, wherein each of $R^2$ and $R^3$ is a hydrogen atom, or a pharmaceutically acceptable salt thereof.

3. A process for producing the 3(2H)-pyridazinone compound or its pharmaceutically acceptable salt as defined as claim 1, which comprises reacting a 5-dihalo-3(2H)-pyridazinone compound of the formula (II);

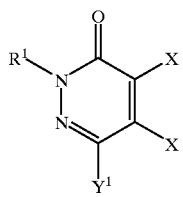

wherein each of $R^1$ is a hydrogen atom or a $C_{1-4}$ alkyl group, X is a chlorine atom or a bromine atom, and $Y^1$ is a $C_{1-4}$ alkoxy group, with an alkoxybenzylamine derivative of the formula (III) or its salt:

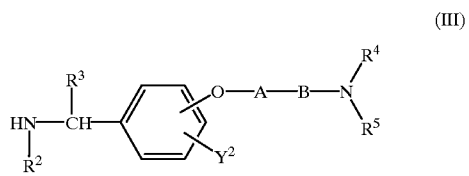

wherein each of $R^2$ and $R^3$ which are independent of one another, is a hydrogen atom or a $C_{1-4}$ alkyl group, $Y^2$ is a hydrogen atom, a halogen atom, a hydroxyl group, a $C_{1-4}$ alkyl group or a $C_{1-4}$ alkoxy group, A is a $C_{1-5}$ alkylene chain which may be substituted by a hydroxyl group, B is a carbonyl group or a methylene chain which may be substituted by a $C_{1-4}$ alkyl group, and (a) each of $R^4$ and $R^5$ which are independent of each other is a $C_{1-4}$ alkyl group or (b) $R^4$ is a hydrogen atom and $R^5$ is —Z—Ar (wherein Z is a $C_{1-5}$ alkylene chain and Ar is an aromatic 6-membered ring which may contain a nitrogen atom) or (c) $R^4$ and $R^5$ together form a $C_{2-6}$ cyclic alkylene group, or (d) $R^4$ and $R^5$ form together with the adjacent nitrogen atom a 4-substituted piperidine ring of the formula:

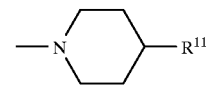

{wherein $R^{11}$ is a $C_{1-4}$ alkyl group (this alkyl group may be substituted by one or more substituents selected from a group of substituents consisting of a phenyl group which may be substituted by $Y^3$ (wherein $Y^3$ is a hydrogen atom, a halogen atom, a $C_{1-4}$ alkyl group, a $C_{1-4}$ alkoxy group, an amino group, an N-formyl group or a $C_{1-4}$ alkylcarbonylamino group) and a hydroxyl group)} optionally in the presence of an acid-binding agent.

4. A composition comprising a pharmaceutically acceptable carrier and, in bronchodilator, antiallergic or antiplatelet, effective amounts, the 3(2H)-pyridazinone compound or its pharmaceutically acceptable salt as defined in claim 1.

5. A method for treating a patient in need thereof with a bronchodilator comprising administering the 3(2H)-pyridazinone compound or its pharmaceutically acceptable salt as defined in claim 1 in an effective amount.

6. A method for treating a patient in need thereof with a antiallergic drug comprising administering the 3(2H)-pyridazinone compound or its pharmaceutically acceptable salt as defined in claim 1 in an effective amount.

7. A method for treating a patient in need thereof with a antiplatelet agent comprising administering the 3(2H)-pyridazinone compound or its pharmaceutically acceptable salt as defined in claim 1 in an effective amount.

* * * * *